United States Patent
Clapp et al.

(10) Patent No.: US 12,226,313 B2
(45) Date of Patent: Feb. 18, 2025

(54) PROSTHETIC HEART VALVE DEVICE, DELIVERY SYSTEM, INTERVENTIONAL SYSTEM AND RELATED METHOD

(71) Applicant: LAGUNA TECH USA, INC., Irvine, CA (US)

(72) Inventors: Charlie Clapp, Irvine, CA (US); Gilbert Madrid, Irvine, CA (US)

(73) Assignee: Laguna Tech USA, Inc., Irvine, CA (US)

(*) Notice: Subject to any disclaimer, the term of this patent is extended or adjusted under 35 U.S.C. 154(b) by 0 days.

(21) Appl. No.: 18/557,766

(22) PCT Filed: Oct. 12, 2022

(86) PCT No.: PCT/IB2022/059766
§ 371 (c)(1),
(2) Date: Oct. 27, 2023

(87) PCT Pub. No.: WO2023/062551
PCT Pub. Date: Apr. 20, 2023

(65) Prior Publication Data
US 2024/0074853 A1 Mar. 7, 2024

Related U.S. Application Data

(60) Provisional application No. 63/394,299, filed on Aug. 2, 2022, provisional application No. 63/311,577, filed
(Continued)

(51) Int. Cl.
*A61F 2/24* (2006.01)

(52) U.S. Cl.
CPC .......... *A61F 2/2418* (2013.01); *A61F 2/2433* (2013.01); *A61F 2220/0008* (2013.01)

(58) Field of Classification Search
CPC .... A61F 2/2418; A61F 2/2412; A61F 2/2409; A61F 2/2427; A61F 2/243; A61F 2/246;
(Continued)

(56) References Cited

U.S. PATENT DOCUMENTS

| 7,914,575 B2 | 3/2011 | Guyenot et al. |
| 8,002,825 B2 | 8/2011 | Letac et al. |

(Continued)

FOREIGN PATENT DOCUMENTS

| CN | 101919752 B | 4/2014 |
| CN | 105125322 B | 3/2017 |

(Continued)

OTHER PUBLICATIONS

PCT International Search Report and Written Opinion for PCT/IB2022/059766, Laguna Tech USA, Inc., Forms PCT/ISA/220, 210, and 237 dated Mar. 15, 2023 (17 pages).

*Primary Examiner* — Seema Mathew
(74) *Attorney, Agent, or Firm* — BLAIR WALKER IP SERVICES, LLC

(57) ABSTRACT

A prosthetic aortic valve device, delivery system, interventional system, and related method are disclosed. The device includes an inner frame having relative compressed and expanded configurations; leaflets connected to the inner frame and cooperating with each other to control opening and closing of the blood flow passage; and a positioning mechanism arranged in a circumferential direction of the inner frame, the positioning mechanism including a fixed end connected to the inner frame and a free end extending towards the inflow end, the positioning mechanism being configured to be switchable among a loaded configuration, a transition configuration, and a released configuration.

28 Claims, 50 Drawing Sheets

Related U.S. Application Data on Feb. 18, 2022, provisional application No. 63/254,994, filed on Oct. 12, 2021.

(58) Field of Classification Search
CPC ........ A61F 2/2457; A61F 2/2475; A61F 2/90; A61F 2/02; A61F 2/07; A61F 2250/0069; A61F 2250/0048; A61F 2/2433; A61F 2250/006; A61F 2/2439; A61F 2/2445; A61F 2/24

See application file for complete search history.

(56) References Cited

U.S. PATENT DOCUMENTS

| | | | |
|---|---|---|---|
| 8,252,051 B2 | 8/2012 | Chau et al. | |
| 8,317,858 B2 * | 11/2012 | Straubinger | A61F 2/82 |
| | | | 623/2.12 |
| 8,398,704 B2 | 3/2013 | Straubinger et al. | |
| 8,403,983 B2 | 3/2013 | Quadri et al. | |
| 8,449,599 B2 | 5/2013 | Chau et al. | |
| 8,647,381 B2 * | 2/2014 | Essinger | A61F 2/2418 |
| | | | 623/1.24 |
| 8,808,367 B2 | 8/2014 | Suri et al. | |
| 8,986,371 B2 | 3/2015 | Quill et al. | |
| 9,023,100 B2 * | 5/2015 | Quadri | A61F 2/2418 |
| | | | 623/2.11 |
| 9,039,757 B2 | 5/2015 | McLean et al. | |
| 9,066,799 B2 | 6/2015 | Seguin et al. | |
| 9,192,466 B2 | 11/2015 | Kovalsky et al. | |
| 9,295,547 B2 | 3/2016 | Costello et al. | |
| 9,393,111 B2 | 7/2016 | Ma et al. | |
| 9,522,062 B2 | 12/2016 | Tuval | |
| 9,554,897 B2 | 1/2017 | Lane et al. | |
| 9,585,747 B2 | 3/2017 | Quadri et al. | |
| 9,655,722 B2 * | 5/2017 | Morriss | A61F 2/2436 |
| 9,744,036 B2 | 8/2017 | Duffy et al. | |
| 9,848,985 B2 | 12/2017 | Yang et al. | |
| 9,987,133 B2 * | 6/2018 | Straubinger | A61F 2/2412 |
| 10,016,276 B2 * | 7/2018 | Brunnett | A61F 2/2412 |
| 10,058,418 B2 | 8/2018 | Righini | |
| 10,064,719 B2 * | 9/2018 | Börtlein | A61F 2/2418 |
| 10,098,736 B2 | 10/2018 | Carmi et al. | |
| 10,149,759 B2 | 12/2018 | Naor | |
| 10,201,419 B2 | 2/2019 | Vidlund et al. | |
| 10,292,813 B2 | 5/2019 | Braido et al. | |
| 10,292,816 B2 | 5/2019 | Raanini et al. | |
| 10,321,992 B2 * | 6/2019 | Quill | A61F 2/2427 |
| 10,368,990 B2 | 8/2019 | Noe et al. | |
| 10,390,952 B2 * | 8/2019 | Hariton | A61F 2/2418 |
| 10,405,976 B2 | 9/2019 | Christianson et al. | |
| 10,433,961 B2 * | 10/2019 | McLean | A61F 2/2436 |
| 10,441,421 B2 * | 10/2019 | Perszyk | A61F 2/2454 |
| 10,456,243 B2 | 10/2019 | Robertson et al. | |
| 10,507,102 B2 | 12/2019 | Chau et al. | |
| 10,583,000 B2 * | 3/2020 | Ratz | A61F 2/2409 |
| 10,583,002 B2 | 3/2020 | Lane et al. | |
| 10,639,143 B2 | 5/2020 | Oba et al. | |
| 10,702,379 B2 * | 7/2020 | Garde | A61F 2/2409 |
| 10,736,737 B2 | 8/2020 | Mesana et al. | |
| 10,828,150 B2 | 11/2020 | Tamir | |
| 10,835,375 B2 | 11/2020 | Ganesan et al. | |
| 10,881,512 B2 | 1/2021 | Cooper et al. | |
| 10,952,849 B2 | 3/2021 | Rabito et al. | |
| 10,966,827 B2 | 4/2021 | Rowe et al. | |
| 10,993,804 B2 * | 5/2021 | Braido | A61F 2/2418 |
| 10,993,805 B2 | 5/2021 | Straubinger et al. | |
| 11,045,183 B2 | 6/2021 | Vidlund et al. | |
| 11,253,363 B2 * | 2/2022 | Zhang | A61F 2/2418 |
| 11,259,923 B2 | 3/2022 | Zhang et al. | |
| 11,337,800 B2 * | 5/2022 | Schreck | A61F 2/2418 |
| 11,382,746 B2 * | 7/2022 | Hariton | A61F 2/2436 |
| 11,446,144 B2 * | 9/2022 | Zhang | A61F 2/2436 |
| 11,969,163 B2 * | 4/2024 | Hacohen | A61F 2/2436 |
| 2003/0036791 A1 * | 2/2003 | Philipp | A61F 2/2418 |
| | | | 623/1.11 |
| 2005/0137686 A1 | 6/2005 | Salahieh et al. | |
| 2006/0212111 A1 | 9/2006 | Case et al. | |
| 2008/0071366 A1 * | 3/2008 | Tuval | A61F 2/2418 |
| | | | 623/2.11 |
| 2008/0082166 A1 * | 4/2008 | Styrc | A61F 2/2418 |
| | | | 623/2.18 |
| 2009/0054976 A1 * | 2/2009 | Tuval | A61F 2/2427 |
| | | | 623/2.11 |
| 2010/0049313 A1 | 2/2010 | Alon et al. | |
| 2010/0094411 A1 * | 4/2010 | Tuval | A61F 2/2427 |
| | | | 623/2.11 |
| 2010/0268332 A1 * | 10/2010 | Tuval | A61F 2/2418 |
| | | | 623/2.1 |
| 2011/0208290 A1 * | 8/2011 | Straubinger | A61F 2/2412 |
| | | | 623/1.36 |
| 2011/0208293 A1 * | 8/2011 | Tabor | A61B 5/1076 |
| | | | 623/1.26 |
| 2011/0208297 A1 | 8/2011 | Tuval et al. | |
| 2011/0218620 A1 * | 9/2011 | Meiri | A61B 17/0487 |
| | | | 623/2.11 |
| 2011/0264206 A1 * | 10/2011 | Tabor | A61F 2/2418 |
| | | | 623/2.12 |
| 2011/0295363 A1 * | 12/2011 | Girard | A61F 2/2412 |
| | | | 623/1.26 |
| 2012/0022633 A1 * | 1/2012 | Olson | A61F 2/2439 |
| | | | 623/2.11 |
| 2012/0046742 A1 * | 2/2012 | Tuval | A61F 2/2469 |
| | | | 623/2.18 |
| 2012/0053682 A1 * | 3/2012 | Kovalsky | A61F 2/2418 |
| | | | 623/2.11 |
| 2012/0078353 A1 * | 3/2012 | Quadri | A61F 2/2436 |
| | | | 623/2.14 |
| 2012/0158129 A1 * | 6/2012 | Duffy | A61F 2/2427 |
| | | | 623/2.11 |
| 2012/0303038 A1 | 11/2012 | Durante et al. | |
| 2013/0018458 A1 | 1/2013 | Yohanan et al. | |
| 2013/0073030 A1 * | 3/2013 | Tuval | A61F 2/2436 |
| | | | 623/2.18 |
| 2013/0079869 A1 * | 3/2013 | Straubinger | A61F 2/2418 |
| | | | 623/1.26 |
| 2013/0150956 A1 * | 6/2013 | Yohanan | A61F 2/2418 |
| | | | 623/2.14 |
| 2013/0261737 A1 * | 10/2013 | Costello | A61F 2/2418 |
| | | | 623/2.11 |
| 2013/0310928 A1 * | 11/2013 | Morriss | A61F 2/2409 |
| | | | 623/2.18 |
| 2014/0018915 A1 * | 1/2014 | Biadillah | A61F 2/2418 |
| | | | 623/2.17 |
| 2014/0039614 A1 * | 2/2014 | Delaloye | A61F 2/2436 |
| | | | 623/2.36 |
| 2014/0088680 A1 * | 3/2014 | Costello | A61F 2/2436 |
| | | | 623/1.2 |
| 2014/0135908 A1 * | 5/2014 | Glozman | A61F 2/2412 |
| | | | 623/2.11 |
| 2015/0018944 A1 * | 1/2015 | O'Connell | A61F 2/2427 |
| | | | 623/2.42 |
| 2015/0119982 A1 * | 4/2015 | Quill | A61F 2/2409 |
| | | | 623/2.38 |
| 2015/0127093 A1 * | 5/2015 | Hosmer | A61F 2/2433 |
| | | | 623/2.11 |
| 2015/0142100 A1 * | 5/2015 | Morriss | A61F 2/2445 |
| | | | 623/2.4 |
| 2015/0148896 A1 * | 5/2015 | Karapetian | A61F 2/88 |
| | | | 623/2.11 |
| 2015/0157455 A1 * | 6/2015 | Hoang | A61M 25/01 |
| | | | 264/269 |
| 2015/0305860 A1 * | 10/2015 | Wang | A61F 2/2409 |
| | | | 623/2.38 |
| 2015/0351903 A1 * | 12/2015 | Morriss | A61F 2/2418 |
| | | | 623/2.11 |
| 2015/0351904 A1 * | 12/2015 | Cooper | A61F 2/2418 |
| | | | 623/2.1 |
| 2015/0359631 A1 * | 12/2015 | Sheahan | A61F 2/2418 |
| | | | 623/2.19 |
| 2016/0030171 A1 * | 2/2016 | Quijano | A61F 2/2418 |
| | | | 623/1.26 |

(56) References Cited

U.S. PATENT DOCUMENTS

| | | |
|---|---|---|
| 2016/0038280 A1 | 2/2016 | Morriss et al. |
| 2016/0158007 A1* | 6/2016 | Centola ................. A61F 2/2436 623/2.11 |
| 2016/0213465 A1 | 7/2016 | Girard et al. |
| 2016/0220364 A1 | 8/2016 | Straubinger et al. |
| 2016/0270917 A1* | 9/2016 | Tuval ................. A61F 2/2469 |
| 2016/0331525 A1* | 11/2016 | Straubinger .............. A61F 2/07 |
| 2016/0354203 A1* | 12/2016 | Tuval ................... A61F 2/2409 |
| 2017/0128199 A1* | 5/2017 | Gurovich .............. A61F 2/2418 |
| 2017/0209265 A1 | 7/2017 | Karapetian et al. |
| 2017/0216023 A1 | 8/2017 | Lane et al. |
| 2017/0216026 A1* | 8/2017 | Quill ................... A61F 2/2418 |
| 2017/0231765 A1* | 8/2017 | Desrosiers ............ A61F 2/2436 623/2.11 |
| 2017/0325945 A1* | 11/2017 | Dale ................... A61F 2/2412 |
| 2018/0014931 A1* | 1/2018 | Morriss ................ A61F 2/2418 |
| 2018/0055629 A1* | 3/2018 | Oba ........................ A61L 27/04 |
| 2018/0078370 A1 | 3/2018 | Kovalsky et al. |
| 2018/0104056 A1* | 4/2018 | Salahieh ............... A61F 2/2418 |
| 2018/0116790 A1* | 5/2018 | Ratz .................... A61F 2/2439 |
| 2018/0177595 A1 | 6/2018 | Krans et al. |
| 2018/0221147 A1 | 8/2018 | Ganesan et al. |
| 2018/0303612 A1 | 10/2018 | Pasquino et al. |
| 2019/0099266 A1* | 4/2019 | Nelson ................. A61F 2/2415 |
| 2019/0133756 A1* | 5/2019 | Zhang .................. A61F 2/2436 |
| 2019/0151091 A1 | 5/2019 | Dwork et al. |
| 2019/0224008 A1 | 7/2019 | Bressloff et al. |
| 2019/0247189 A1 | 8/2019 | Dale et al. |
| 2019/0262129 A1* | 8/2019 | Cooper ................ A61F 2/2418 |
| 2019/0321178 A1 | 10/2019 | Tegels |
| 2020/0060818 A1* | 2/2020 | Geist .................... A61F 2/2436 |
| 2020/0121457 A1 | 4/2020 | Tegels |
| 2020/0138572 A1 | 5/2020 | Zhao et al. |
| 2020/0146814 A1 | 5/2020 | Fung et al. |
| 2020/0197172 A1* | 6/2020 | Tuval ....................... A61F 2/24 |
| 2020/0276014 A1 | 9/2020 | Burkart et al. |
| 2021/0077083 A1 | 3/2021 | Thambar et al. |
| 2021/0145576 A1 | 5/2021 | Becerra et al. |
| 2021/0154010 A1 | 5/2021 | Schneider et al. |
| 2021/0161658 A1* | 6/2021 | Tuval ................... A61F 2/2418 |
| 2021/0205077 A1* | 7/2021 | Wang ................... A61F 2/2409 |
| 2022/0008198 A1 | 1/2022 | Dai |
| 2022/0015898 A1 | 1/2022 | Li et al. |
| 2022/0031454 A1* | 2/2022 | Straubinger .......... A61F 2/2409 |
| 2023/0038809 A1* | 2/2023 | Clapp .................. A61F 2/2418 |
| 2023/0078372 A1* | 3/2023 | Madrid ................ A61F 2/2418 623/2.18 |
| 2023/0172712 A1* | 6/2023 | Straubinger .......... A61F 2/2418 623/2.11 |

FOREIGN PATENT DOCUMENTS

| | | |
|---|---|---|
| CN | 105662652 B | 12/2017 |
| CN | 110507451 A | 11/2019 |
| CN | 112618105 A | 4/2021 |
| CN | 114886614 A | 8/2022 |
| CN | 114886615 A | 8/2022 |
| EP | 3583920 A1 | 12/2019 |
| WO | WO 2010/080594 A2 | 7/2010 |
| WO | WO 2010/117680 A1 | 10/2010 |
| WO | WO 2011/147849 A1 | 12/2011 |
| WO | WO 2012/047644 A2 | 4/2012 |
| WO | WO2013/012801 A2 | 1/2013 |
| WO | WO2014/153152 A1 | 9/2014 |
| WO | WO 2018/211344 A1 | 11/2018 |
| WO | WO 2019/099864 A1 | 5/2019 |
| WO | WO2019/136292 A1 | 7/2019 |
| WO | WO2023/012680 A1 | 2/2023 |
| WO | WO2023/014593 A1 | 2/2023 |

* cited by examiner

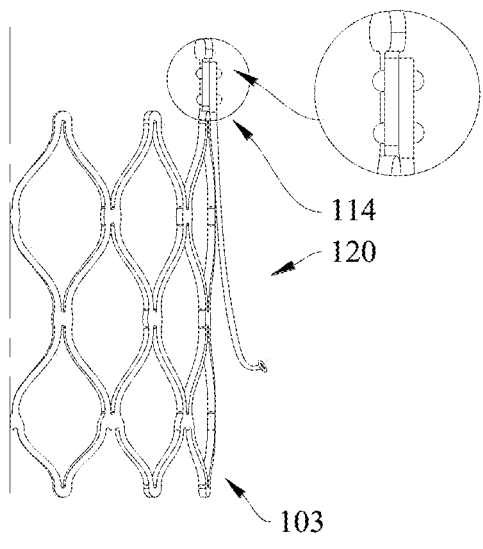
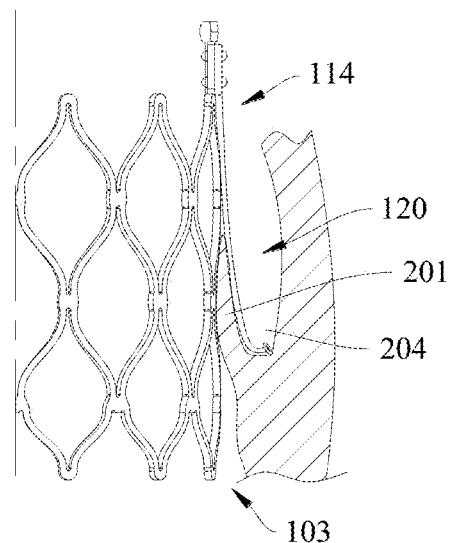
FIG. 3a
FIG. 3b
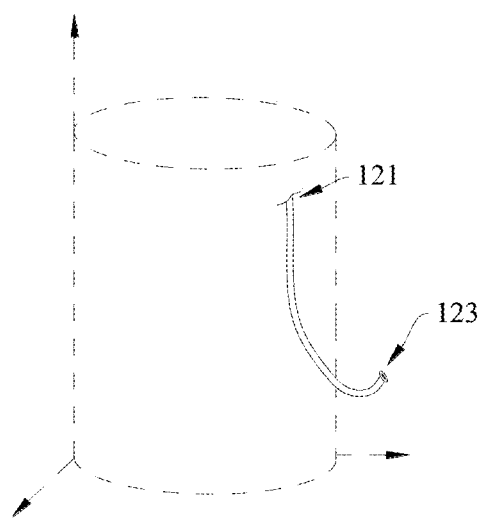
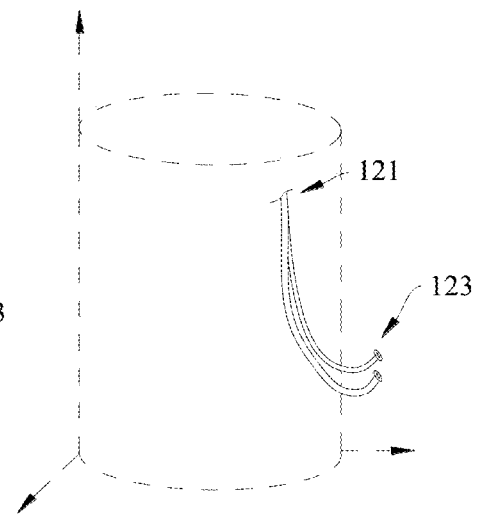
FIG. 4a
FIG. 4b

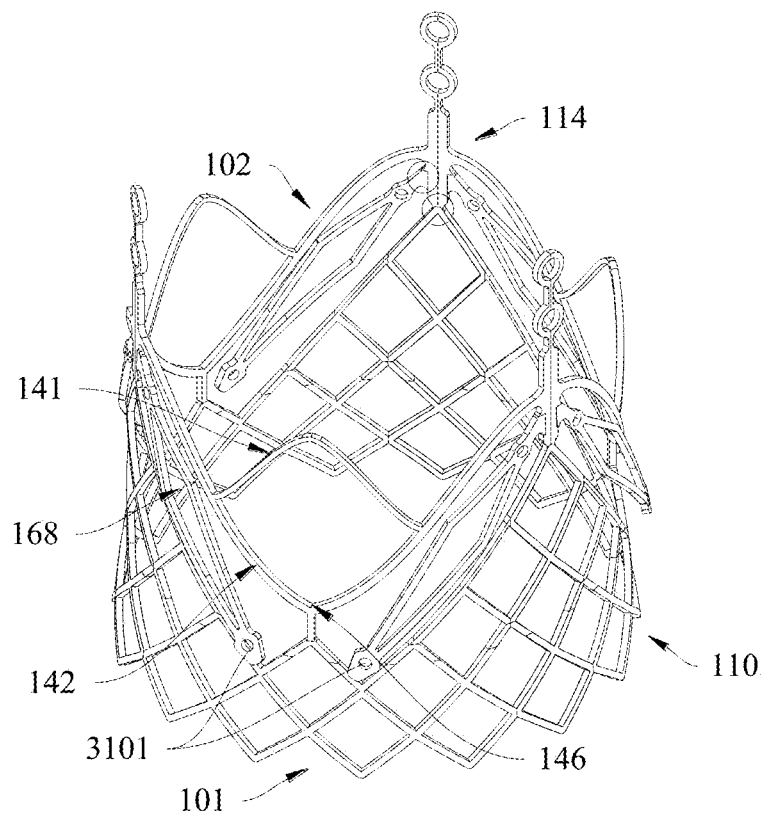
FIG. 7
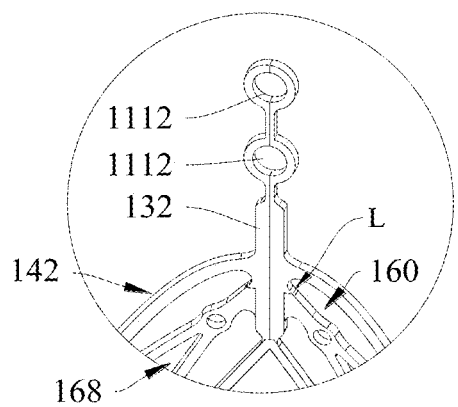 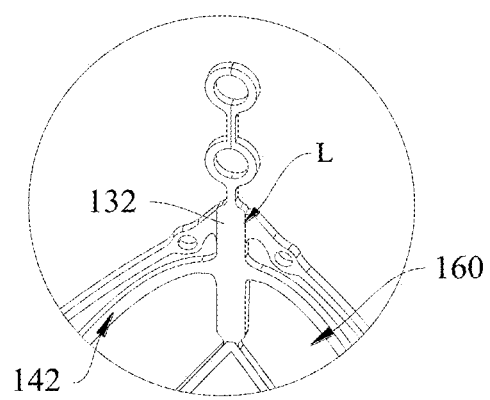
FIG. 8   FIG. 9

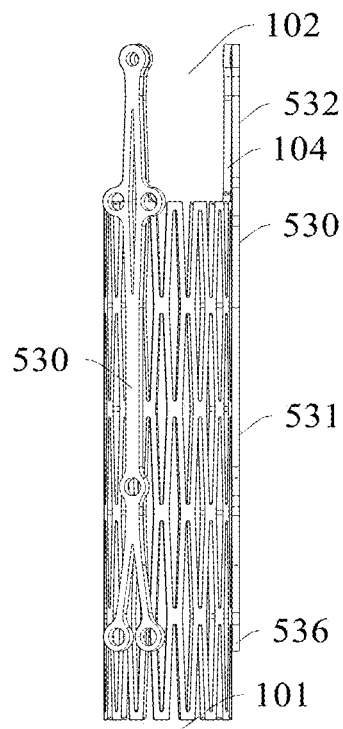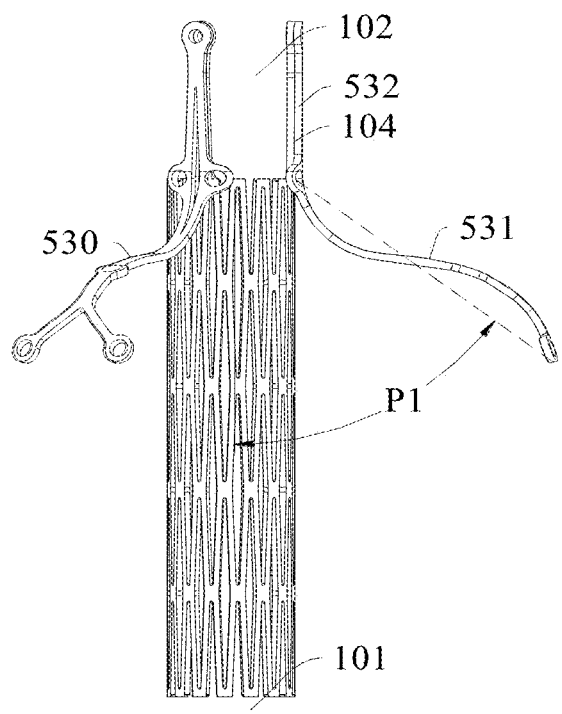
FIG. 29  FIG. 30
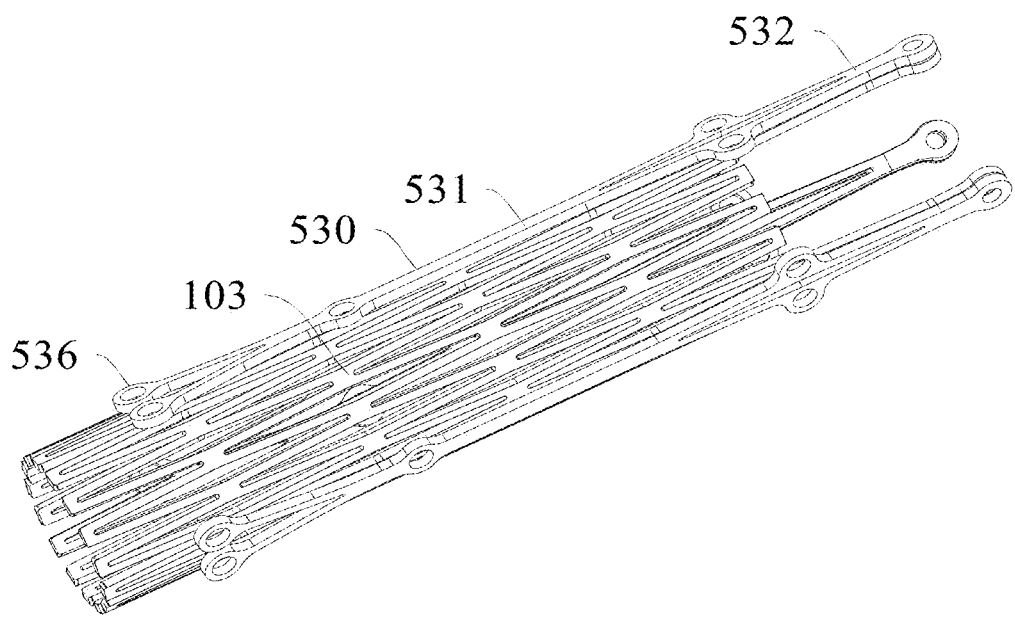
FIG. 31

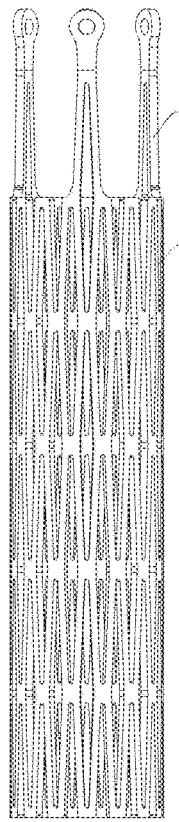 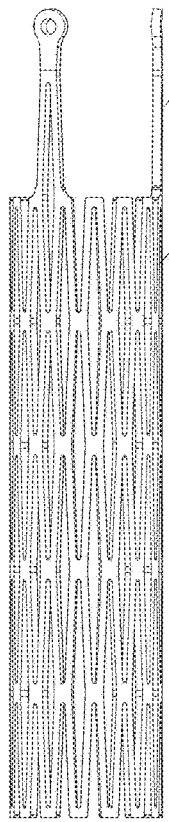 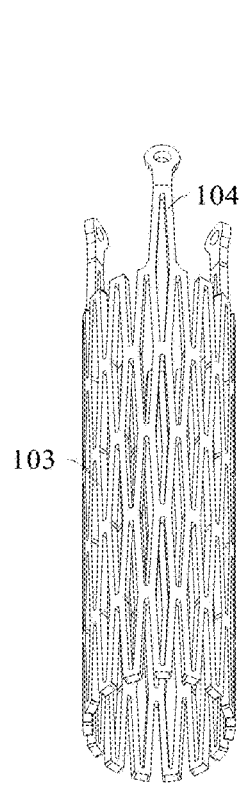 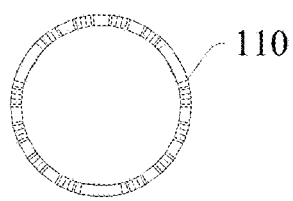
FIG. 36a  FIG. 36b  FIG. 36c  FIG. 36d
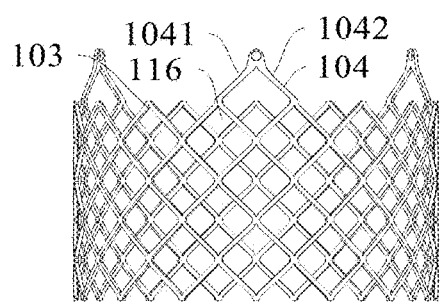 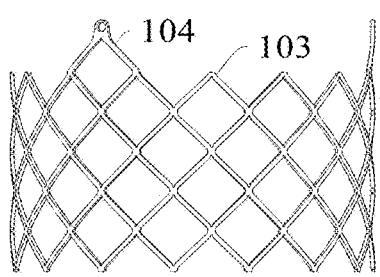
FIG. 37a  FIG. 37b

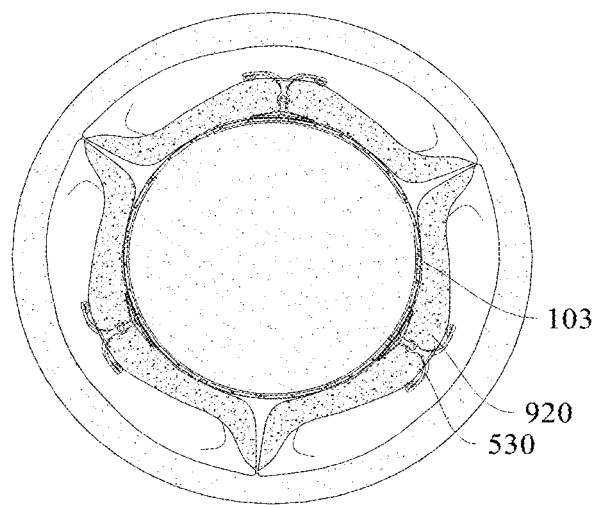
FIG. 39d
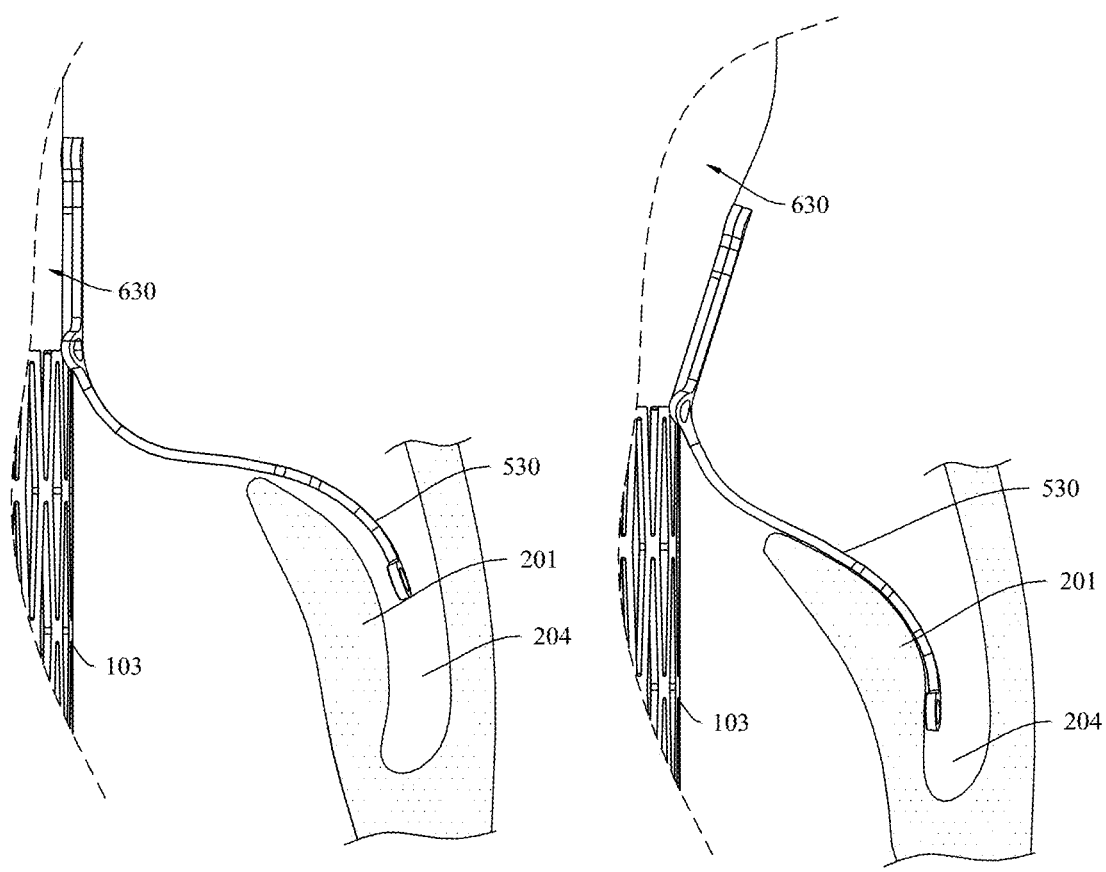
FIG. 40a                    FIG. 40b

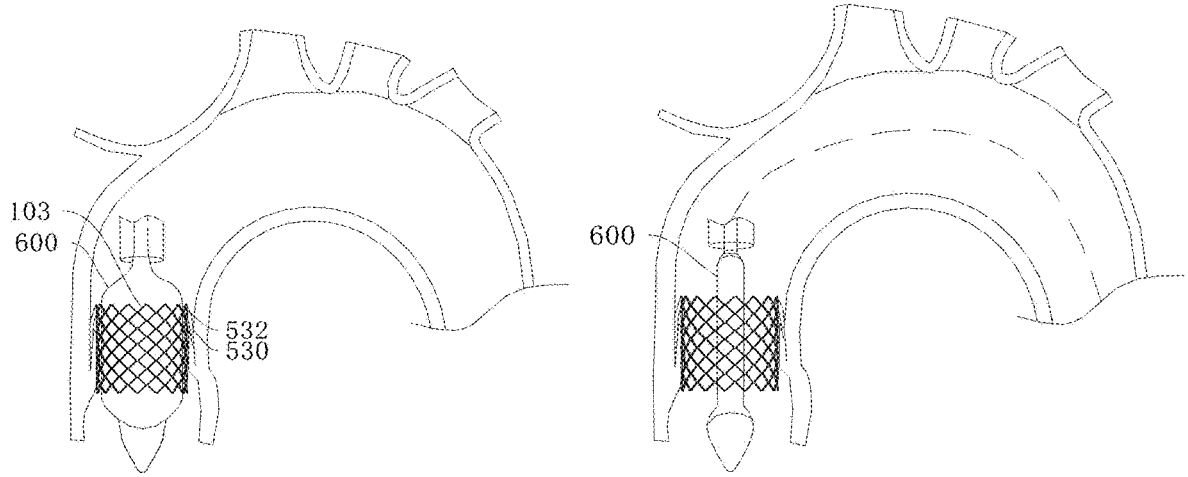

FIG. 61c   FIG. 61d

| Delivering the prosthetic aortic valve device to a predetermined site, during which, the inner frame is in a compressed configuration, the guiding members are in a loaded configuration, and the balloon device is in a deflated configuration | S10 |

↓

| Retracting the outer sheath proximally to expose the wings of the guiding members so that the guiding members are transformed into a transition configuration | S20 |

↓

| Obtaining a position of the guiding members relative to valvular sinus floors, and when the position is misaligned, rotating the support device to drive the inner frame to move synchronously so that the wings of the guiding members are aligned with the valvular sinus floors | S30 |

↓

| Driving the balloon device to an inflated configuration, releasing the inner frame and the roots of the guiding members so that the inner frame is transformed into an expanded configuration, and the guiding members are transformed into a released configuration | S40 |

↓

| Driving the balloon device to an deflated configuration, and withdrawing the system | S50 |

FIG. 62

PROSTHETIC HEART VALVE DEVICE, DELIVERY SYSTEM, INTERVENTIONAL SYSTEM AND RELATED METHOD

TECHNICAL FIELD

The present application relates to the technical field of medical devices, in particular to prosthesis heart valve devices, delivery systems, interventional systems and related methods.

BACKGROUND

The known methods for treating aortic valve calcification or insufficiency include minimally invasive transcatheter surgery. The position of the applied prosthetic heart valve device for implantation in the human body needs to be adjusted during the implantation in the human body in the axial and circumferential directions. The two axial ends of the prosthesis heart valve are respectively the inflow end and the outflow end in the normal blood flow direction, with the interior being the blood flow passage. Taking the aortic valve as an example, the aortic valvular sinuses in the human body have two coronary orifices, and the prosthetic heart valve device should be prevented from blocking the coronary orifices during implantation, after positioning and during operation. Therefore, there are high requirements for the position adjustment of the prosthetic heart valve device in the human body and the engagement thereof with the native valve, especially the circumferential position between the prosthetic heart valve device and the native valve.

SUMMARY

For the positioning of a prosthetic heart valve device in the human body, the present application provides a prosthetic heart valve device including:

- an inner frame having a meshed cylindrical structure which is radially deformable and opposite inflow and outflow ends, an interior of the inner frame being an axially through blood flow passage, the inner frame having relative compressed and expanded configurations;
- leaflets connected to the inner frame and cooperating with each other to control opening and closing of the blood flow passage; and
- a positioning mechanism arranged in a circumferential direction of the inner frame, the positioning mechanism comprising a fixed end connected to the inner frame and a free end extending towards the inflow end, the positioning mechanism being configured to be switchable among the following configurations:
  - a loaded configuration, wherein the inner frame is in the compressed configuration, and the fixed end and the free end of the positioning mechanism contact or are adjacent to the inner frame in a radial direction of the inner frame;
  - a transition configuration, wherein inner frame is in the compressed configuration, while the free end of the positioning mechanism is stretched in a peripheral region of the inner frame, with a first receiving space defined between the free end of the positioning mechanism and an outer wall of the inner frame for allowing entry of native leaflet; and
  - a released configuration, wherein the inner frame is in the expanded configuration, with a second receiving space defined between the free end of the positioning mechanism and the outer wall of the inner frame for clipping the native leaflet.

Optionally, the second receiving space is smaller than the first receiving space in the radial direction of the inner frame.

Optionally, the inner frame is configured to be released and expanded by balloon, and the positioning mechanism is configured to be released by self-expanding Optionally, the inner frame has a straight cylindrical shape.

Optionally, the outflow end of the inner frame is flared in the expanded configuration.

Optionally, the flared angle of the outflow end of the inner frame relative to an axial direction of the inner frame is defined as P4, and P4 meets 0 degrees<P4≤45 degrees. Preferably, P4 is ranged from 5 degrees to 25 degrees.

Optionally, the prosthetic heart valve device is a prosthetic aortic valve device.

Optionally, the positioning mechanism includes a plurality of groups of clipping arms, one end of each clipping arm connected to the inner frame is the fixed end, and the other end is the free end opposite to the fixed end.

Optionally, in the transition configuration, the fixed ends of the clipping arms are gathered together and adjacent to or contact the inner frame; and in the released configuration, the fixed ends of the clipping arms move away from each other as the inner frame is released.

Optionally, the clipping arms in each group comprise at least two clipping arms, and wherein the fixed ends of the at least two clipping arms in each group are adjacent to each other, while the free ends of the at least two clipping arms in each group tend to be away from each other.

Optionally, the free ends of at least two clipping arms in adjacent groups tend to be close to each other.

Optionally, the inner frame has at least two commissure regions corresponding to the respective coaptation portions of adjacent leaflets, and the fixed ends of the clipping arms in each group are connected to the respective commissure region.

Optionally, in the loaded configuration, the inner frame and all the clipping arms do not radially overlap each other.

Optionally, the commissure region comprises a commissure post, a pulling arm is connected between adjacent commissure posts, a first avoidance space is defined between the pulling arm and the outflow end of the inner frame, and the clipping arms are located within the respective first avoidance spaces in the loaded configuration.

Optionally, the pulling arm is configured as a single rod structure or a deformable meshed strip.

Optionally, each group of clipping arms is configured as a separate member connected to the inner frame.

Optionally, a connection portion of each group of clipping arms with the inner frame is a root, a portion of each group of clipping arms extending from the root towards the inflow end is a wing; and the root is fixed on an outside of the inner frame by binding.

Optionally, the root comprises a first frame bar and a second frame bar, the wing comprise a third frame bar and a fourth frame bar adjacent to the root, and wherein the first frame bar, the second frame bar, the third frame bar, and the fourth frame bar form a quadrangle; and ends of the third frame bar and the fourth frame bar away from the root meet and then is split into branches until to the free ends, where the branches split belong to different clipping arms and correspond to different valvular sinuses.

Optionally, the inner frame has at least two commissure regions corresponding to the respective coaptation portions of adjacent leaflets, and one or more clipping arms are connected at the same side of the commissure region in the circumferential direction of the inner frame.

Optionally, the meshed strip is a deformable structure in an extension direction of the clipping arm.

Optionally, the clipping arm has a wavy structure adjacent the free end.

Optionally, the fixed ends of the clipping arms in each group meet at a connecting portion and are fixed to the inner frame through the connecting portion; and the connecting portion corresponding to each group of clipping arms is formed in one piece or by separate pieces adjacent to each other.

Optionally, each group of clipping arms includes pairs of clipping arms, the clipping arms in each pair are located at two sides of the connecting portion in the circumferential direction of the inner frame, and the stretched clipping arms in different pairs have different lengths.

Optionally, the fixed ends of the clipping arms in each group meet at a connecting portion and are fixed to the inner frame through the connecting portion;

Each group of clipping arms includes pairs of clipping arms, the clipping arms in each pair are located at two sides of the connecting portion in the circumferential direction of the inner frame, and in the released configuration, the clipping arms located at the same side of the connecting portion, but from different pairs have different extensions.

Optionally, in the released configuration, the free ends of the clipping arms in each group are in the same position or offset from each other in the radial direction of the inner frame; and in the released configuration, the free ends of all the clipping arms are located between the inflow end and the outflow end of the inner frame in an axial direction of the inner frame and adjacent to the inflow end of the inner frame.

Optionally, the fixed ends of the clipping arms in each group meet at a connecting portion, and are fixed to the inner frame through the connecting portion; the inner frame has at least two commissure regions corresponding to the respective coaptation portions of adjacent leaflets, and the connecting portion is fixed to the commissure region of the inner frame by welding or by a connecting member; and in the radial direction of the inner frame, the connecting portion is overlapped on an outside of the commissure region, or in the circumferential direction of the inner frame, the connecting portion is on a side of the commissure region.

Optionally, the prosthetic heart valve device further comprises:
 a connecting ring fixed with the outflow end of the inner frame and provided with a plurality of connecting regions at intervals; and
 the clipping arms are located around an outer periphery of the inner frame and include groups of clipping arms provided at intervals along the circumferential direction of the inner frame, each of the clipping arms has opposite fixed end and free end, and the fixed ends of clipping arms in each group are located within the same connecting region.

Optionally, the connecting ring and the clipping arms are formed by winding wires.

Optionally, the fixed end of each clipping arm extends in the circumferential direction of the inner frame, and the clipping arm satisfies at least one of the following conditions relative to an axis of the inner frame:
 a circumferential distribution region M1 of the fixed end has a central angle with respect to the axis of the inner frame being greater than 15 degrees; and
 an axial distribution region M3 of the clipping arm has a length with respect to the axis of the inner frame being greater than 5 mm.

Optionally, a circumferential distribution region M4 of the fixed ends of the clipping arms in each group has a central angle with respect to the axis of the inner frame being equal to or less than 360/n, where n is the number of the leaflets.

Optionally, the circumferential distribution region M1 of the fixed end of the single clipping arm has a central angle with respect to the axis of the inner frame being equal to or less than 360/2n, where n is the number of the leaflets.

Optionally wherein, each clipping arm comprises an enlarged positioning structure; and the positioning structure is located at the free end of the respective clipping arm and enlarged by extension of material of the clipping arm itself, or the positioning structure is located on a side of the clipping arm extending from the fixed end to the free end.

Optionally, each clipping arm is covered with a sleeve which has a braided structure or is formed in one piece.

Optionally, in the loaded configuration, the clipping arms in each group are close to each other and surround an outer periphery of the inner frame; and the clipping arms do not overlap each other in the radial direction of the inner frame.

Optionally, the positioning mechanism comprises guiding members arranged sequentially in the circumferential direction of the inner frame, and wherein a connection portion of each guiding member with the inner frame is a root, and a portion of each guiding member extending from the root towards the inflow end is a wing; and the guiding members are aligned with the respective leaflets in the circumferential direction of the inner frame.

Optionally, the inner frame has at least two commissure regions corresponding to the respective coaptation portions of adjacent leaflets, and the root of each guiding member is located between two commissure regions in the circumferential direction of the inner frame.

Optionally, in the released configuration, the guiding member extends outward from the root and is bent inward in the radial direction of the inner frame.

Optionally, each of the guiding members is formed in one piece and switches the configurations based on its own elastic deformation; and each of the guiding members is made of a memory alloy and preset by heat treatment in advance, and after the heat treatment, the guiding member has a shape corresponding to the released configuration, and the guiding member has internal stress in both the loaded configuration and the transition configuration relative to the released configuration.

Optionally, the wing has a branched structure adjacent to the root, and the branched structure is opened towards the outflow end.

Optionally, a portion of the wing adjacent the free end is split in the circumferential direction of the inner frame.

Optionally, a portion of the wing adjacent the free end is split in the circumferential direction of the inner frame; and the portion of the wing adjacent the free end is split into at least two branches.

Optionally, the free end is annular and covered with a protective layer; and the free end is provided with a first eyelet, the wing is provided with a second eyelet at a position precede to be split, and both the first eyelet and the second eyelet are provided with radiopaque markers.

Optionally, in the released configuration, the free end of the wing is adjacent to or against the outer wall of the inner frame.

Optionally, the free end of each wing has a span corresponding to a central angle of 30 to 60 degrees in the circumferential direction of the inner frame.

Optionally, an angle between the wing and an axis of the inner frame in the transition configuration is P1, an angle between the wing and the axis of the inner frame in the released configuration is P2, and P1 is greater than P2.

Optionally, the root of the guiding member has a span with respect to the circumferential direction of the inner frame being ranged from 15 to 45 degrees; and the inner frame has a plurality of axially distributed cells, and the root of the guiding member has a span with respect to the circumferential direction of the inner frame corresponding to one or more cells.

Optionally, the root is always in abutment with the inner frame in all of the configurations of the guiding member;

The root is in abutment with a radially inner side or a radially outer side of the inner frame or is radially aligned with the inner frame.

Optionally, the root has a circumferential deformation between the transition configuration and the released configuration.

Optionally, the connection portion of the positioning mechanism with the inner frame is a root, and a portion of the positioning mechanism extending from the root towards the inflow end is a wing;

The root and a connection portion of the wing with the root form as a frame structure, wherein two ends of the frame structure in the circumferential direction of the inner frame are configured to move relative to each other and two ends of the frame structure in an axial direction of the inner frame are configured to be turned over as the inner frame is compressed.

Optionally, when the two ends of the frame structure in the circumferential direction of the inner frame move relative to each other as the inner frame is compressed, the two ends of the frame structure in the circumferential direction of the inner frame move away from each other, or close to each other, or are turned over relative to an axis of the inner frame in opposite directions, respectively.

Optionally, when the two ends of the frame structure in the axial direction of the inner frame are turned over relative to each other, one end at the root thereof is fixed relative to the inner frame, and the other end is turned over relative to the outer wall of the inner frame.

Optionally, when the two ends of the frame structure in the circumferential direction of the inner frame are turned over relative to each other, both ends are turned over with respect to the outer wall of the inner frame.

Optionally, when the two ends of the frame structure in the axial direction of the inner frame are turned over relative to each other, the root remains in contact with or adjacent to the inner frame, while the wing is turned over.

Optionally, in the frame structure:
in the transition configuration, an angle is formed between the root and the wing and defined as Q1;
in the released configuration, an angle is formed between the root and the wing and defined as Q2; and
Q1 is smaller than Q2, and the angle is an angle of the frame structure formed at an outer side of the inner frame.

Optionally, the frame structure encloses a closed region or a semi-closed region that is opened toward the outflow end.

Optionally, the root comprises a first frame bar and a second frame bar, both of which can be twisted about their own longitudinal axes relative to the inner frame;

The first frame bar and the second frame bar are bound to the inner frame, one end of the first frame bar and one end of the second frame bar are spaced apart from each other and connected to the wing, while the other end of the first frame bar and the other end of the second frame bar are fixed to the inner frame at the outflow end of the inner frame.

Optionally, the end of the first frame bar and the end of the second frame bar away from the wing are intersected with, parallel to or away from each other, and the intersection of the first frame bar and the second frame bar are provided with a wire binding eyelet.

Optionally, connecting posts are provided and axially extended from the outflow end of the inner frame, the root is fixed to the respective connecting post, and the connecting post and the root have the same shape and overlap each other in the radial direction of the inner frame.

Optionally, the connecting post is V-shaped with a tip of the V-shape directed to the outflow end.

Optionally, the root comprises a first frame bar and a second frame bar, and wherein one end of the first frame bar and one end of the second frame bar are spaced apart from each other and connected to the wing, while the other end of the first frame bar and the other end of the second frame bar are fixed to the inner frame, and the wing comprises, adjacent the root:
a third frame bar, one end of which is connected with the first frame bar, and the other end of which extends towards the inflow end; and
a fourth frame bar, one end of which is connected with the second frame bar, and the other end of which extends towards the inflow end and intersects with the third frame bar;
and wherein the first frame bar, the second frame bar, the third frame bar, and the fourth frame bar form as a frame structure; and
at least one of the four frame bars is configured to be twisted about its own longitudinal axis when switching from the transition configuration to the released configuration.

Optionally, the first frame bar, the second frame bar define a first portion, and the third bar and the fourth bar define a second portion;
In the transition configuration, an angle between the first portion and the second portion is Q1;
In the released configuration, an angle between the first portion and the second portion is Q2;
Q1 is smaller than Q2, and the angle is an angle formed at an outer side of the inner frame.

Optionally, the third frame bar and the first frame bar have a first connection point therebetween, and the fourth frame bar and the second frame bar have a second connection point therebetween, and the first connection point and the second connection point are distant from each other when switching from the transition configuration to the released configuration, and an angle between the third frame bar and the first frame bar and an angle between the second frame bar and the fourth frame bar are substantially unchanged.

Optionally, the guiding member is provided with restricting structures provided at the first connection point and the second connection point, and the first connection point and the second connection point are bound to the inner frame by means of the restricting structures.

Optionally, the guiding member has opposite outer side and inner side in the circumferential direction of the inner frame, and the wing has a smooth contour at the outer side of the guiding member, which extends from the root to the inflow end and is offset towards the inner side.

Optionally, in the released configuration, the free ends of the two wings of the guiding member are spaced apart from each other, and the spacing region has a span corresponding to a central angle, in the circumferential direction of the inner frame, which is greater than 30 degrees.

Optionally, the free end has a planar structure, and in the transition configuration, the free ends of the two wings of the individual guiding member define a first reference plane and a second reference plane, respectively, and an angle between the first reference plane and the second reference plane is less than or equal to 90 degrees.

Optionally, the free end has an annular structure.

Optionally, the inner frame has at least two commissure regions corresponding to the respective coaptation portions of adjacent leaflets and provided sequentially in the circumferential direction of the inner frame, a spacing region is defined between two adjacent commissure regions in an outer peripheral region of the inner frame, and the positioning mechanism avoids the spacing region.

Optionally, the positioning mechanism is formed by separate positioning members which are independent from each other, and each positioning member is directly connected to at most one commissure region.

Optionally, the inner frame has at least two commissure regions corresponding to the respective coaptation portions of adjacent leaflets and configured as commissure posts extending from the outflow end of the inner frame; and an end of the commissure post is provided with a first collar, and an edge of the inner frame at the inflow end is provided with a second collar aligned with the first collar.

The present application further provides a delivery system for a prosthetic heart valve device, which is configured for loading and delivering the prosthetic heart valve device, the delivery system has opposite distal and proximal ends and comprises:
 a balloon device switchable between an inflated configuration and a deflated configuration under an action of a fluid;
 an outer sheath which is slidably engaged on an outer periphery of the balloon device, with a radial gap between the outer sheath and the balloon device being configured as a loading zone for receiving the compressed prosthetic aortic valve device; and
 a control handle, wherein both proximal ends of the balloon device and the outer sheath extend to the control handle with the outer sheath slidably engaged with the control handle.

Optionally, the balloon device comprises:
 a tube having at least a guidewire channel and an injection channel provided therein, a proximal end of the tube being rotatably arranged to the control handle;
 a guiding head fixed with a distal end of the tube, a distal end of the guidewire channel being opened into the guiding head; and
 a balloon fixed with the tube and located at a proximal end of the guiding head, an interior of the balloon being communicating with the injection channel.

Optionally, the tube has a multi-layer structure from an inside to an outside, with a middle layer being a hypotube or a steel cable tube, and wherein the steel cable tube has multiple layers, with two layers thereof coiled in opposite directions.

Optionally, the control handle comprises:
 a support;
 a movable base movably arranged on the support, to which a proximal end of the outer sheath is fixed;
 a driving sleeve rotatably arranged on an outer periphery of the support and engaged with the movable base in a transmission manner for driving the outer sheath to slide relative to the balloon device; and
 a rotatable seat rotatably arranged on the outer periphery of the support and engaged with the tube of the balloon device for driving the balloon device to rotate relative to the outer sheath.

The present application further provides an interventional system comprising:
 the prosthetic heart valve device; and
 the delivery system for the prosthetic heart valve device.

The present application further provides an interventional system comprising:
 a prosthetic heart valve comprising an inner frame and positioning mechanism and leaflets respectively connected with the inner frame; and
 a delivery system comprising a balloon device, an outer sheath slidably engaged on an outer periphery of the balloon device, and a control handle connected with the balloon device and the outer sheath, wherein the prosthetic heart valve is loadable in a radial gap between the balloon device and the outer sheath, and wherein
 the control handle is provided with a rotatable seat for controlling rotation of the balloon device so that the positioning mechanism can be aligned with valvular sinus.

Optionally, the delivery system is configured to enter the human body via a femoral artery.

Optionally, the positioning mechanism is arranged in a circumferential direction of the inner frame and the positioning mechanism includes a fixed end connected to the inner frame and a free end extending towards the inflow end, the positioning mechanism is configured to be switchable among the following configurations:
 a loaded configuration, wherein the inner frame is in the compressed configuration, and the fixed end and the free end of the positioning mechanism contact or are adjacent to the inner frame in a radial direction of the inner frame;
 a transition configuration, wherein inner frame is in the compressed configuration, while the free end of the positioning mechanism is stretched in a peripheral region of the inner frame, with a first receiving space defined between the free end of the positioning mechanism and an outer wall of the inner frame for allowing entry of native leaflet; and
 a released configuration, wherein the inner frame is in the expanded configuration, with a second receiving space defined between the free end of the positioning mechanism and the outer wall of the inner frame for clipping the native leaflet.

Optionally, the second receiving space is smaller than the first receiving space in the radial direction of the inner frame.

Optionally, the inner frame is configured to be released and expanded by balloon, and the positioning mechanism is configured to be released by self-expanding.

Optionally, the positioning mechanism includes a plurality of groups of clipping arms, one end of each clipping arm connected to the inner frame is a fixed end, and the other end is a free end opposite to the fixed end.

Optionally, the clipping arms in each group comprise at least two clipping arms, and wherein the fixed ends of the at least two clipping arms in each group are adjacent to each other, while the free ends of the at least two clipping arms in each group tend to be away from each other.

Optionally, the free ends of at least two clipping arms in adjacent groups tend to be close to each other.

Optionally, each group of clipping arms is configured as a separate member connected to the inner frame.

Optionally, the positioning mechanism includes guiding members arranged sequentially in the circumferential direction of the inner frame, and wherein a connection portion of each guiding member with the inner frame is a root, and a portion of each guiding member extending from the root towards the inflow end is a wing; and The guiding members are aligned with the respective leaflets in the circumferential direction of the inner frame.

Optionally, the inner frame has at least two commissure regions corresponding to the respective coaptation portions of adjacent leaflets, and the root of each guiding member is located between two commissure regions in the circumferential direction of the inner frame.

Optionally, in the released configuration, the guiding member extends outward from the root and is bent inward in the radial direction of the inner frame.

The present application further provides a method for using the interventional system, comprising:
- delivering the prosthetic heart valve device to a predetermined site, during which, the inner frame is in a compressed configuration, the positioning mechanism is in a loaded configuration, and the balloon device is in a deflated configuration;
- retracting the outer sheath proximally to expose a part of the positioning mechanism so that the positioning mechanism is transformed into a transition configuration;
- obtaining a position of the positioning mechanism relative to sinus floor of valvular sinus, and when the position is misaligned, rotating the balloon device to drive the inner frame to move synchronously so that the positioning mechanism is aligned with the sinus floor; and
- driving the balloon device to an inflated configuration, releasing the inner frame and the positioning mechanism so that the inner frame is transformed into an expanded configuration, and the positioning mechanism is transformed into a released configuration.

The present application further provides a method for securing the prosthetic heart valve device at an aortic annulus with native leaflets, comprising:
- delivering the prosthetic heart valve device to a predetermined site, during which, the inner frame is in a compressed configuration, the positioning mechanism is in a loaded configuration, and the balloon device is in a deflated configuration;
- retracting the outer sheath proximally to expose a part of the positioning mechanism so that the positioning mechanism is transformed into a transition configuration;
- obtaining a position of the positioning mechanism relative to sinus floor of valvular sinus, and when the position is misaligned, rotating the balloon device to drive the inner frame to move synchronously so that the positioning mechanism is aligned with the sinus floor; and
- driving the balloon device to an inflated configuration, releasing the inner frame and the positioning mechanism so that the inner frame is transformed into an expanded configuration, and the positioning mechanism is transformed into a released configuration.

The present application further provides a prosthetic heart valve device having opposite inflow and outflow ends, the prosthetic heart valve device comprising:
- an inner frame, having a meshed cylindrical structure which is radially deformable and having relative compressed and expanded configurations, an interior of the inner frame being an axially through blood flow passage;
- leaflets connected to the inner frame and cooperating with each other to control opening and closing of the blood flow passage; and
- positioning mechanism arranged in a circumferential direction of the inner frame, the positioning mechanism comprising a root connected with the inner frame and a wing extending from the root towards an inflow end, the wing is stretchable within a peripheral region of the inner frame, with a receiving space defined between the wing and an outer wall of the inner frame for entry of native leaflet, wherein the root and a connection portion of the wing with the root form as a frame structure, and wherein two ends of the frame structure in the circumferential direction of the inner frame are configured to move relative to each other and two ends of the frame structure in an axial direction of the inner frame are configured to be turned over as the inner frame is compressed.

Optionally, a plurality of positioning members are included, each of which is connected to the inner frame as a separate member.

The present application further provides a prosthetic heart valve device having opposite inflow and outflow ends, the prosthetic heart valve device comprising:
- an inner frame, having a meshed cylindrical structure which is radially deformable and having relative compressed and expanded configurations, an interior of the inner frame being an axially through blood flow passage;
- leaflets connected to the inner frame and cooperating with each other to control opening and closing of the blood flow passage; and
- a positioning mechanism, the positioning mechanism comprising a root connected with the inner frame and a wing extending from the root towards an inflow end, the wing is stretchable within a peripheral region of the inner frame, with a receiving space defined between the wing and an outer wall of the inner frame for entry of native leaflet, wherein the positioning mechanism comprises separate positioning members arranged in sequence in a circumferential direction of the inner frame, and the separate positioning members are indirectly connected to each other only through the inner frame.

Optionally, the inner frame is configured to be released and expanded by balloon, and the positioning mechanism is configured to be released by self-expanding.

Optionally, each of the positioning members comprises a group of clipping arms; one end of each clipping arm connected to the inner frame is a fixed end, and the other end is an opposite free end; and each group of clipping arms comprises at least two clipping arms, with the fixed ends thereof being adjacent to each other, and the free ends of at least two clipping arms in each group tend to be away from each other.

Optionally, the inner frame has commissure regions corresponding to the respective coaptation portions of adjacent leaflets, and connection portions of the groups of clipping arms with the inner frame are circumferentially aligned with the respective commissure regions;

There are at least two clipping arms corresponding to the same leaflet in the circumferential direction of the inner frame and belonging to different groups, and the free ends of the clipping arms from different groups are spaced apart from each other and tend to be close to each other.

Optionally, each group of clipping arms is connected to the inner frame as a separate member.

The present application further provides a prosthetic heart valve device having opposite inflow and outflow ends, the prosthetic heart valve device comprising:

an inner frame, having a meshed cylindrical structure which is radially deformable and having relative compressed and expanded configurations, an interior of the inner frame being an axially through blood flow passage;

leaflets connected to the inner frame and cooperating with each other to control opening and closing of the blood flow passage; and a positioning mechanism stretchable within a peripheral region of the inner frame, with a receiving space defined between the positioning mechanism and an outer wall of the inner frame for entry of native leaflet, the inner frame having commissure regions corresponding to the respective coaptation portions of adjacent leaflets, the positioning mechanism being arranged in a circumferential direction of the inner frame, with connection portions with the inner frame, each connection portion being located between two adjacent commissure regions in the circumferential direction of the inner frame.

Optionally, the positioning mechanism comprises guiding members, the guiding member including a root connected with the inner frame and a wing extending from the root towards an inflow end;

The root of each guiding member is located between two adjacent commissure regions in the circumferential direction of the inner frame.

Optionally, the guiding member is connected to the inner frame as a separate member.

The present application further provides a prosthetic heart valve device having opposing inflow and outflow ends, the prosthetic heart valve device comprising:

an inner frame, having a meshed cylindrical structure which is radially deformable and having relative compressed and expanded configurations, an interior of the inner frame being an axially through blood flow passage;

leaflets connected to the inner frame and cooperating with each other to control opening and closing of the blood flow passage; and positioning mechanism arranged in a circumferential direction of the inner frame, the positioning mechanism comprising a root connected with the inner frame and a wing extending from the root towards an inflow end, the wing is stretchable within a peripheral region of the inner frame, with a receiving space defined between the wing and an outer wall of the inner frame for entry of native leaflet, wherein the inner frame has commissure regions corresponding to the respective coaptation portions of adjacent leaflets, the root is located between two commissure regions in the circumferential direction, the wing has a free end away from the root, and a portion of the wing adjacent the free end is split in the circumferential direction of the inner frame.

In the present invention, the prosthesis heart valve device is structurally improved, where the positioning mechanism and the inner frame clip the native valve leaflets or abut against the valvular sinus floors for axial positioning or circumferential alignment, preventing displacement of the prosthetic heart valve device under the action of blood flow. Specific advantageous technical effects will be further explained in connection with specific structures or steps in specific embodiments.

BRIEF DESCRIPTION OF THE DRAWINGS

FIG. 3a illustrates the engagement between the clipping arm and the inner frame in a side view;

FIG. 3b illustrates the engagement between the clipping arm and the native leaflet;

FIG. 4a to FIG. 4d illustrate different examples of the clipping arms in a side view, respectively;

FIG. 7 is a perspective view of a frame of a prosthetic heart valve device according to another embodiment;

FIGS. 8 to 11 illustrate the engagement of the fixed end of the clipping arm and the commissure post, respectively;

FIG. 29 is a front view of the prosthetic aortic valve device in a loaded configuration in one embodiment;

FIG. 30 is a front view of the prosthetic aortic valve device in a transition configuration in one embodiment;

FIG. 31 is a perspective view of the prosthetic aortic valve device of FIG. 29;

FIG. 33b is a left side view of the prosthetic aortic valve device of FIG. 33a;

FIG. 33c is a perspective view of the prosthetic aortic valve device of FIG. 33a;

FIG. 35b is a left side view of the prosthetic aortic valve device of FIG. 35a;

FIGS. 36a to 36d are respectively a front view, a left side view, a perspective view and a top view of the inner frame of the prosthetic aortic valve device in a compressed configuration;

FIGS. 37a-37d are respectively a front view, a left side view, a perspective view and a top view of the inner frame of the prosthetic aortic valve device in an expanded configuration;

FIG. 39d is a view showing the engagement between the prosthetic aortic valve device and the aortic valve;

FIG. 40a illustrates the guiding member after placement in the valvular sinus and before engagement;

FIG. 40b illustrates the deformation of the guiding member at the initial stage of release;

FIG. 47 is a top view of FIG. 28a;

FIGS. 60a-61d are views showing the release process of the prosthetic aortic valve device;

FIG. 62 is a flow chart of a method for using an interventional system according to an embodiment of the present application.

FIG. 70b is an enlarged view of part C of FIG. 70a;

FIG. 75 is a perspective view of a prosthetic aortic valve device of another embodiment;

FIGS. 76 and 77 are perspective views showing spacing regions of a prosthetic aortic valve device in different configurations.

Figure 1A:
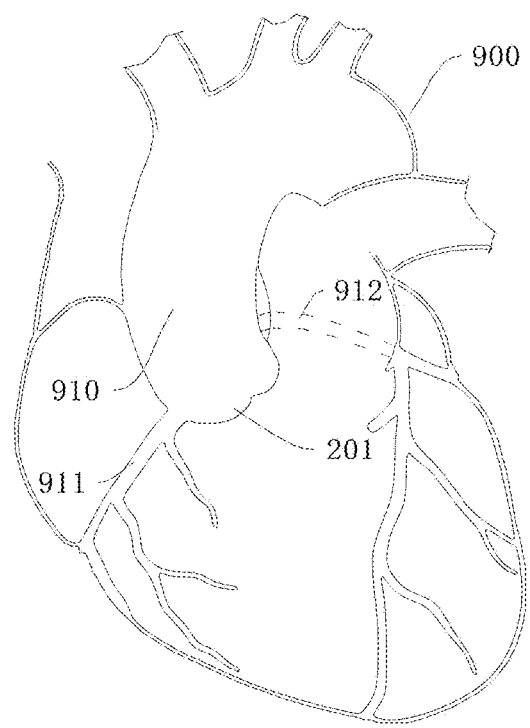
FIG. 1a is a schematic view showing the aorta and coronary artery in the heart.

LIST OF REFERENCE NUMERALS 100, prosthetic heart valve device; 1000, prosthetic aortic valve device; 101, inflow end; 102, outflow end; 103, inner frame; 104, connecting post; 1041, fifth bar; 1042, sixth bar; 110, frame; 111, spacing region; 1112, eyelet; 114, commissure region; 115, first collar; 116, cell; 117, second collar; 120, clipping arm; 121, fixed end; 1221, rounded structure; 123, free end; 127, commissure region; 129, projection area; 132, commissure post, 141, leg, 142, pulling arm, 146, apex, 160, first avoidance space, 168, deformable slot, 173, radiopaque point;

200, leaflet; 201, native leaflet; 204, valvular sinus; 211, joining region; 220, covering film; 221, inner covering film; 223, outer covering film;

301, blood flow passage; 310, connecting portion; 3101, radiopaque hole; 311, positioning structure; 3120, sleeve; 313, rigid portion; 314, flexible portion; 315, connecting member; 321, unit; 330, wave structure; 340, connecting ring; 341, a connecting region, 342, a second avoidance space, 343, a first position, 344, a second position, 345, a flexible member;

400, delivery system; 404, support device; 405, outer sheath; 406, loading zone; 407, control handle; 410, support; 411, sliding groove; 420, movable base; 430, driving sleeve; 440, rotatable seat; 441, planetary carrier; 442, planetary gear; 443, ring gear; 444, planetary input shaft; 445, planetary output shaft; 451, worm wheel; 452, worm; 453, transmission sleeve; 454, support base; 461, first gear; 462, second gear; 463, transmission sleeve; 464, support base;

530, guiding member; 531, wing; 531a, wing; 531b, wing; 531c, wing; 531d, wing; 531e, wing; 531f, wing; 532, root; 532a, root; 532b, root; 5321, first bar; 5322, second bar; 5323, first binding eyelet; 5324, first connection point; 5325, second connection point; 5326, third connection point; 5327, first plane; 5311, first wing; 5312, second wing; 534, free end; 5341, wave structure; 535, branched structure; 5351, third bar; 5352, fourth bar; 5353, slot; 5354, second binding eyelet; 5355, fourth connection point; 5356, second plane; 536, free end; 5361, seventh bar; 5362, eighth bar; 537, restricting structures; 538, first portion; 539, second portion; 550, radiopaque marker; 550a, radiopaque marker; 550b, radiopaque marker; 550c, radiopaque marker; 551, eyelet;

600, balloon device; 610, tube; 6101, outermost layer; 6102, middle layer; 6103, innermost layer; 620, guiding head; 630, balloon;

900, human heart; 910, aorta; 911, right coronary artery trunk; 912, left coronary artery trunk.

DESCRIPTION OF THE EMBODIMENTS

The technical solutions according to the embodiments of the present disclosure will be described clearly and fully in combination with the drawings according to the embodiments of the present disclosure. Obviously, the described embodiments are not all embodiments of the present disclosure, but only part of the embodiments of the present disclosure. Based on the disclosed embodiments, all other embodiments obtained by those skilled in the art without creative work fall into the scope of this invention.

It should be noted that, when a component is "connected" with another component, it may be directly connected to another component or may be indirectly connected to another component through a further component. When a component is "provided" on another component, it may be directly provided on another component or may be provided on another component through a further component.

Unless otherwise defined, all technical and scientific terms used herein have the same meaning as commonly understood by a person skilled in the art. The terms in the description of the present disclosure are used to describe specific embodiments, and not to limit the present disclosure. The term "and/or" used herein includes one or more of the listed options in any combinations, or the combination of all of the listed options.

In the present application, the terms "first", "second" and the like are used for descriptive purposes only and are not to be understood as indicating or implying the relative importance or the number or order of the technical features referred. Thus, features defined with "first", "second" can explicitly or implicitly include one or more of such features. In the description of the present invention, "plurality" means at least two, such as two, three, etc., unless explicitly and specifically defined otherwise.

In this application, the terms "corresponding", "matched", "adapted" and the like, for example, "B corresponding to A," "A corresponding to B," indicate that B corresponds to A in shape, position or function, and B can be determined from A. However, determining B from A does not mean determining B from A alone, but can also be determined from A and/or other information.

Figure 1B:
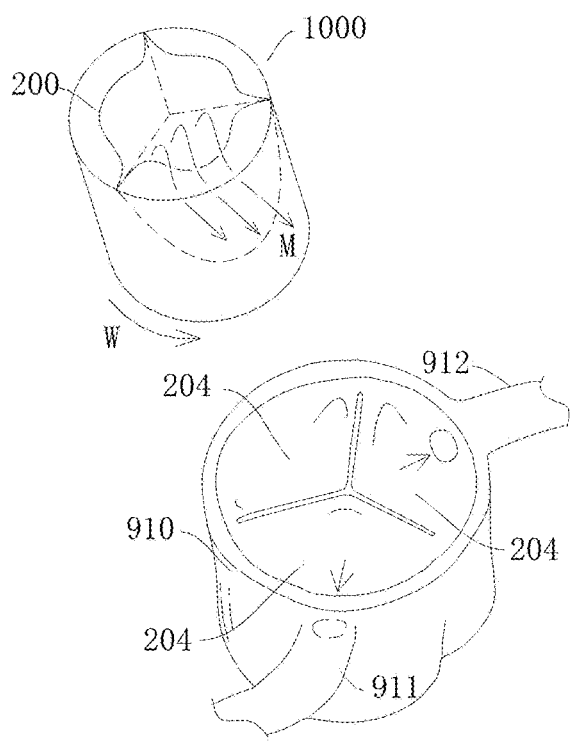
FIG. 1b is a schematic view showing the circumferential positional relationship between the prosthetic aortic valve and the aortic valve.

Referring to FIGS. 1a-1b, the aorta 910 of the human heart 900 has native tricuspid leaflets 201. Valvular sinuses 204 are located between the leaflets and the vessel wall, with two of the valvular sinuses communicating the right coronary artery trunk 911 and the left coronary artery trunk 912, respectively. The prosthetic aortic valve device 1000 should be placed to ensure that blood flowing out through the orifice of the leaflets 200 enters one of the coronary artery trunks in the direction M. Therefore, if there is a position deviation for the prosthetic aortic valve device 1000 in the circumferential direction, the prosthetic aortic valve device 1000 should be adjusted. For example, as shown in FIG. 1b, the prosthetic aortic valve device 1000 can be rotated in direction W such that blood can enter the left coronary artery trunk 912 in direction M.

The frame of the prosthetic heart valve device and the prosthetic heart valve device hereinafter have different configurations in different applications. The frame mainly includes an inner frame and a positioning mechanism such as clipping arms or guiding members, wherein the inner frame has relative compressed and expanded configurations, and the positioning mechanism has loaded configuration, transition configuration and released configuration. Unless otherwise specified, the description related to the proportional relationship of the parts of the frame and the structure of the frame refers to the free condition of the frame outside the human body without force from surrounding tissue, for example, the expanded configuration for the inner frame, and the released configuration for the positioning mechanism.

Referring to FIGS. 1c to 13, the present application discloses a prosthetic heart valve device, including a frame 110 and leaflets although the figures only show the frame. The frame 110 includes an inner frame 103 having a meshed cylindrical structure that is radially deformable and has an axis, a circumferential direction around the axis, and two axial ends being an inflow end 101 and an outflow end 102, the inner frame 103 has relative compressed and expanded configurations depending on the radial deformation, with a blood flow passage extending axially through the inner frame 103, and a support device (e.g., a balloon device) for driving the inner frame 103 to transform into the expanded configuration can be placed within the inner frame 103.

When leaflets are arranged, the leaflets are connected to the inner frame and cooperate with each other to control opening and closing of the blood flow passage. The meshed cylindrical structure of the inner frame 103 is provided with a positioning mechanism. In this embodiment, the positioning mechanism is configured as clipping arms 12. A plurality of groups of clipping arms 120 are located at an outer periphery of the inner frame 103 and spaced apart from each other in the circumference of the frame 110, each clipping arm 120 having opposite fixed end 121 and free end 123, the fixed end 121 being directly or indirectly connected with the inner frame 103, the other end extending towards the inflow end to the free end 123. During the use of the prosthetic heart valve device, the clipping arm 120 can transform among various configurations of:

a loaded configuration, in which the inner frame 103 assumes the compressed configuration, and the clipping arms 120 contact or are adjacent to the inner frame 103 in the compressed configuration;

during release, the clipping arms 120 are located outside the inner frame 103, and thus can be released prior to the inner frame 103, thereby transforming into the transition configuration;

in the transition configuration, the inner frame 103 is in the compressed configuration, and the ends of the clipping arms 120 as the positioning mechanism connected to the inner frame 103 remain compressed along with the inner frame 103 to adapt to the inner frame 103 in the compressed configuration. That is, the fixed ends of the clipping arms 120 are gathered together and remain in contact with or close to the inner frame 103, while the free ends of the clipping arms 120 extending towards the inflow end are stretched in the outer peripheral region of the inner frame 103, with a first receiving space defined between the clipping arms 120 and the outer wall of the inner frame for allowing the native leaflets to enter therein. As the inner frame 103 is released, the clipping arms 120 transform into the released configuration; and in the released configuration, the inner frame 103 is in the expanded configuration, the ends of the clipping arms 120 connected to the inner frame 103 move away from each other to adapt to the inner frame 103 in the expanded configuration, and the free ends 123 of the clipping arms 120 expand radially outward, with a second receiving space defined between the free ends 123 and the outer wall of the inner frame for clipping the native leaflets. In general, at least one native leaflet 201 is clipped between the clipping arm 120 and the inner frame 103 in vivo.

In the present application, the frame 110 for the prosthetic heart valve device is structurally improved. When applied to the aortic valve as a prosthetic aortic valve device, the positioning effect in case of aortic valve insufficiency diseases is improved, with the advantage of high assembly efficiency, convenient deployment and positioning, long-term stability and high durability, and having positive impact on the application of minimally invasive transcatheter aortic valve implantation devices for treating aortic valve insufficiency.

The positioning mechanism can be located at the respective valvular sinuses so that the prosthetic heart valve device can be aligned in the circumferential direction. The positioning mechanism and the inner frame 103 clipping the native leaflets or the positioning mechanism abutting against the sinus floors of the valvular sinuses allows am axial positioning so that the prosthetic heart valve device can be prevented from displacement under the influence of blood flow.

Spatially, both the first and second receiving spaces are radial gap between the outer wall of the inner frame and the positioning mechanism, and merely refer to different configurations. Therefore, unless otherwise specified, the receiving spaces are not strictly distinguished below. In some embodiments below, by changing the shape of the inner frame 103 or the deformation of the positioning mechanism, it is possible to make the second receiving space be smaller than the first receiving space in the radial direction of the inner frame. That is, the positioning mechanism in the released configuration tends to further clip the native leaflets relative to the transition configuration.

In the expanded configuration, the overall configuration of the inner frame 103 can be straight cylindrical, although in other implements, the outflow end of the inner frame can be flared outwards, which is also adapted to the changes in the size of the first and second receiving spaces.

In order to engage with the valvular sinuses, the fixed ends 121 of the clipping arms 120 in each group are adjacent to each other, the free ends 123 of at least two clipping arms 120 in each group tend to extend away from each other, and the free ends 123 of at least two clipping arms 120 in adjacent groups tend to extend close to each other. The clipping arms 120 are provided separately so as to avoid the positioning failure caused by an individual clipping arm(s) 120 which cannot be located in the valvular sinus. Taking the tricuspid valve as an example, three groups of clipping arms 120 are provided. The free ends 123 of at least two clipping arms 120 in each group tend to extend away from each other, which greatly increases the available anchor points, while the free ends 123 of at least two clipping arms 120 in the adjacent two groups tend to extend close to each, which conforms the anatomic structure of the valvular sinus.

In order to control the release sequence of the positioning mechanism and the inner frame 103 in the human body, the positioning mechanism is released by self-expanding and made of a suitable material, for example, a memory material such as a nickel-titanium alloy, and are preset to shape of the released configuration by heat treatment. The positioning mechanism can be automatically released prior to the inner frame 103 after being released from the radial constrain. The inner frame 103 is released by ball expanding and made of a suitable material. As the inner frame needs to be released and expanded by means of the balloon device, it can be released later than the positioning mechanism.

In the case where the inner frame 103 and the clipping arms 120 are both self-expanded, the delivery device would be more complicated and needs two sheaths connected in series or one surrounded by another so as to release the inner frame 103 and the clipping arms 120 in different steps, respectively, having more movable components and further reducing the compliance.

A specific portion can be provided by the inner frame 103 for connecting with the fixed end 121 of the clipping arm 120. Referring to FIG. 1, the inner frame 103 is provided with at least two commissure regions 114 spaced apart in the circumferential direction, with the coaptation portion of adjacent leaflets corresponding to the respective commissure region 114, and the fixed ends 121 of the clipping arms 120 in each group are connected to a corresponding commissure region 114. Specifically, the inner frame 103 is provided with a plurality of commissure regions 114 adjacent to the outflow end 102, and the fixed ends 121 of the clipping arms 120 in each group are connected to the corresponding commissure region 114. As shown in the figures, the number of the commissure regions 114 is preferably n, where n is the number of the leaflets 200 configured to be loaded in the frame 110. For example, in case of aorta valve, n is generally 3. More specifically, the edge of the inner frame 103 at the outflow end 102 has a structure with peaks and valleys, and the commissure regions 114 are located at the peaks (which protrude towards the outflow end 102). In another aspect, the axial length of the inner frame 103 varies in the circumferential direction of the inner frame 103, and gradually shortens as far away from the commissure region 114. Further, in the axial direction of the inner frame 103, the inner frame 103 has a plurality of rows of cells, including N rows of cells that respectively extend continuously in the circumferential direction adjacent the inflow end 101, and the remaining rows of cells respectively extend discontinuously in the circumferential direction, where N is 1, 2 or 3. As can be seen from the figure, in the circumferentially discontinuously extending rows of cells, the distance between the cells spaced from each other in the same row is larger as it is closer to the outflow end 102.

Figures 10, 11:
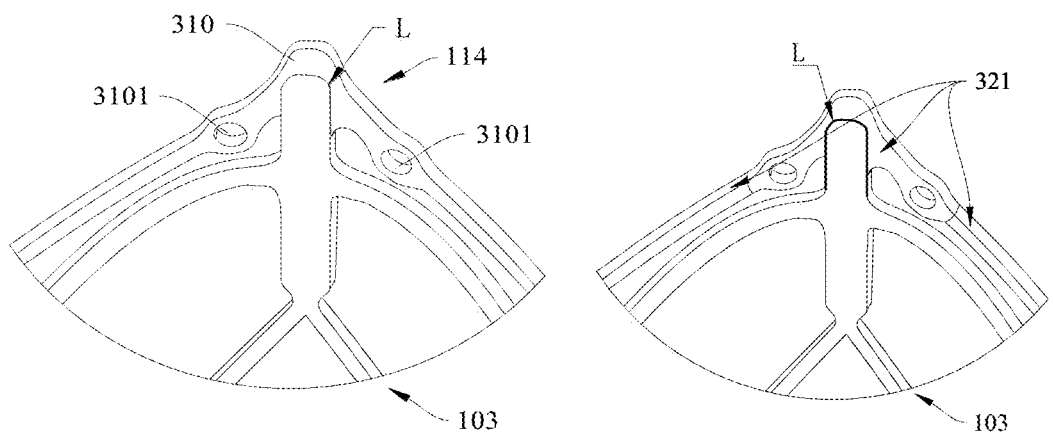

Referring to FIG. 8, the commissure region 114 is configured as a commissure post 132. In FIG. 10, each commissure post 132 extends from the outflow end 102 of the inner frame 103. Alternatively, the commissure posts 132 can extend from the interior of the inner frame 103. Specifically, the commissure post 132 can be configured as a bar, which extends along the axis of the inner frame 103 or the free end 123 of which is inclined radially inward. As shown in the figures, the commissure post 132 is configured as a solid rod. Alternatively, the commissure post 132 can be configured as a bar frame.

Referring to FIG. 8, the commissure post 132 is provided with a plurality of eyelets 1112. Alternatively, one eyelet 1112 can be provided. As shown in the figure, the plurality of eyelets 1112 on the commissure post 132 are arranged in sequence in the axial direction of the main body of the commissure post 132 to facilitate the processing and assembly.

The plurality of commissure posts 132 can be provided separately. As shown in FIG. 8, a pulling arm 142 is connected between adjacent commissure posts 132, and a first avoidance space 160 is defined between the pulling arm 142 and the outflow end 102 of the inner frame 103. In the loaded configuration, the clipping arms 120 can be located within the respective first avoidance spaces 160. The first avoidance space 160 provides motion space and receiving space for the clipping arm 120, thereby improving the engagement of the clipping arm 120 with the inner frame. For example, in the loaded configuration, all the clipping arms 120 do not radially overlap on the inner frame 103, which improves the loaded configuration of the inner frame 103, optimizing the profile of the inner frame 103 and facilitating assembly of the system as well as the treatment, wherein the small profile improves the compliance for in vivo delivery. The pulling arm 142 can extend straightly. Alternatively, as shown in the figure, the pulling arm 142 between two adjacent commissure posts 132 has a bent portion, i.e., an apex 146, and is generally V-shaped. In FIG. 7, the apex of the V-shape is fixedly connected with the edge of the inner frame 103 at the outflow end 102. Alternatively, in other embodiments, the apex of the V-shape can be free from the edge of the inner frame 103 at the outflow end 102.

Figure 14:
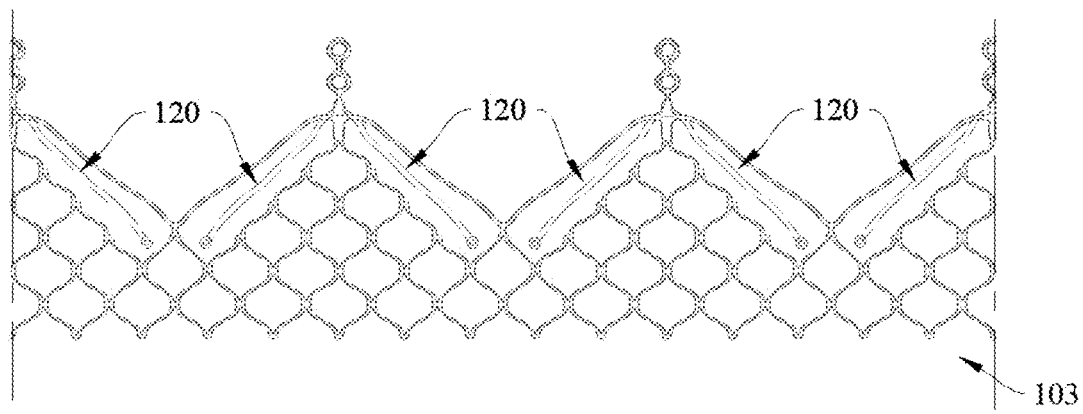
FIG. 14 is a flattened view of a frame of a prosthetic heart valve device according to an embodiment.

Referring to FIG. 14, the pulling arms 142 can be provided separately. Alternatively, referring to FIG. 7, the inner side of the V-shape is connected with a leg 141, and the middle portion of the leg 141 is bent, with the apex 146 protruding towards the outflow end 102. As shown in the figures, the inner side of the V-shape is configured as the outflow end 102 of the frame 110, and the pulling arm 142 is configured as a single rod. It can be conceived that the pulling arm 142 can be provided as a deformable meshed strip.

Similar to the above structure with peaks and valleys, in the present embodiment, the axial length of the inner frame 103 varies in the circumferential direction of the inner frame 103, and gradually shortens as far away from the commissure region 114. In the axial direction of the inner frame 103, the inner frame 103 has a plurality of rows of cells, including N rows of cells that respectively extend continuously in the circumferential direction adjacent the inflow end 101, and the remaining rows of cells respectively extend discontinuously in the circumferential direction, where N is 1, 2 or 3. In the circumferentially discontinuously extending rows of cells, the distance between the cells spaced from each other in the same row is larger as it is closer to the outflow end 102.

Referring to FIGS. 1c to 5b, one end of the clipping arm 120 is a fixed end 121 connected with the respective commissure region 114, and the other end is a free end 123 away from the commissure region 114. In the circumferential direction, the free ends 123 of the clipping arms 120 corresponding to adjacent two commissure regions 114 are adjacent to each other.

In order to better observe the position of the clipping arms 120 during the treatment, the clipping arms 120 are provided with one or more radiopaque points 173, and at least one radiopaque point 173 is adjacent the free end 123 of the clipping arm 120. Further, in the case of a plurality of radiopaque points 173, at least one radiopaque point 173 is adjacent to the free end 123 of the clipping arm 120, and at least one radiopaque point 173 is adjacent to the fixed end 121 of the clipping arm 120. The radiopaque point can be provided separately or share the same hole with other structure. For example, in FIG. 2c, the free end 123 of the clipping arm 120 is provided with an eyelet 551. The eyelet 551 can be used for providing the radiopaque point 173 and also for providing a rounded structure.

In order to reduce the damage of the clipping arm 120 to the native and surrounding tissues, as shown in the figures, the free end 123 of the clipping arm 120 is configured as a rounded structure 1221. Similarly, the free end 123 of the clipping arm 120 can be provided with a protective layer. The protective layer and the rounded structure 1221 can be provided in combination.

Further, the clipping arm 120 can have a deformable structure. The deformable structure can use various forms. For example, in FIG. 7, the clipping arm 120 is provided with one or more deformable slots 168. The deformable slot 168 can additionally extend the length of the clipping arm 120 in the released configuration. The length of the clipping arm 120 is one of the factors that determine the position of the fixed end 121 of the clipping arm 120, and thus determines the position of the frame 110 in the physiological anatomy. Therefore, by adjusting the number, position, and size of the deformable slots 168, the length of the clipping arm 120 can be adjusted, thereby extending the application of the prosthetic valve in the physiological anatomy. In the case where the deformable slot 168 is small, the radiopaque marker can be accommodated therein.

In the circumferential direction of the inner frame 103, various clipping arms 120 can be provided at one side where the individual commissure region 114 is located. In the embodiment shown in FIG. 1c, one single clipping arm 120 is provided at one side where the commissure region 114 is located. Alternatively, as shown in FIG. 7, the single clipping arm 120 can have a branched structure at the middle thereof that converges at the free end 123. The free end 123 of the clipping arm 120 can also have a branched structure. Alternatively, a plurality of clipping arms 120 can be provided at one side where the commissure region 114 is located as shown in FIG. 5b. The clipping arms 120 can be configured as a single bar or configured as a deformable meshed strip.

In the deployed state, the angle between the clipping arm 120 and the axis of the inner frame 103 ranges from 30 to 85 degrees, where the angle is measured referring to the line connecting the two ends of the clipping arm 120.

Regarding the distribution of the clipping arms 120, the clipping arms 120 on two opposite sides of the commissure region 114 are symmetrically distributed, and in the circumferential direction of the inner frame 103, the clipping arms 120 between the adjacent commissure regions 114 are symmetrically distributed.

Figures 12A, 12B:
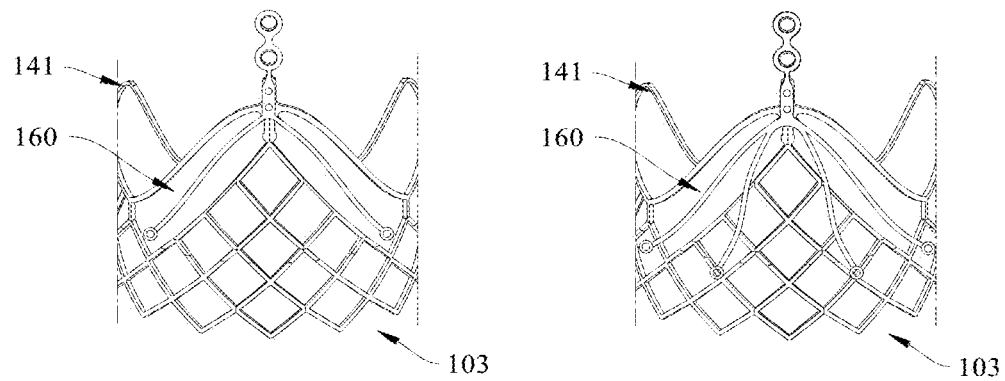
FIG. 12a to FIG. 12d illustrate the engagement between the frame in FIG. 7 with different clipping arms, respectively.
Figures 12C, 12D:
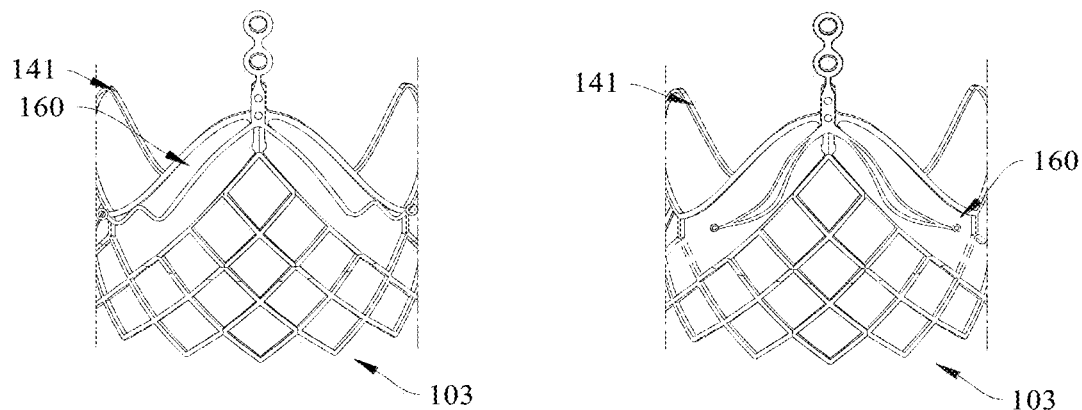
Figure 13:
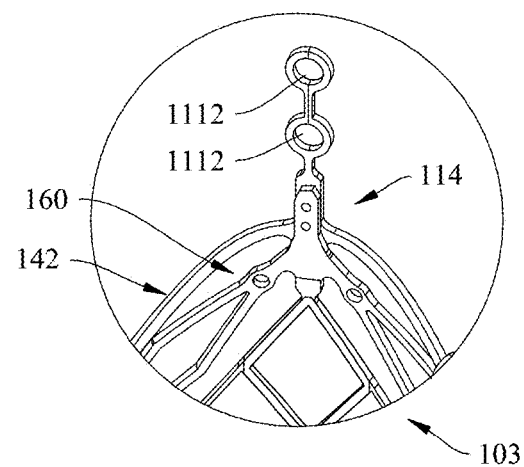
FIG. 13 is a perspective view of the clipping arm inside the inner frame.

FIGS. 12a to 13 show the engagement between the clipping arms 120 and the inner frame, wherein the clipping arms 120 are all connected to the inner frame by riveting. As shown in FIGS. 12a to 12d, the clipping arm is connected with the outer peripheral surface of the inner frame, while in FIG. 13, the clipping arm is connected with the inner peripheral surface of the inner frame. It can be conceived that the clipping arms shown in FIGS. 12a to 12d can be connected with the inner peripheral surface of the inner frame.

The fixed ends 121 of the clipping arms 120 can be connected with the inner frame 103 separately or in combination. In the embodiment shown in FIG. 8 to 11, the fixed ends 121 of the clipping arms 120 in each group converge to a connecting portion 310 and are fixed to the inner frame 103 by the connecting portion 310. The connecting portion 310 and the clipping arms 120 joined to the connecting portion 310 can be formed in one piece, for example, by cutting or knitting. Further, in the circumferential direction of the inner frame 103, the clipping arms 120 in each group are distributed on two sides of the connecting portion 310. In practice, the inner frame 103 is provided with at least two commissure regions 114 at intervals in the circumferential direction, and the connecting portions 310 are respectively fixed to the commissure regions 114 on the inner frame 103 by welding or by connecting members 315.

The connecting portion 310 can connect the clipping arms 120 and the inner frame 103 better while adapting different expansion characteristics of the two. Further, the engagement between the connecting portion 310 and the commissure region 114 can be various. For example, referring to FIG. 3a, the connecting portion 310 is overlapped on the outer side of the commissure region 114 in the radial direction of the inner frame 103. Referring to FIG. 13, the connecting portion 310 is overlapped on the inner side of the commissure region 114 in the radial direction of the inner frame 103. Referring to FIG. 8, in the circumferential direction of the frame 110, the connecting portion 310 is located on one circumferential side of the commissure region 114, that is, the connecting portion 310 does not radially overlap on the commissure region 114. Referring to FIGS. 10 and 11, the connecting portion 310 covers the top of the commissure region 114. Compared with FIG. 3a and FIG. 13, the junction in FIG. 8, FIG. 10 and FIG. 11 is more invisible and cannot be clearly shown in the figures, and thus is represented by a thick line L. The above-mentioned various configurations have different advantages in terms of assembly difficulty and volume in the loaded configuration.

Figure 6A:
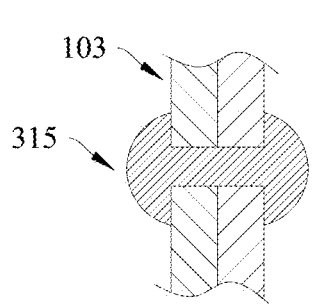
FIG. 6a to FIG. 6c illustrate the assemble of the fixed end and the commissure region in different embodiments, respectively.
Figure 6C:
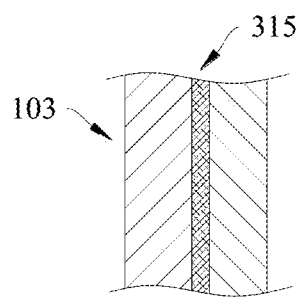
Figure 6D:
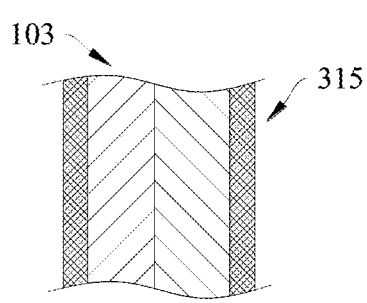

In the case where the connecting member 315 is used for fixing, the specific implementation of the connecting member 315 can refer to FIGS. 6b to 6c. In the figures, the connecting member 315 is configured as a fixing member passing through the connecting portion 310 and the commissure region 114. Specifically, with reference to FIG. 6a, the connecting member 315 can be configured as a screw, a rivet, a binding wire, or the like. Alternatively, as shown in FIG. 6b, the connecting member 315 can be configured as a sandwiched adhesive lay. Alternatively, as shown in FIG. 6c, the connecting member 315 can be configured as a covering structure.

Figure 28:
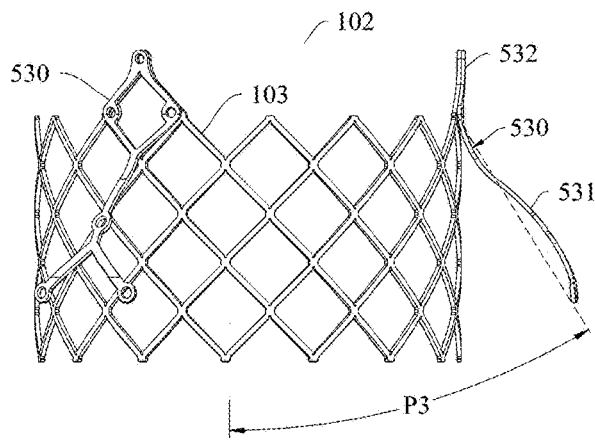
FIG. 28 is a left side view of the prosthetic aortic valve device of FIG. 27.

As shown in FIG. 28, the connecting portions 310 corresponding to the clipping arms 120 in each group are formed in one piece. Referring to FIG. 11, the connecting portions 310 corresponding to the clipping arms 120 in each group can be separated and adjacent to each other. Further, the separated structure includes a plurality of units 321, which are separated and respectively connected to the commissure region 114 of the inner frame 103, or the plurality of units 321 can be fixed to each other, with at least one unit 321 connected to the commissure region 114 of the inner frame 103.

Similarly to the radiopaque configuration in the clipping arm 120, the connecting portion 310 can also be provided with a radiopaque hole(s) 3101 for mounting the radiopaque element(s), in order to provide a more clear observation.

The clipping arm 120 can use various forms. FIGS. 2a to 2d, 4a to 4d, and 5a to 5b shows different perspectives of the clipping arms with different arrangements.

FIGS. 2a to 2d show front view of FIG. 1, which can be considered as showing the clipping arm projected on the paper in the front view; in the case where the clipping arm, when projected on the paper, has no configuration as shown in the figures, the shown clipping arm can be considered as the configuration being flattened.

FIGS. 4a to 4d show the released configuration of the clipping arm in a cylindrical coordinate, wherein the dotted line shows the cylindrical coordinate. In order to better show the three-dimensional configuration of the clipping arm in the two-dimensional figures, the cylinder of the cylindrical coordinate in the figure is depicted referring to the profile of the frame, so these figures can be approximately understood as showing the spatial relationship between the frame and the clipping arm.

Figure 5A:
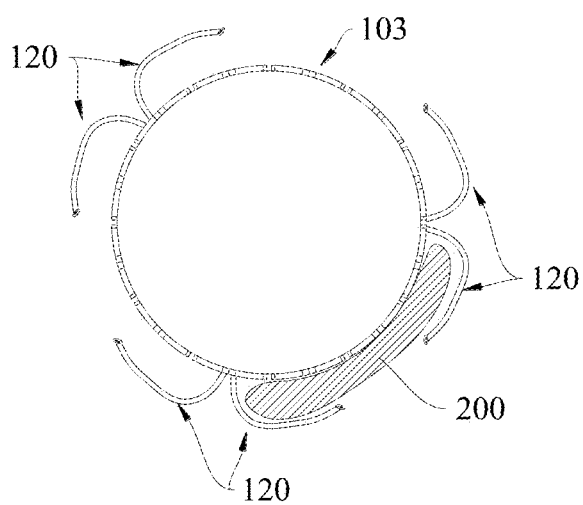
FIG. 5a and FIG. 5b illustrate the engagement between the clipping arms and the inner frame according to different embodiments in a top view, respectively.
Figure 5B:
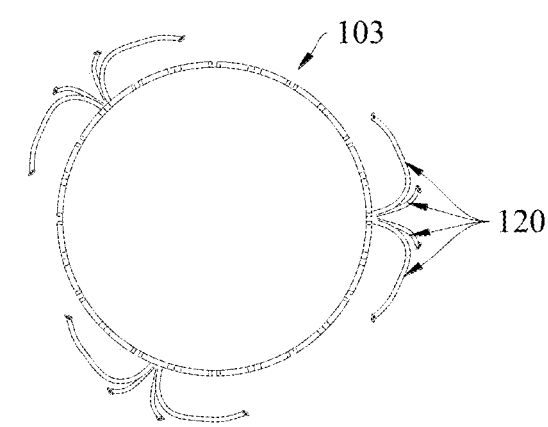

FIGS. 5a to 5b show top views of FIG. 1, and can be understood as showing the clipping arm projected on the paper in the top view; in the case where the clipping arm, when projected on the paper, has no configuration as shown in the figures, the shown clipping arm can be considered as the configuration being flattened.

Figure 2A:
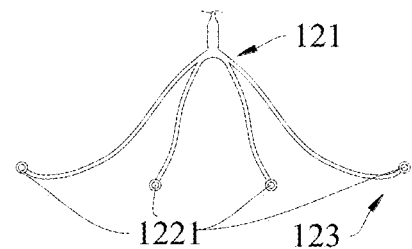
FIG. 2a to FIG. 2d illustrate different examples of the clipping arms in front view, respectively.
Figure 2B:
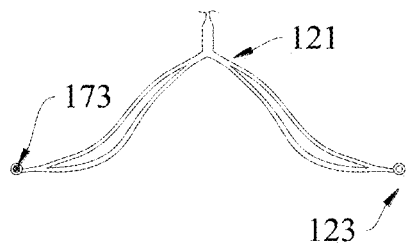
Figure 2C:
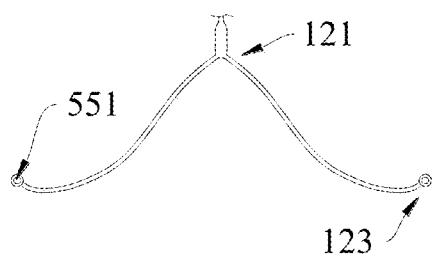
Figure 2D:
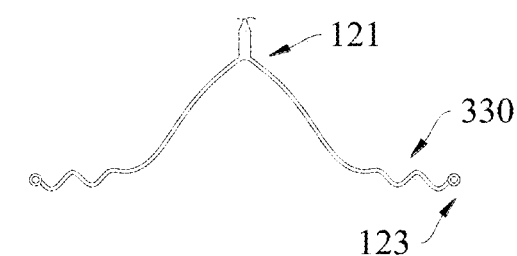
Figure 4C:
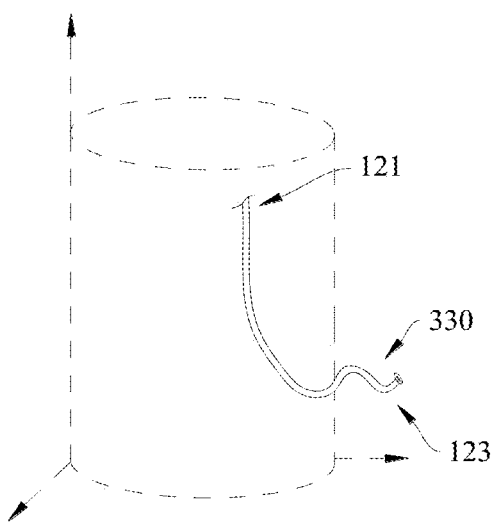
Figure 4D:
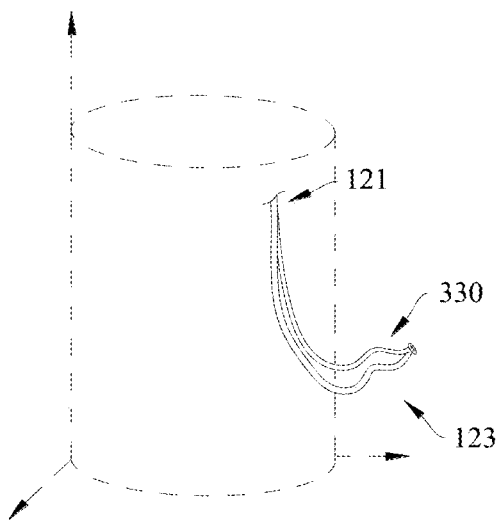

Referring to FIG. 2d, FIG. 4c, and FIG. 4d, the clipping arm 120 has a wave structure 330 adjacent to the free end 123. In the figures, the wave structure 330 mainly undulates in the axial direction of the frame 110. It can be conceived that the clipping arm 120 can have undulations in multiple directions in space. Referring to FIGS. 5a and 5b, the clipping arm 120 has a radially undulating structure as viewed in the axis of the inner frame 103. The undulations in multiple directions can be provided separately or overlapped with each other to form a complex three-dimensional configuration.

The clipping arms 120 can be divided into a plurality of groups, depending on the position of the fixed ends 121. Each group of clipping arms 120 can include one or more pairs of clipping arms 120. In the embodiment shown in FIG. 5b, each group includes multiple pairs of clipping arms 120. In the circumferential direction of the inner frame 103, the clipping arms 120 in each pair are respectively located on two sides of the connecting portion 310, and the clipping arms 120 in different pairs have different lengths after being released.

In another aspect, in the circumferential direction of the inner frame 103, the clipping arms 120 in each group are divided into pairs of clipping arms 120, and the clipping arms 120 in each pair are respectively located on two sides of the connecting portion 310. In the released configuration, the clipping arms 120 on the same side of the connecting portion 310 while in different pairs have different extensions as shown in FIG. 4d.

The different configurations described above represent the three-dimensional configurations of the clipping arm 120 in the released configuration. Further, referring to FIG. 5a, in the released configuration, the free ends 123 of the clipping arms 120 in each group are located at the same radial position relative to the inner frame 103. Referring to FIG. 5b, in the released configuration, the free ends 123 of the clipping arms 120 in each group are offset from each in the radial direction relative to the inner frame 103. However, the free ends 123 of all the clipping arms 120 in the aforementioned two cases are both located between the two ends of the inner frame 103 in the axial direction of the inner frame 103 in the released configuration, wherein the two ends of the inner frame 103 in the present embodiment refer to the inflow end 101 and the outflow end 102 of the inner frame 103, so as to prevent the clipping arms 120 from affecting the release and positioning of the frame 110.

Figure 2E:
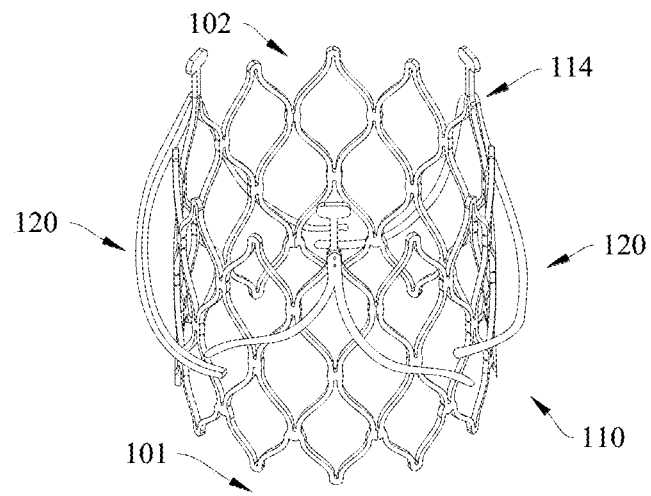
FIG. 2e illustrates an asymmetric configuration of the clipping arms.

The plurality of clipping arms 120 can use the same configuration as describe above. Alternatively, the plurality of clipping arms 120 can use different configurations in one embodiment as shown in FIG. 2e. Specifically, two adjacent clipping arms 120 in different groups have different lengths. Further, the clipping arms 120 in each group can be different. For example, the two clipping arms 120 in each group can have different lengths. Besides the difference in the extension length of the clipping arms 120, the free ends of adjacent two clipping arms in different groups can be offset from each other in the circumferential direction of the inner frame. As shown in the figure, the clipping arm 120 has a bent portion adjacent to the free end thereof so as to change the extension path thereof. In the deployed state, the bent portion of one of the adjacent clipping arms surrounds the free end of the other in half, which further improves the positioning of the clipping arms 120 on the native leaflet.

Referring to FIGS. 14 to 19m, the present application discloses a prosthetic heart valve device, including leaflets and a frame 110. Different from the above embodiments, the frame 110 in this embodiment further includes:
a connecting ring 340 fixed with the outflow end 102 of the inner frame 103 and provided with a plurality of connecting regions 341 at intervals; and the fixed ends 121 of clipping arms 120 in each group are located at the same connecting region 341.

Figure 20A:
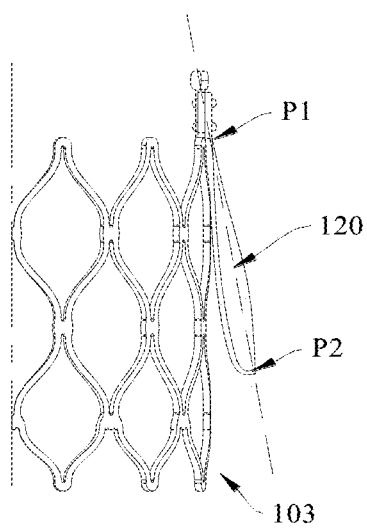
FIG. 20a is a side view of a frame with a reinforced clipping arm according to another embodiment.
Figure 20B:
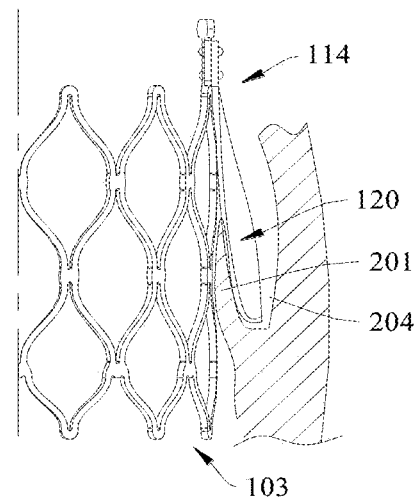
FIG. 20b is a view showing the engagement between the frame in FIG. 20a and native leaflet.
Figure 20C:
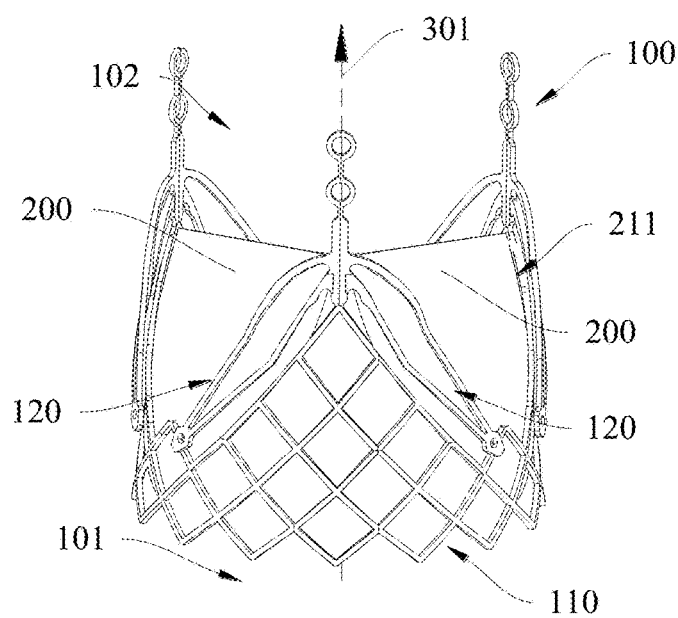
FIG. 20c is a perspective view of a prosthetic heart valve device with reinforced clipping arms according to one embodiment.
Figure 20D:
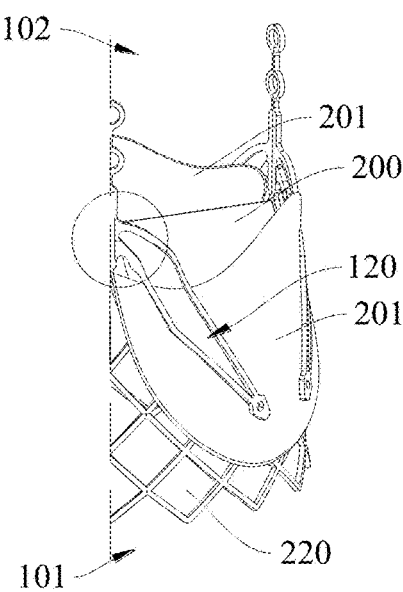
FIG. 20d is a view showing the engagement between the prosthetic heart valve device of FIG. 20c and the native valve leaflet.
Figure 20E:
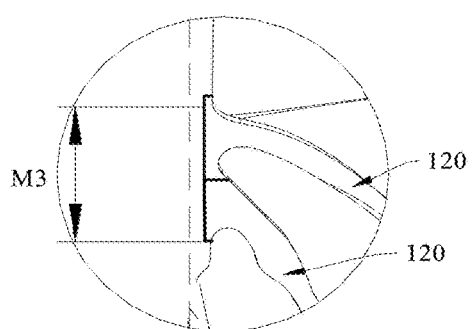
FIGS. 20e and 20f are views showing the engagement between the fixed ends of the clipping arms, respectively.
Figure 20F:
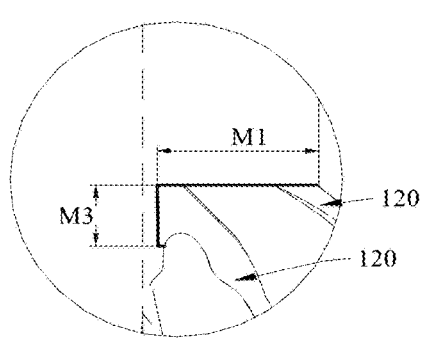
Figure 20G:
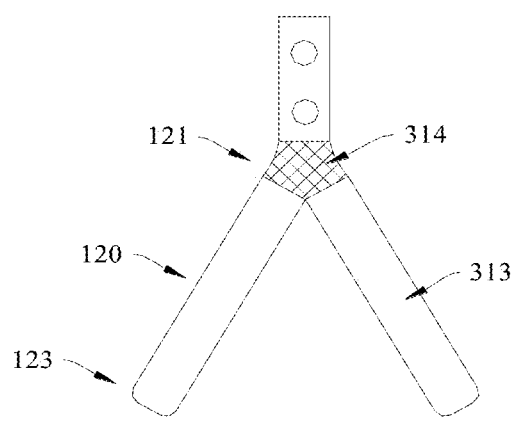
FIG. 20g is a view of reinforced clipping arms according to another embodiment.

In this embodiment, the plurality of groups of the clipping arms 120 are connected by the connecting ring 340, so that the clipping arms 120 and the inner frame 103 can be separately provided with more flexibility. In general, the free ends 123 of at least two clipping arms 120 in each group tend to extend away from each other, and the free ends 123 of at least two clipping arms 120 in adjacent two groups tend to extend close to each other. The clipping arms 120 forms a deformable deployed structure on the outer periphery of the inner frame 103. The clipping arm 120 can be connected with the inner frame by the connecting portion 310. Specifically, in one embodiment, the connecting portion 310 can be overlapped on the outer side of the commissure region 114 in the radial direction of the inner frame 103. Alternatively, in another embodiment, the connecting portion 310 can be overlapped on the inner side of the commissure region 114 in the radial direction of the inner frame 103. Alternatively, in a further embodiment, the connecting portion 310 can be connected at one circumferential side of the commissure region 114 in the circumferential direction of the frame 110, that is, the connecting portion 310 does not radially overlap on the commissure region 114. In FIGS. 20*e* and 20*f*, the junction is more invisible and cannot be clearly shown in the figures, and thus is represented in a bold in the figures. The above-mentioned various configurations have different advantages in terms of assembly difficulty and volume in the loaded configuration.

Figure 15A:
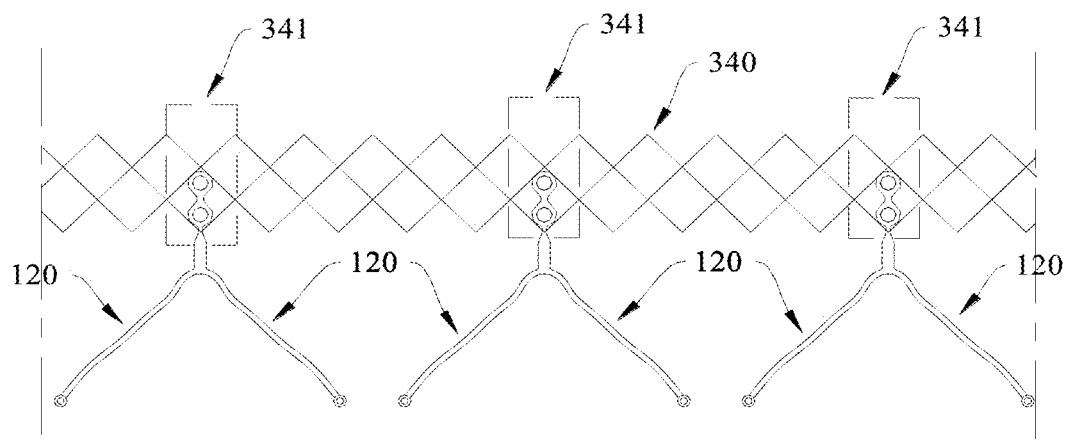
FIG. 15a is a view of a connecting ring according to an embodiment.
Figure 15B:
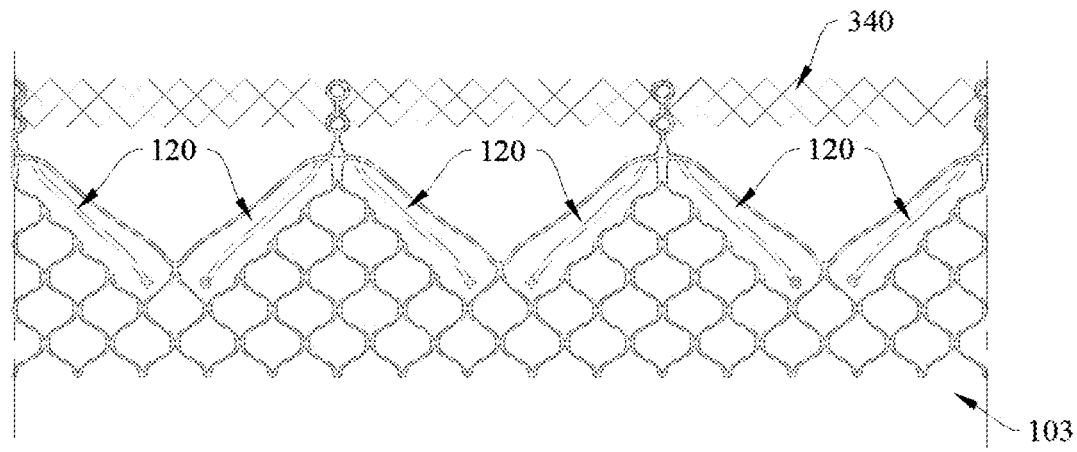
FIG. 15b is a view showing the engagement between the connecting ring in FIG. 15a and the frame.
Figure 15C:
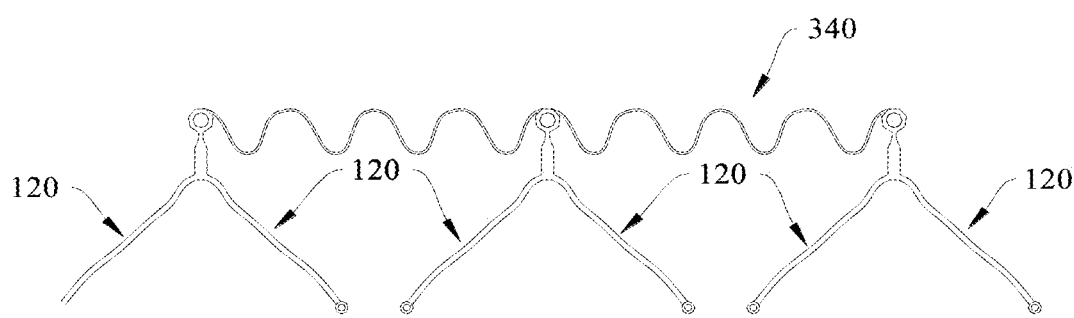
FIG. 15c is a view of a connecting ring according to another embodiment.
Figure 15D:
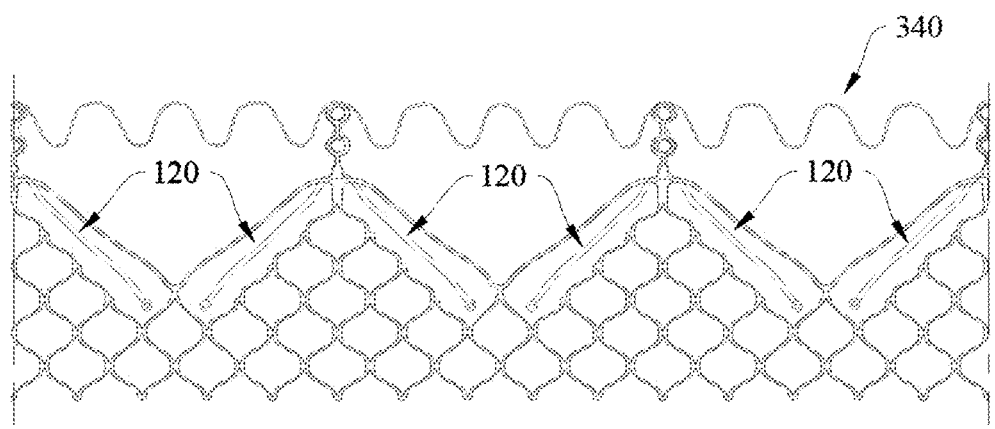
FIG. 15d is a view showing the engagement between the connecting ring in FIG. 15c and the frame.
Figure 15E:
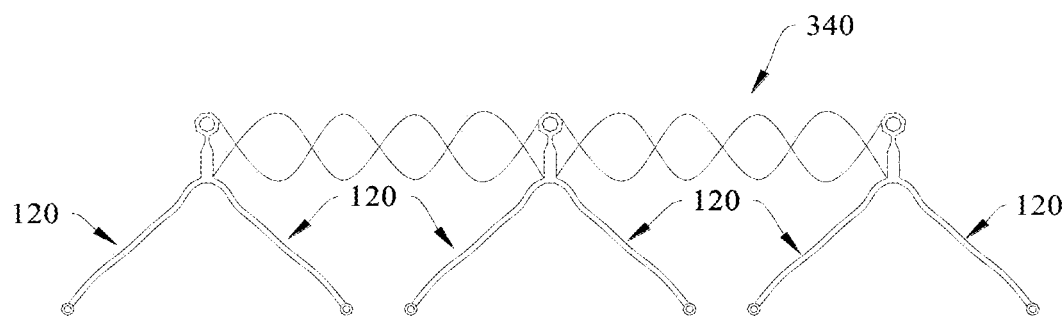
FIG. 15e is a view of a connecting ring according to a further embodiment.
Figure 15F:
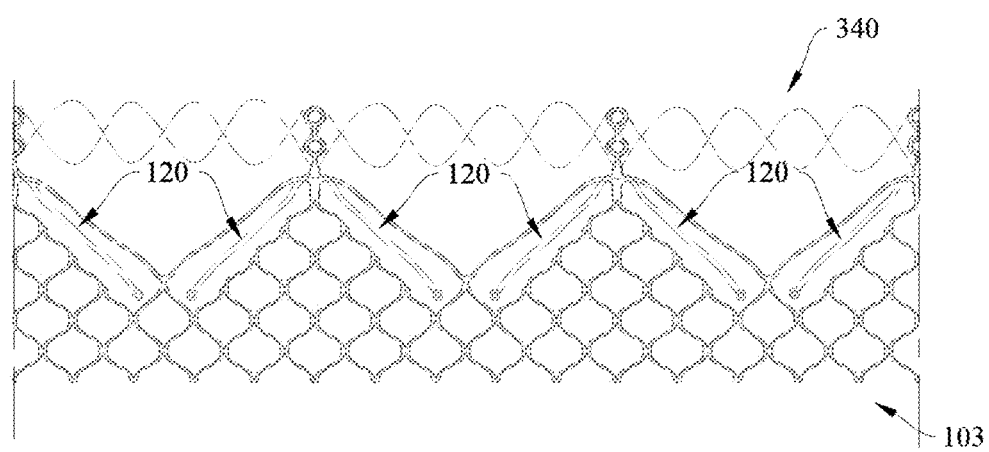
FIG. 15f is a view showing the engagement between the connecting ring in FIG. 15e and the frame.

Referring to FIG. 15*a*, the fixed ends 121 of the clipping arms 120 in different groups are located at different connecting regions 341. Referring to FIG. 18*a*, the connecting ring 340 surrounds and is connected with the outer periphery of the inner frame 103. Alternatively, referring to FIG. 17, the connecting ring 340 is connected with one axial end of the inner frame 103. Further, the connecting ring 340 is configured as a radially deformable structure. In practice, the connecting ring 340 can be configured as a meshed strip. Referring to FIGS. 16*a* and 16*b*, the connecting ring 340 is configured as a single-strand strip, which extends along the circumferential direction of the inner frame 103, and has a wave structure 330 undulating in the axial direction of the inner frame 103.

Figure 18:
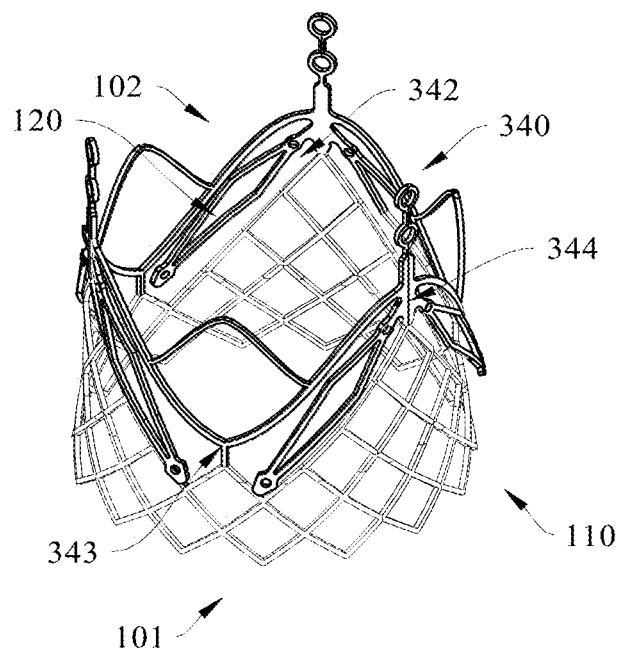
FIG. 18 is a perspective view of a frame of a prosthetic heart valve device according to another embodiment.

In the released configuration, an independent space is defined between the connecting ring 340 and the clipping arms 120, so that the connecting ring 340 can be more flexibly engaged with the inner frame 103. Referring to FIG. 18, the inflow end 101 of the coupling ring 340 is connected with the outflow end 102 of the inner frame 103, which allows the connecting ring 340 and the inner frame 103 to be offset from each other in the axial direction. Further, a second avoidance space 342 is defined between the inflow end 101 of the connecting ring 340 and the outflow end 102 of the inner frame 103, and the clipping arms 120 are located within the respective second avoidance space 342 in the loaded configuration. Specifically, the connecting ring 340 is connected with the inner frame 103 at a first position 343 and/or a second position 344. Different connection positions and numbers affect the mechanical performance of the connecting ring 340, thereby affecting the movement of the clipping arms 120. The clipping arm 120 is connected with the connecting ring 340 at the second position 344. The first position 343 and the second position 344 are offset from each other in the circumferential direction of the inner frame 103, and the offset angle is 360/2n, where n is the number of leaflets 200 configured to be loaded in the frame 110. As shown in the figure, the frame 110 shown is used for a tricuspid valve, so the first position 343 and the second position 344 are offset by an angle of 60 degrees.

Independent from the above configuration, the coupling ring 340 and the inner frame 103 do not overlap each other, so that they are allowed to be compressed into a desired volume, which facilitates the treatment.

The axial offset and the radial offset between the connecting ring 340 and the inner frame 103 can be achieved separately and independently, or in combination as shown in the figures.

Regarding the connection between the groups of clipping arms 120 and the inner frame 103, see FIG. 18, the fixed ends 121 of the clipping arms 120 in each group converge to the connecting ring 340 adjacent the outflow end 102 of the inner frame 103. As shown in FIG. 18, the connecting ring 340 is rigidly fixed with the commissure region 114.

Figure 16:
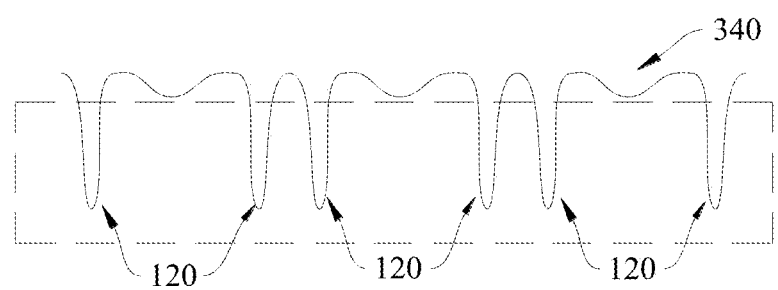
FIGS. 16 and 17 are views of a connecting ring and a clipping arm formed in one piece according to different embodiments, respectively.
Figure 17:
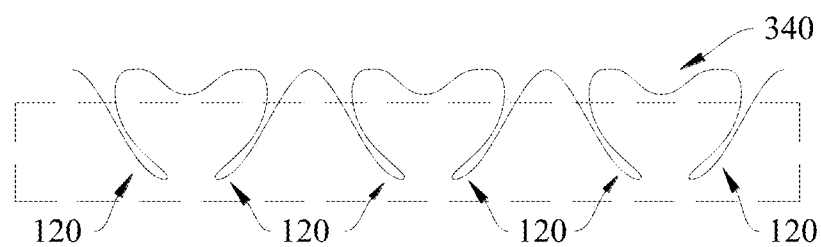

Besides the above-mentioned connection methods for the connecting ring 340 and the clipping arms 120, as shown in FIGS. 16 and 17, the connecting ring 340 and the clipping arms 120 can be formed in one piece. Further, the connecting ring 340 and the clipping arms 120 are formed by winding a wire(s). In practice, the wire is configured as a single wire without a break. The wire can be made of an alloy material having a memory effect.

Figure 19A:
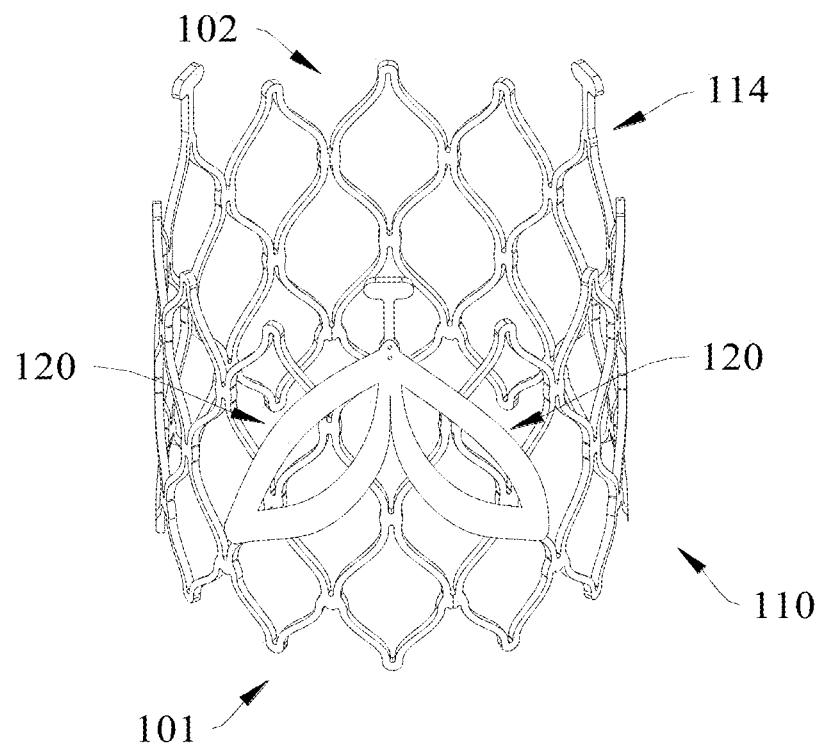
FIG. 19a is a perspective view of a frame with reinforced clipping arms according to an embodiment.

Referring to FIG. 19*a*, the present application further discloses a prosthetic heart valve device, including leaflets and a frame 110. The difference of this embodiment from the above embodiments is that the circumferential distribution region M1 of the fixed end 121 of the clipping arm 120 has a central angle greater than 15 degrees with respect to the axis of the inner frame 103.

FIG. 19*a* shows a group of reinforced clipping arms 120. In this embodiment, on the one hand, the frame is self-expanded by means of a support device (such as a balloon), on the other hand, the separate clipping arms 120 are reinforced by optimizing the shape or size thereof, thereby improving the positioning effect of the clipping arms 120 on the native leaflet 201. Compared with the clipping arm 120 configured as a single rod or the like, the reinforced clipping arm 120 according to this embodiment has a more stable positioning effect.

Specifically, the circumferential distribution region M1 and the axial distribution region M3 of the fixed end 121 of the individual clipping arm 120 are improved, to ensure the connection strength of the single clipping arm 120 with the inner frame 103 as well as the spatial shaping performance thereof.

Figure 19B:
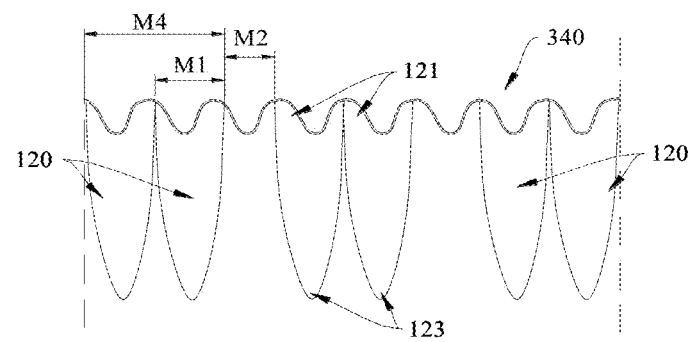
FIG. 19b is a flattened view of a frame with reinforced clipping arms according to an embodiment.
Figure 19C:
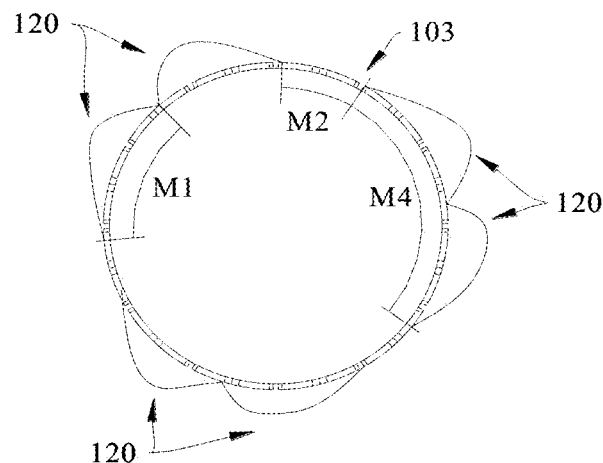
FIG. 19c is a top view of the frame of FIG. 19b.
Figure 19D:
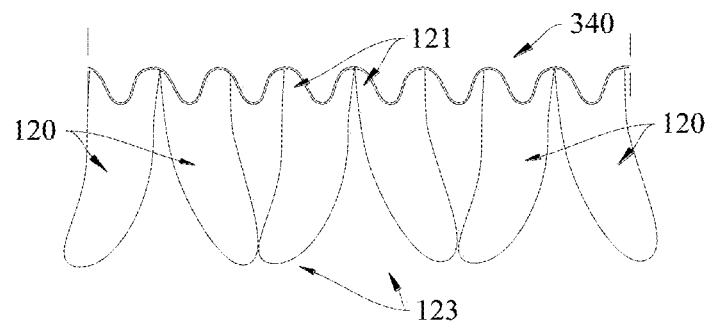
FIG. 19d is a flattened view of a frame with reinforced clipping arms according to another embodiment.
Figure 19E:
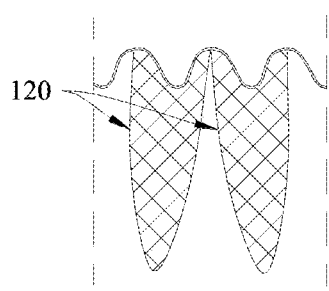
FIG. 19e is a view of clipping arms configured as meshed strips.
Figure 19F:
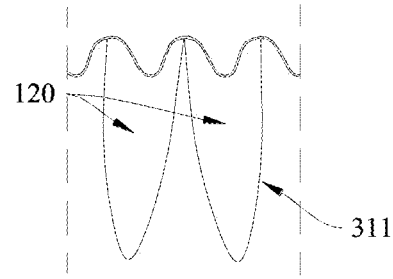
FIG. 19f is a view of clipping arms with thickened edges.
Figure 19G:
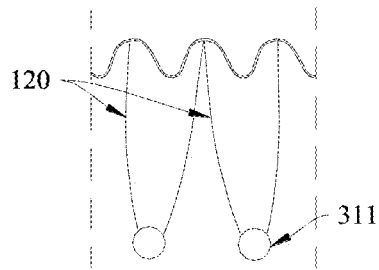
FIG. 19g is a view of clipping arms with positioning structures at the free ends thereof.
Figure 19H:
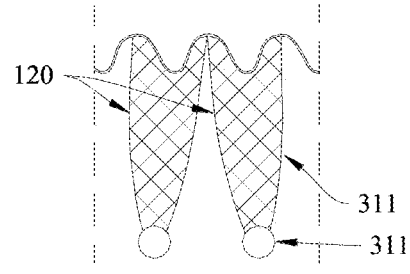
FIG. 19h is a view of clipping arms with various positioning structures provided thereon.
Figure 19I:
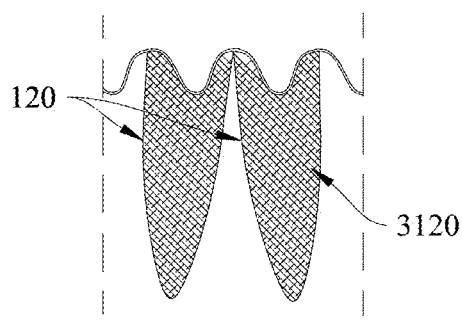
FIG. 19i is a view of clipping arms with sleeves.
Figure 19J:
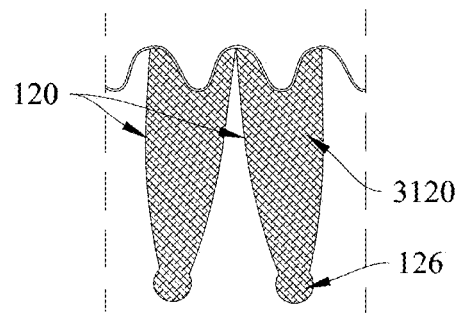
FIG. 19j is a view of clipping arm with sleeves and positioning structures simultaneously provided thereon.
Figure 19K:
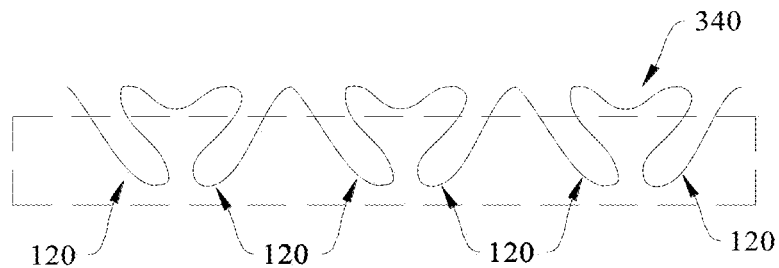
FIG. 19k is a view of reinforced clipping arms formed in one piece.
Figure 19L:
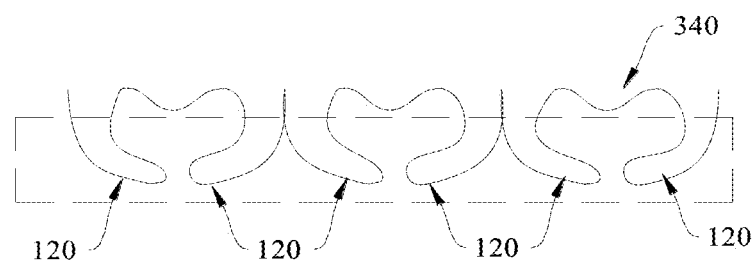
FIG. 19l is a view of reinforced clipping arms formed in one piece with different extensions.
Figure 19M:
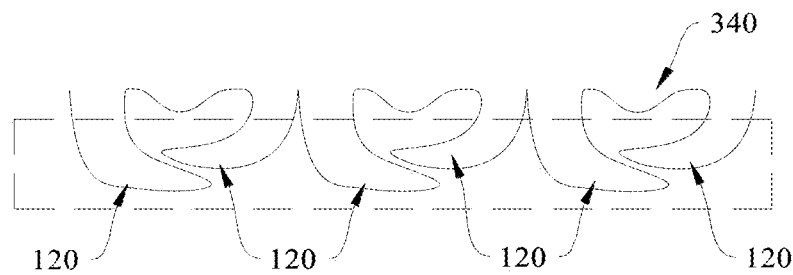
FIG. 19m is a view of asymmetric reinforced clipping arms formed in one piece with different extensions.

Regarding the connection between the clipping arms 120 and the inner frame 103, as shown in FIGS. 19*b* to 19*m*, the clipping arms 120 are connected with a separate connecting ring, and then connected to the inner frame 103 by the connecting ring to form a frame with separate pieces. Alternatively, as shown in FIGS. 10*a* to 20*f*, the clipping arms 120 are directly connected to the inner frame 103 to form a frame with a one piece. In FIGS. 19*k*, 19*l*, and 19*m*, the connecting ring and the clipping arms 120 are formed by winding a wire, but the clipping arms 120 in FIGS. 19*k*, 19*l*, and 19*m* have different shapes. As shown in FIG. 19*l*, the clipping arm 120 extends approximately in the axial direction of the inner frame 103, and then turns to extending approximately in the circumferential direction of the inner frame 103. As shown in FIG. 19*m*, the clipping arms 120 in each group can be asymmetrically arranged.

Referring to FIGS. 19*a* to 20*f*, the clipping arms 120 are arranged in groups, and the fixed ends 121 of the clipping arms 120 in each group are adjacent to each other. Comparing FIGS. 19*b* and 19*d*, it can be seen that the free ends 123 of the clipping arms 120 can be moved away from or closer to each other to achieve different positioning effects.

In order to avoid interference between the clipping arms 120 in the circumferential direction, the clipping arm 120 is sized so that the central angle of the circumferential distribution region M4 of the fixed ends 121 of the clipping arms 120 in each group with respect to the axis is equal to or less than 360/n, where n is the number of leaflets 200 configured to be loaded in the frame 110. As shown in the figures, the frame 110 is used for a tricuspid valve, and thus the central angle of the circumferential distribution region M1 of the fixed ends 121 of the clipping arms 120 in each group with respect to the axis is less than or equal to 120 degrees.

The central angle of the circumferential distribution region M1 of the fixed end 121 of the clipping arm 120 with respect to the axis is equal to or less than 360/2n, where n is the number of leaflets 200 configured to be loaded in the frame 110. Similarly, as shown in the figures, the central angle of the circumferential distribution region M1 of the fixed end 121 of the clipping arm 120 with respect to the axis is smaller than or equal to 60 degrees.

The above-described parameters can avoid a reduced freedom of motion of the clipping arm 120 caused by the increased size, thereby ensuring the positioning effect.

Referring to FIG. 19b, FIG. 19c and FIG. 20f, it can be seen that the circumferential distribution region M1 shown in the figures represents the projection dimension of the fixed end 121 of the clipping arm 120 in the circumferential direction of the inner frame 103. In another embodiment, the length of the axial distribution region M3 of the fixed end 121 of the clipping arm 120 relative to the inner frame 103 is greater than 5 mm. The axial distribution region M3 represents the projection dimension of the fixed end 121 of the clipping arm 120 in the axial direction of the inner frame 103. Alternatively, the circumferential distribution region M1 and the axial distribution region M3 can be combined.

Referring to FIGS. 20e and 20f, depending on the different configurations of the fixed end 121, the circumferential distribution region M1 and the axial distribution region M3 are adjusted correspondingly, and the specific junction (shown by a thick solid line in the figures) between the clipping arm 120 and the inner frame 103 is also changed correspondingly.

In general, when projected onto the peripheral surface of the inner frame 103, the clipping arm 120 assumes a sheet-like structure having a certain area. Referring to FIG. 19a, FIG. 19d and FIG. 20a, the clipping arm 120 generally has a curved extension from the fixed end 121 to the free end 123, and two clipping arms 120 in adjacent groups cooperate with each other to conform to the anatomic structure of the valvular sinus 204. Specifically, and for example, within two clipping arms 120 in adjacent two groups, the overall structure gradually converges from the outflow end 102 to the inflow end 101, that is, the span between the two clipping arms 120 in the circumferential direction of the inner frame 103 gradually decreases until the free ends 123 thereof are close to each other. With regard to the specific extension path, the clipping arm 120 can extend uniformly in the circumferential and axial directions of the inner frame 103 as shown in FIG. 19a, or first extends approximately in the circumferential direction of the inner frame 103 and then turns to extending approximately in the axial direction of the inner frame 103 as shown in FIG. 20d, or refer to FIG. 20j.

At least a spacing region M2 is defined between the fixed ends 121 of the two clipping arms 120 in adjacent groups in the circumferential direction of the inner frame 103, wherein the spacing region M2 has a center angle relative to the axis greater than 30 degrees, for example, 60 to 120 degrees. The spacing region M2 can reduce interference between clipping arms 120 in adjacent groups and low the risk of simultaneous failure.

With regard to the specific structure of the clipping arm 120, each of the clipping arms 120 has a multi-bar structure from the fixed end 121 to the free end 123. The multi-bar structure is configured so that there are at least two bars of the clipping arm 120 at any portion in any direction which can be one or more of the axial direction, the radial direction, and the circumferential direction of the frame 110. Alternatively, referring to FIG. 19e, each of the clipping arms 120 is configured as a meshed strip consisting of bars, and there are at least two bars at any position in the extension direction of the clipping arm 120. In the case where the clipping arm 120 is configured as a single bar, the strength there will be inevitably decreased, affecting the overall strength and positioning effect. The meshed strip is generally configured as a sheet-like structure, where the clipping arm 120 extends in a single layer or in double layers from the fixed end 121 to the free end 123. Further, a solid sheet-like structure, i.e., a relatively closed sheet-like structure in space, can be formed by filling the hollowed-out regions of the meshed strip of the clipping arm 120, and the specific filter can be a polymer material or a metal material. In the case where the filter chooses the same material as the bars of the clipping arm 120, the clipping arm 120 is generally formed as a leaf-shaped metal sheet.

Figure 20H:
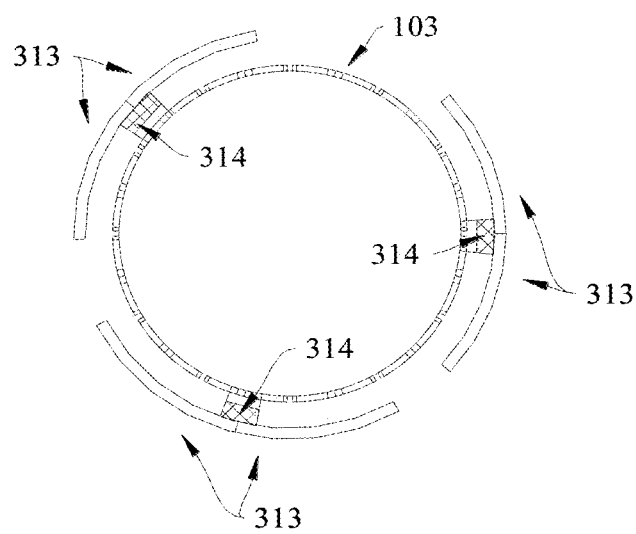
FIG. 20h shows the engagement between the clipping arms and the inner frame in FIG. 20g.
Figure 20I:
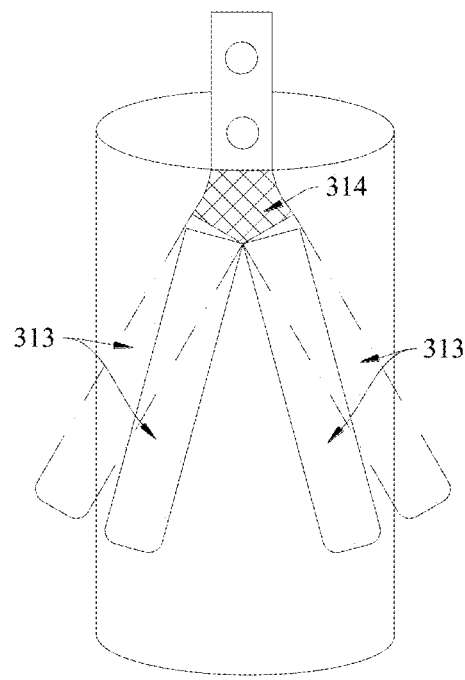
FIG. 20i is a view comparing the loaded configuration and the released configuration of the clipping arms of FIG. 20g.
Figure 20J:
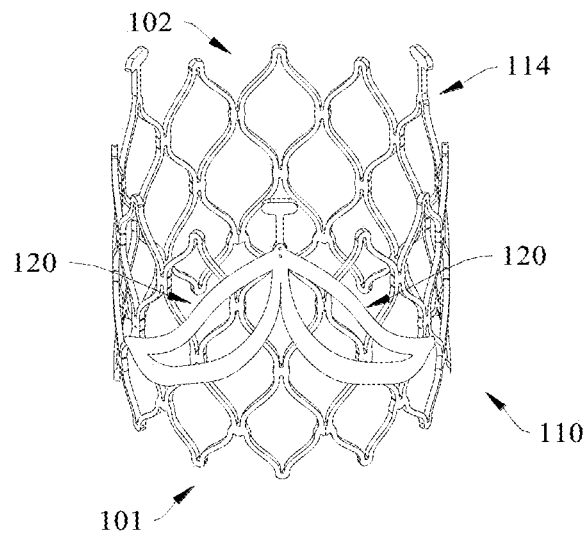
FIG. 20j illustrates different extensions of the reinforced clipping arms.

However, the clipping arm, which is generally formed as a metal sheet, results in problems in switching between the loaded configuration and the released configuration. In the embodiment shown with reference to FIG. 20g, the portion of the clipping arm 120 adjacent to the free end 123 is configured as an undeformable rigid portion 313. The undeformable rigid portion 313 should be understood as a portion which is designed to be undeformable, rather than being a rigid body in strict mechanical meaning. Referring to FIG. 20i, the rigid portion 313 maintains the same or similar shape and form both in the loaded configuration and the released configuration. In terms of mechanical properties, the deformation resistance of the rigid portion 313 is significantly higher than that of other portions of the clipping arm 120, particularly the flexible portion 314 mentioned below. Specifically, the rigid portion 313 can be implemented by a specific rigid material, or by a specific rigid structure. As shown in the figures, the rigid portion 313 is configured as a solid sheet-like structure.

The rigid portion 313 is provided so that the self-deformation of the clipping arm 120 is concentrated on the fixed end 121, which can be implemented by weakening the mechanical properties of the fixed end 121. Alternatively, referring to one embodiment, the fixed end 121 of the clipping arm 120 is configured as a deformable flexible portion 314. Alternatively, referring to another embodiment, the clipping arms 120 in each group are connected to each other through a deformable flexible portion 314. The difference between the two embodiments is that the flexible portion 314 is provided by the clipping arm 120 or independent from the clipping arm 120. The flexible portion 314 can be implemented by a flexible material, or can be implemented by a flexible structure. For example, as shown in the figures, the flexible portion 314 is configured as a meshed strip.

The rigid portion 313 and the flexible portion 314 fit with each other depending on the respective distribution proportions thereof on the clipping arm. In principle, the rigid portion is at least 50% of the total length of the clipping arm in the extension direction of the clipping arm. Further, referring to FIG. 20g, the proportion can be adjusted to 65% or more.

The flexible portion 314 mainly functions to realize the deformation of the rigid portion 313 with respect to the inner frame, that is, switching between the loaded configuration and the released configuration. Referring to FIG. 20i, in the loaded configuration, the clipping arms in each group are close to each other and surround the outer periphery of the inner frame. Referring to FIG. 20h, the clipping arms do not overlap each other in the radial direction of the inner frame, thereby improving the overall profile of the frame in the loaded configuration. From another perspective, the sum of the projection lengths of the clipping arms in the axial direction of the frame is less than or equal to the circumferential length of the frame. In the illustrated embodiment, the projection lengths of the clipping arms in the axial direction of the frame are the same.

Figure 20K:
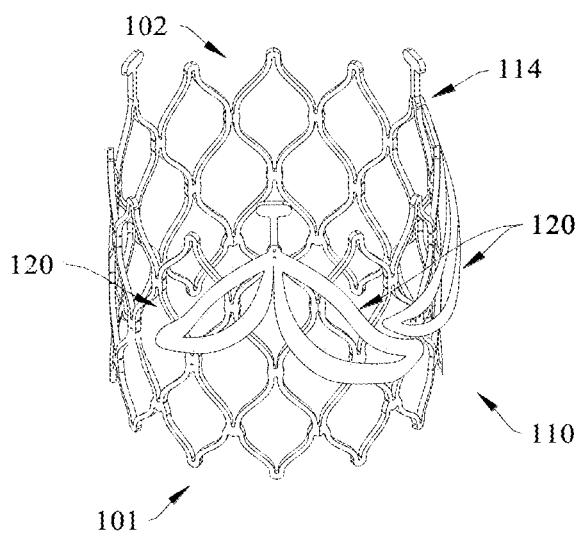
FIG. 20k illustrates an asymmetrical configuration of the reinforced clipping arms.
Figure 21:
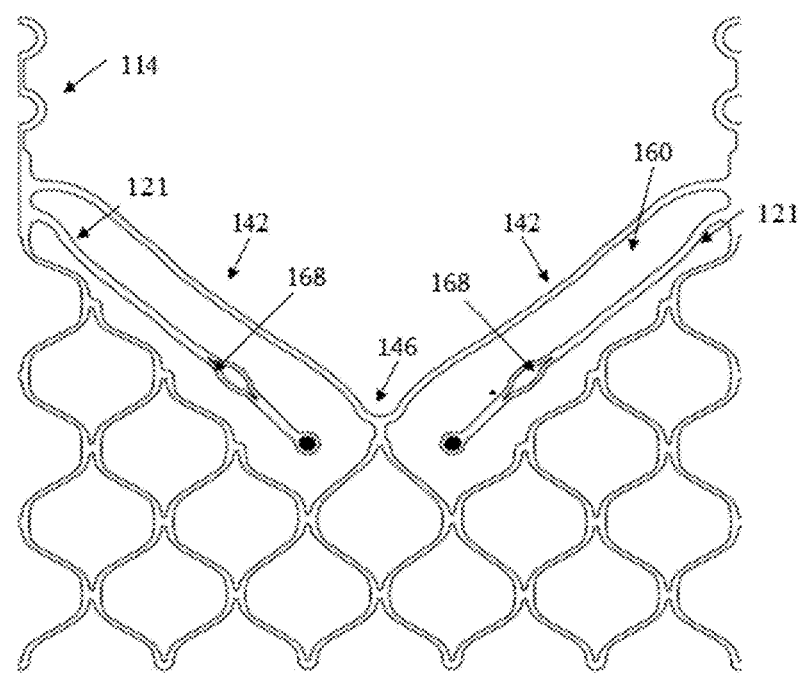
FIG. 21 illustrates a deformable slot in an embodiment.

The plurality of clipping arms 120 can use the same configuration as describe above. Alternatively, the plurality of clipping arms 120 can use different configurations in one embodiment as shown in FIG. 20k. Specifically, two adjacent clipping arms 120 in different groups have different lengths. Further, the clipping arms 120 in each group can be different. For example, the two clipping arms 120 in each group can have different lengths. Besides the difference in the extension length of the clipping arms 120, the free ends of adjacent two clipping arms in different groups can be offset from each other in the circumferential direction of the inner frame. As shown in the figure, the clipping arm 120 has a bent portion adjacent to the free end thereof so as to change the extension path thereof. In the deployed state, the bent portion of one of the adjacent clipping arms surrounds the free end of the other in half, which further improves the positioning of the clipping arms 120 on the native leaflet. This asymmetric arrangement can also be applied to the embodiment shown in FIG. 19m.

An additional part can be further provided on the clipping arm 120. With reference to FIGS. 19f and 19g, each clipping arm 120 is provided with an enlarged positioning structure 311. The positioning structure 311 can facilitate the positioning of the clipping arm 120 on the native valve leaflet 201 and prevent the clipping arm 120 from falling off the valvular sinus 204. Specifically, as shown in FIG. 19g, the positioning structure 311 is provided at the free end 123 of the respective clipping arm 120 and is enlarged by extension of the material of the clipping arm 120 itself. Further, the positioning structure 311 is configured as an enlarged sphere. As shown in FIG. 19f, the positioning structure 311 is configured as a thickened region on the clipping arm 120, specifically at the edge. The positioning structure 311 is provided at a side edge of the clipping arm 120 extending from the fixed end 121 to the free end 123 thereof. In other words, the positioning structure can be provided at the portion of the clipping arm 120 which is configured to contact the floor or edge of the sinus of the native leaflet 201. The specific form of the positioning structure 311 can be a positioning sphere, a positioning flange, a positioning bump, or the like. Alternatively, referring to FIG. 19h, different positioning structures 311 can be provided on the same clipping arm 120, which cooperate with each other.

In addition to the positioning structure 311, referring to FIG. 19i and FIG. 19j, each of the clipping arms 120 can be covered with a sleeve 3120, which can use a braided structure or be formed in one piece. The sleeve 3120 can provide more functions for the clipping arm 120. For example, the sleeve 3120 can be made of a biocompatible polymer material. In this embodiment, the sleeve 3120 enables the surrounding tissue to be attached and fixed to the clipping arm 120, thereby further improving the positioning effect. For another example, the sleeve 3120 can be provided with a drug-loading space. The drug-loading space can be a separate space, or can be a gap(s) in the sleeve 3120 of the braided structure as mentioned above. In this embodiment, the sleeve 3120 can facilitate the treatment by applying drug. Referring to FIG. 19j, the sleeve 3120 and the positioning structure 311 as described above can be provided on the same clipping arm 120, which cooperate with each other.

Similar to the other clipping arms 120, referring to FIG. 20a, the line connecting the center P1 of the fixed end 121 and the center P2 of the free end 123 of each clipping arm 120 is defined as the clipping path which is not coplanar with the axis of the inner frame 110. When fitting the native valve leaflet 201, as shown in FIG. 20b, the increased size of the clipping arm 120 can better fit the anatomic structure of the valvular sinus 204, thereby achieving a better positioning effect.

Referring to FIGS. 20c to 20f, the present application discloses a prosthetic heart valve device with reinforced clipping arms 120, including a frame 110 as described above and valve leaflets 200, wherein the leaflets 200 are connected with the frame 110 and configured to be located within the blood flow passage 301. The leaflets 200 cooperate with each other for opening or closing the blood flow passage 301.

The inner and/or outer sides of the inner frame 103 can be further provided with a covering film 220. The two leaflets 200 adjacent in the circumferential direction are connected to a joining region 211 on the inner frame 103, and the commissure region 114 corresponds to a corresponding joining region 211 in the circumferential direction of the inner frame 103.

The leaflets 200 and the covering film 220 can be any known repair material including processed animal tissue, such as pig tissue and bovine tissue, or synthetic material. The leaflets 200 and the covering film 220 can be attached to the frame 110 by conventional stitching.

Figure 22A:
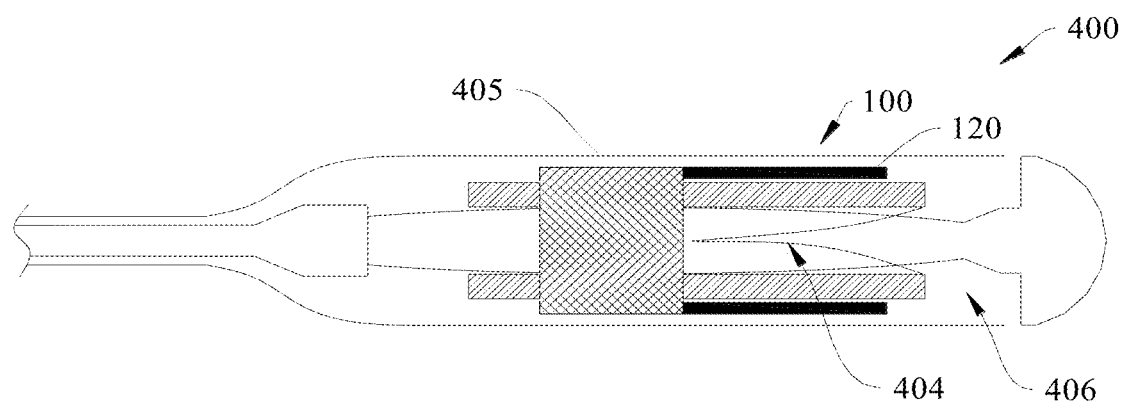
FIG. 22a to FIG. 22c are views illustrating different operations of the delivery system according to an embodiment.
Figure 22B:
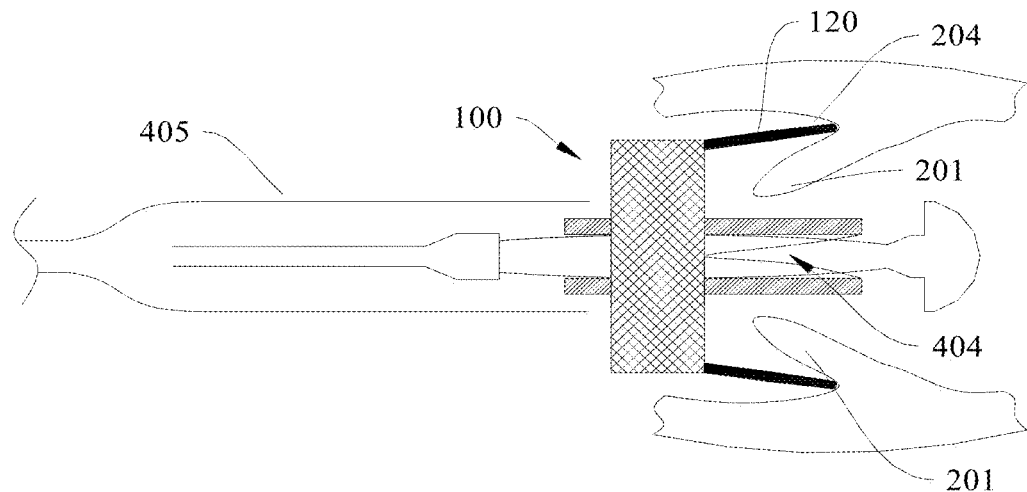
Figure 22C:
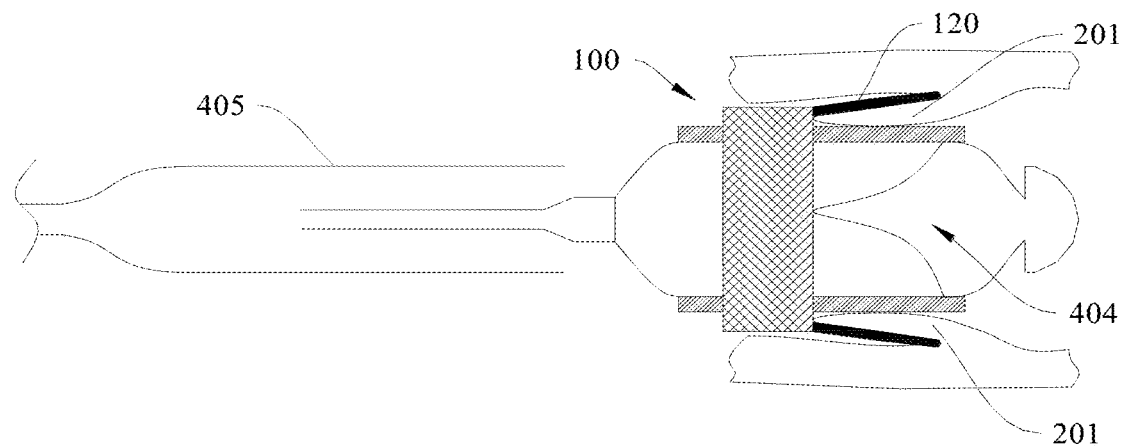

Referring to FIGS. 22a to 22c, the present application further discloses a delivery system 400 for a prosthetic heart valve device 100, including:
 a support device 404 that is switchable between the inflated and deflated configurations under fluid; and
 an outer sheath 405 that is slidably engaged with the periphery of the support device 404, the radial gap between the outer sheath 405 and the support device 404 being a loading zone 406 for receiving the prosthetic heart valve device 100 in the compressed configuration.

Referring to FIG. 23a to FIG. 24d, the present application further discloses a positioning method for the prosthetic heart valve device 100 for positioning any of the prosthetic heart valve devices 100 as described above, and the positioning method includes:
 delivering the prosthetic heart valve device 100 to a predetermined site by a delivery system 400, in which the inner frame 103 is in a compressed configuration, the clipping arms 120 are in a loaded configuration, and the support device 404 is in a deflated configuration;
 driving the outer sheath 405 to release the free ends 123 of the clipping arms 120, thereby expanding the free ends 123 of the clipping arms 120 and thus transforming into the transition configuration;

adjusting the position of the inner frame 103 such that the free end 123 of the at least one clipping arm 120 is located outside the native leaflet 201; and driving the support device 404 to the inflated configuration and releasing the inner frame 103 and the fixed ends 121 of the clipping arms 120, so that the inner frame 103 transforms into the expanded configuration and the clipping arms 120 transform into the released configuration.

Optionally, before adjusting the position of the inner frame 103, the support device 404 is driven to a pre-inflated configuration, so that the inner frame 103 transforms into an intermediate configuration between the compressed configuration and the expanded configuration, and the clipping arms 120 transform into an intermediate configuration between the loaded configuration and the released configuration so as to achieve precise adjustment of the position of the inner frame 103.

The specific positioning method is explained in detail below with reference to the drawings.

Figure 23A:
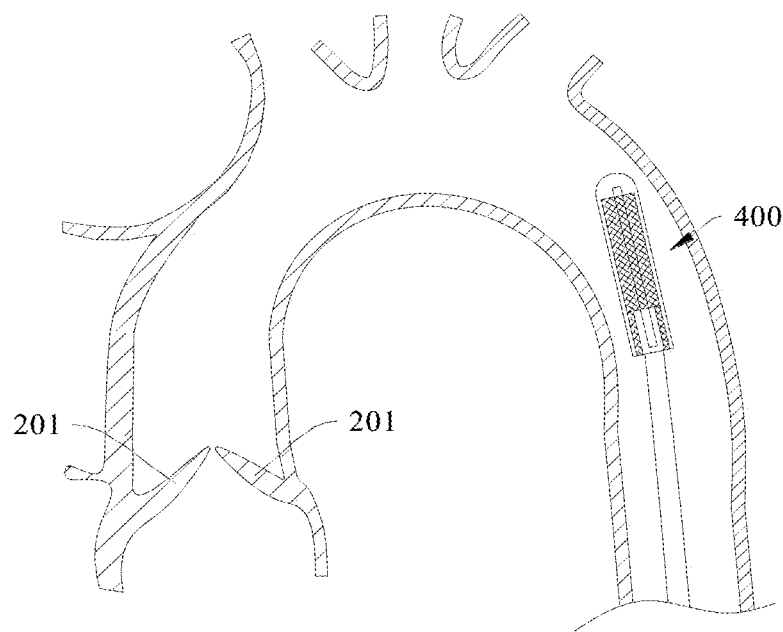
FIGS. 23a to 23g are views illustrating the operations of the delivery system according to an embodiment.
Figure 23B:
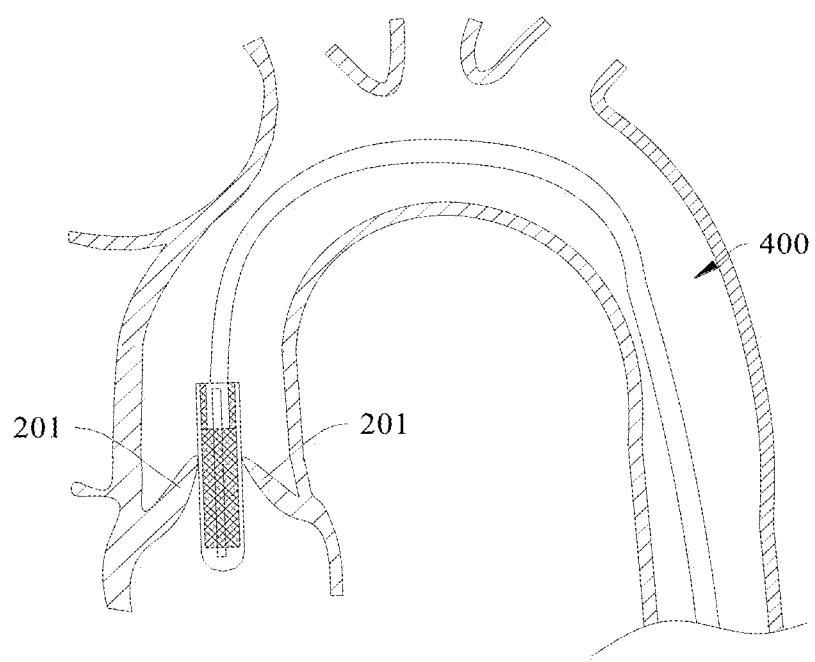

Referring to FIGS. 23*a* and 23*b*, the delivery device delivers the inner frame 103 in a compressed configuration and the clipping arms 120 in a loaded configuration to a predetermined site. As shown in the figures, the delivery device passes through the native leaflets 201 after entering the target from the aortic arch. The specific puncture path can include the aortic or femoral artery or other feasible location.

Figure 23C:
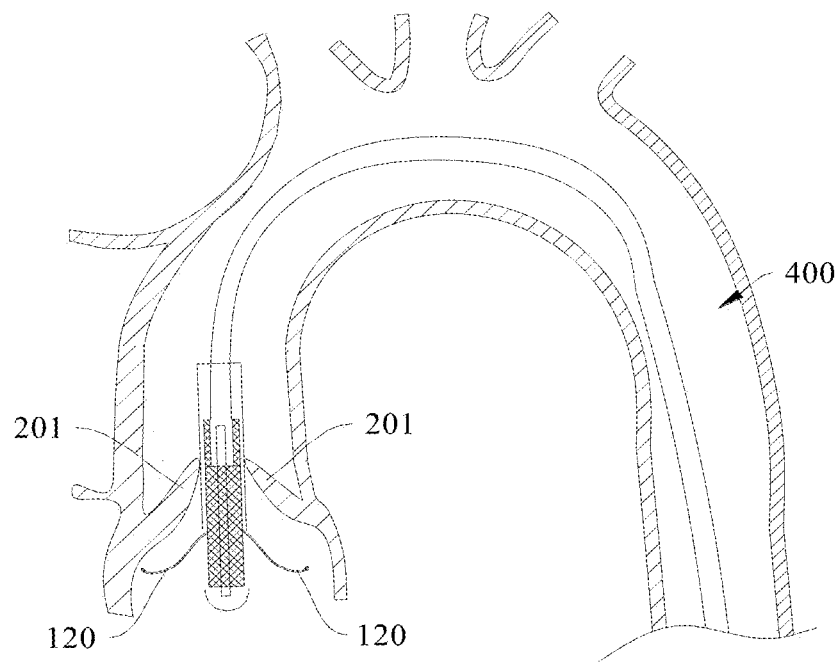
Figure 23D:
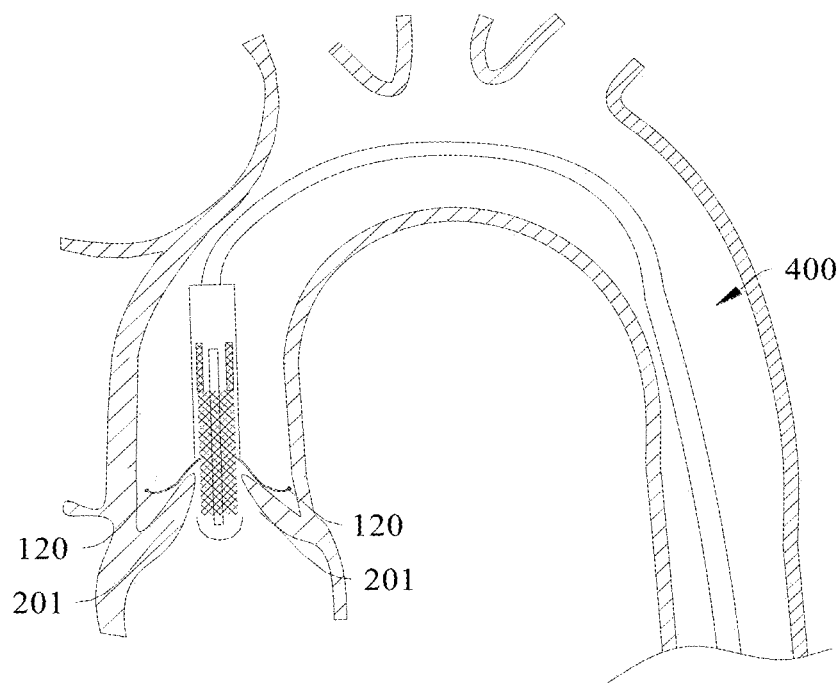

Referring to FIGS. 23*c*-23*d*, the delivery device releases the clipping arms 120, causing the free ends 123 of the clipping arms 120 to expand and thus transforming into the transition configuration. In this embodiment, the clipping arms 120 extend at the inflow end 101 of the native leaflets 201.

Figure 23E:
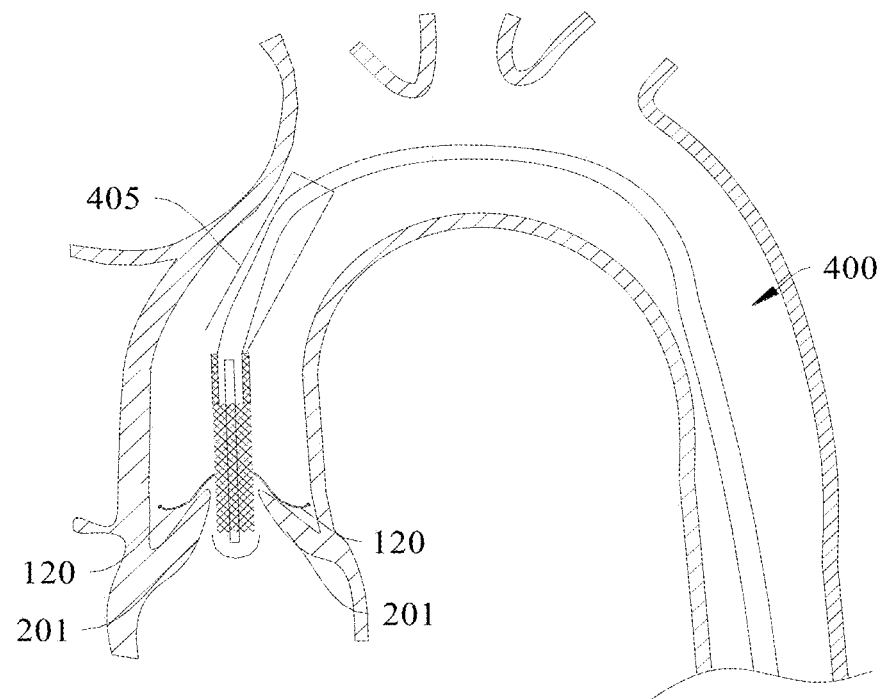

Referring to FIG. 23*e*, the position of the frame 110 is adjusted such that the free ends 123 of the clipping arms 120 are located just outside the native leaflets 201 while the inner frame 103 is located inside the native leaflet 201. In this embodiment, the position of the frame 110 is adjusted by withdrawing the delivery assembly, so as to improve the engagement of the clipping arms 120 and the native leaflets 201.

Figure 23F:
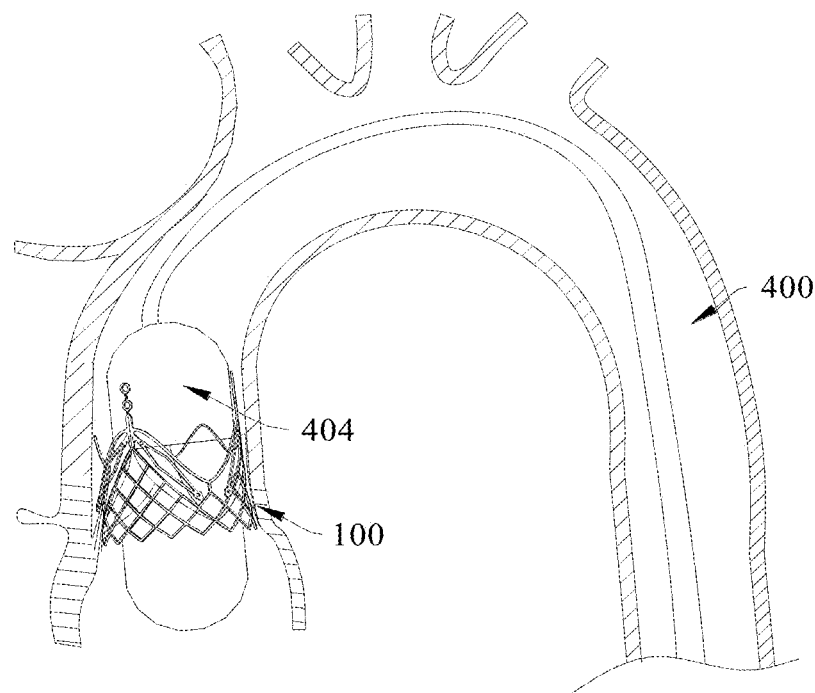

Referring to FIG. 23*f*, the support device 404 is driven to the inflated configuration, the inner frame 103 and the fixed ends 121 of the clipping arms 120 are released, so that the inner frame 103 transforms into the expanded configuration, and the clipping arms 120 transforms into the released configuration, wherein the inner frame 103 cooperates with at least one clipping arm 120 to hold the native leaflets 201.

Figure 23G:
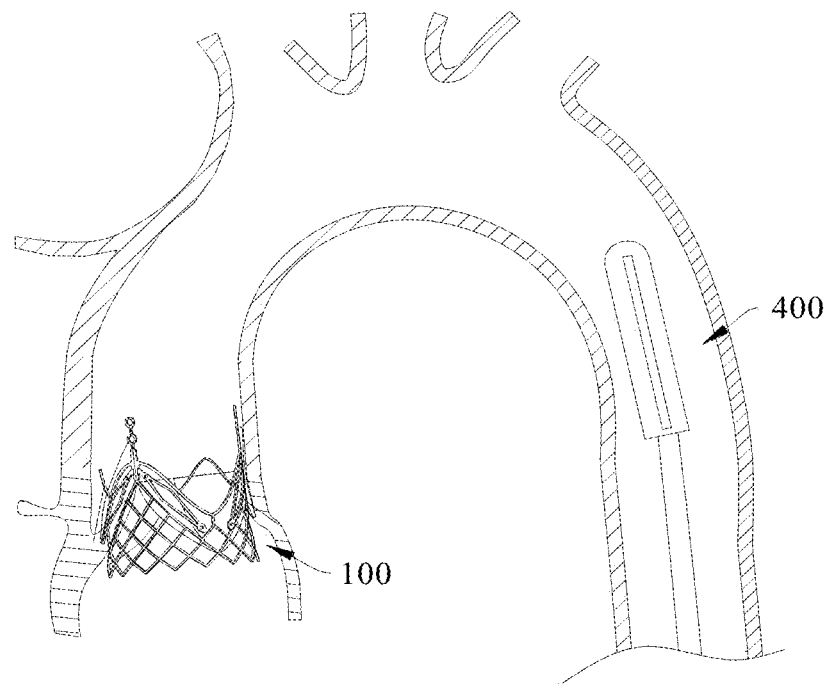
Figure 24A:
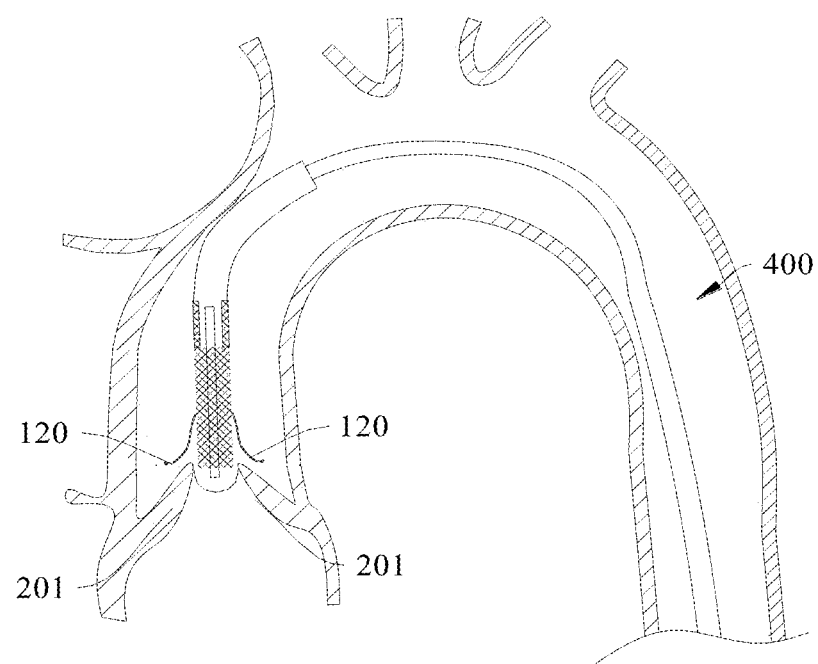
FIG. 24a to FIG. 24d are views showing the pre-expansion of the delivery system.
Figure 24B:
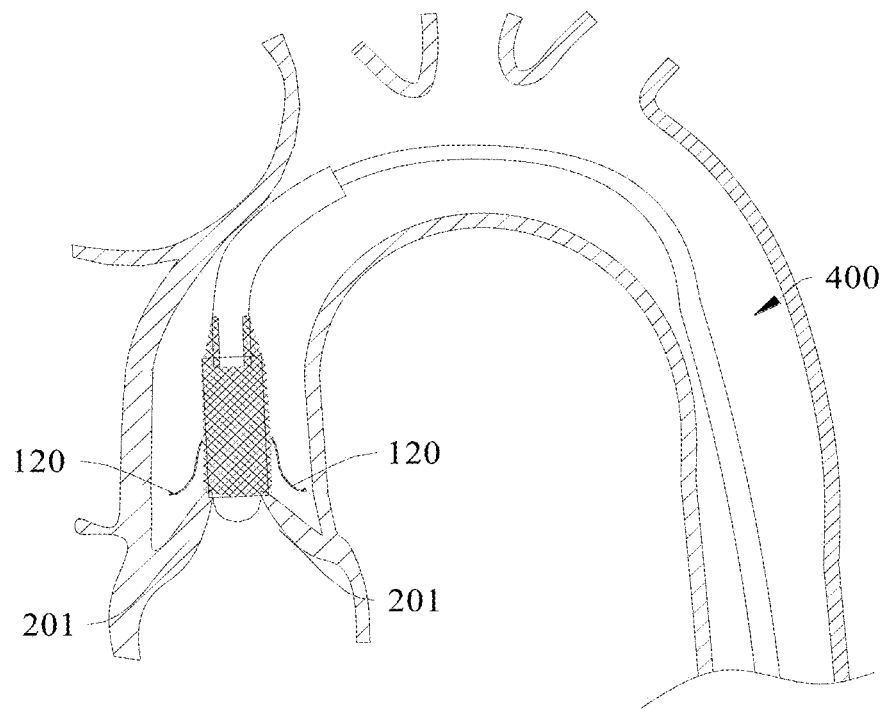
Figure 24C:
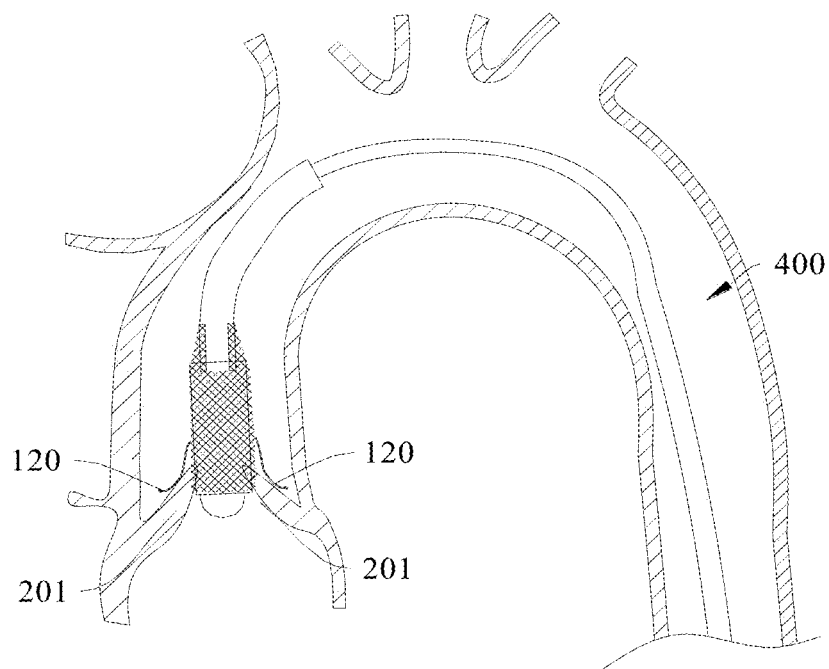
Figure 24D:
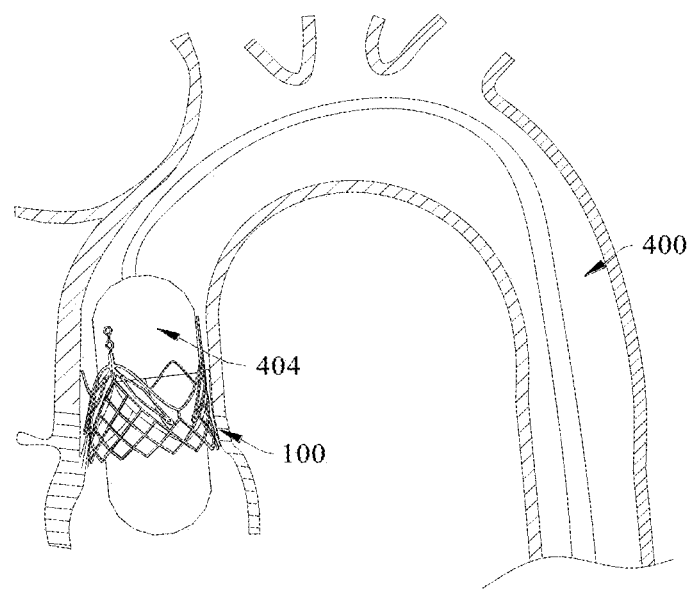
Figure 25:
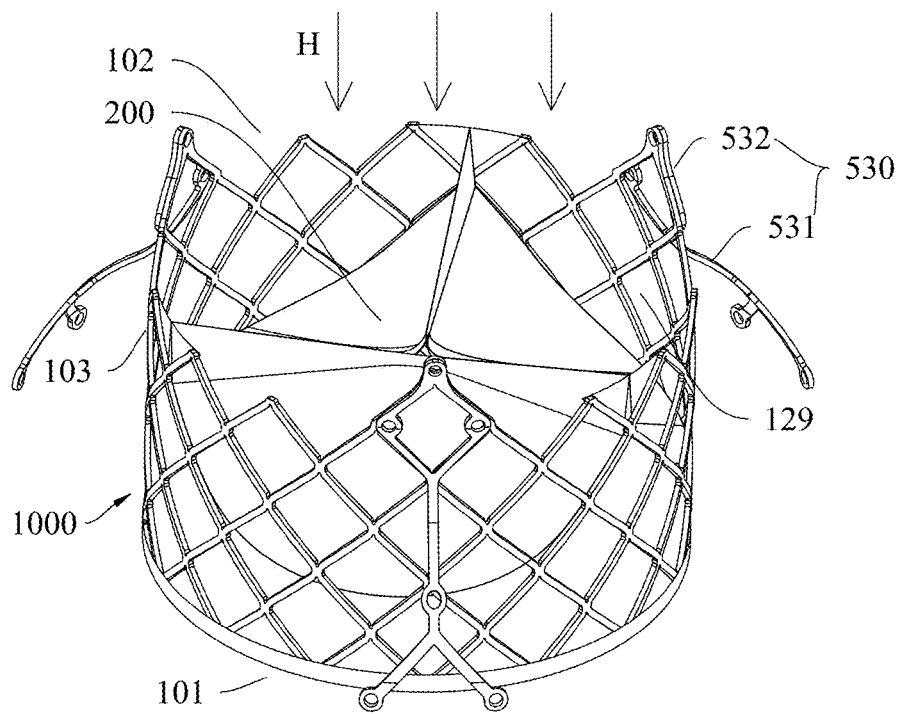
FIG. 25 is a perspective view of a prosthetic aortic valve device according to an embodiment.
Figure 26:
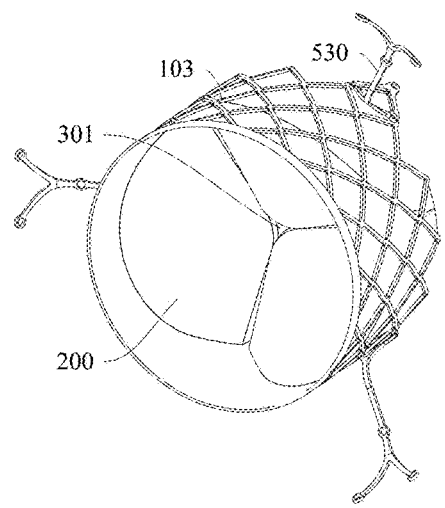
FIG. 26 is a perspective view of the prosthetic aortic valve device of FIG. 25 in another view.
Figure 27:
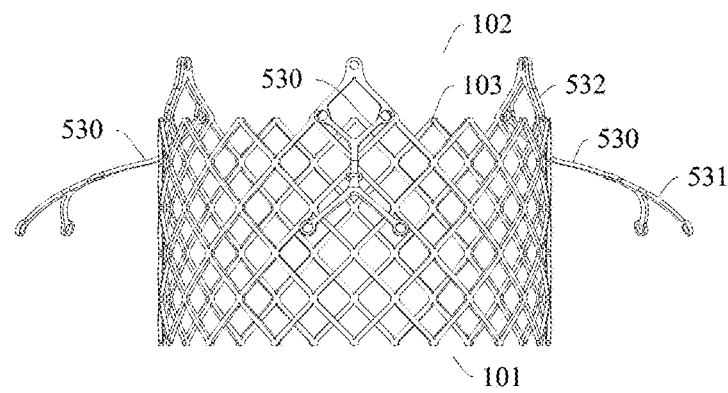
FIG. 27 is a front view of the inner frame of the prosthetic aortic valve device of FIG. 26 in the released configuration in the form of a straight cylinder (with leaflets not shown).

Referring to FIG. 23*g*, the support device 404 is withdrawn and the delivery device is withdrawn. The transcatheter surgery is finished.

During the surgery, the expansion of the inner frame may affect the positioning of the clipping arms, which can be alleviated through specific operations.

Referring to FIGS. 24*a* to 24*d*, prior to adjusting the position of the inner frame 103, the support device 404 is driven to a pre-inflated configuration so that the inner frame 103 transforms into an intermediate configuration between the compressed configuration and the expanded configuration, and the clipping arms 120 transform into an intermediate configuration between the loaded configuration and the released configuration so as to achieve precise adjustment of the position of the inner frame 103. The inner frame 103 in the intermediate configuration allows to release the clipping arm 120 to a great extent, so that the intermediate configuration of the clipping arms 120 prior to adjusting the position of the inner frame 103 are closer to the completely released configuration thereof, thereby improving the positioning effect of the frame 110.

Referring to FIGS. 25*a*-33*c*, an embodiment of the present application provides a prosthetic aortic valve device 1000 having opposite inflow end 101 and outflow end 102, the prosthetic aortic valve device 1000 including:

an inner frame 103 having a meshed cylindrical structure, which is radially deformable and has relative compressed and expanded configurations after being subjected to an external force, wherein the interior of the inner frame 103 is configured as an axially through blood flow passage 301, and the countercurrent blood flows in the direction H as shown in the figure;

leaflets 200 (prosthetic leaflets, in an opened state in FIG. 26) connected to the inner frame 103, wherein the leaflets 200 include three leaflets and cooperate with each other to control the opening and closing of the blood flow passage 301; and three guiding members 530 as the positioning mechanism arranged in sequence in the circumferential direction of the inner frame 103 (the number of which corresponds to that of the aortic valvular sinuses), and the position thereof respectively aligned with the area where the leaflets 200 are located in the circumferential direction, wherein each guiding member 530 includes a root 532 fixedly connected with the inner frame 103 and a wing 531 extending from the root 532 further towards the inflow end 101, the guiding member 530 is made of a memory material and is configured to be switchable between a loaded configuration, a transition configuration, and a released configuration.

As shown in FIG. 29 and FIG. 31, in the loaded configuration, the inner frame 103 assumes the compressed configuration and the guiding members are radially pressed to contact or be close to the inner frame 103 in the compressed configuration, so that the inner frame 103 and the guiding members can be easily surrounded by the sheath and delivered in vivo.

Figure 32:
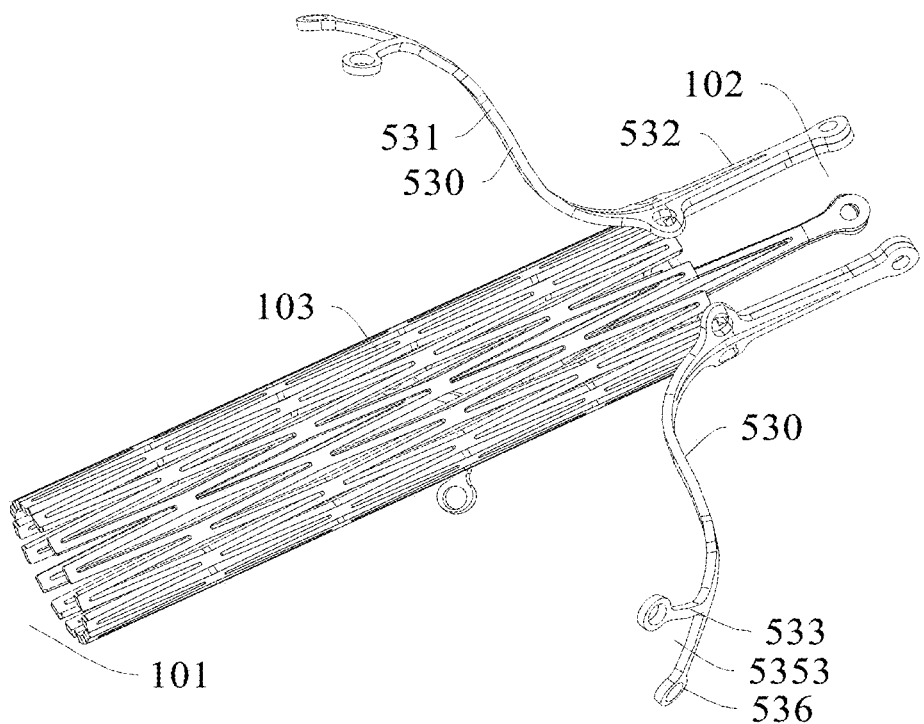
FIG. 32 is a perspective view of the prosthetic aortic valve device of FIG. 30.

As shown in FIGS. 30 and 32, in the transition configuration, the inner frame 103 remains in the compressed configuration, and the roots 532 of the guiding members 530 remain gathered to adapt the compressed configuration of the inner frame 103. The wings 531 are self-deformed and thus extend outside of the inner frame 103, with a first receiving space formed between the outer wall of the inner frame 103 and the wings 531 for receiving the native leaflets 201. As the circumferential position of the guiding members 530 are respectively aligned with the area where the leaflets 200 are located (i.e., located within the one-third circumferential area where the corresponding leaflet is located), the extended wings 531 can be adjusted in position to enter the corresponding valvular sinuses, thereby achieving the circumferential positioning of the inner frame 103, with the inner frame 103 inside the native leaflets and the wings 531 outside the native leaflets.

Figure 33A:
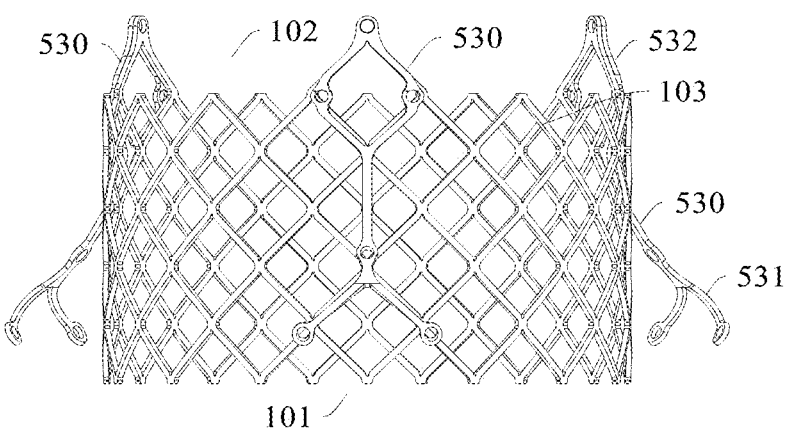
FIG. 33a is a front view of the prosthetic aortic valve device in a released configuration in one embodiment.
Figure 33B:
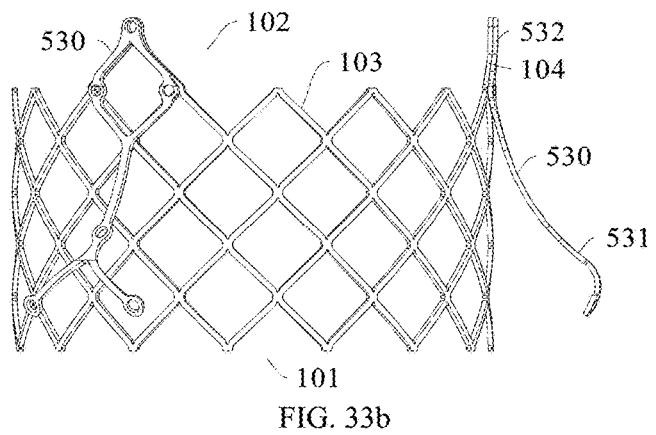
Figure 33C:
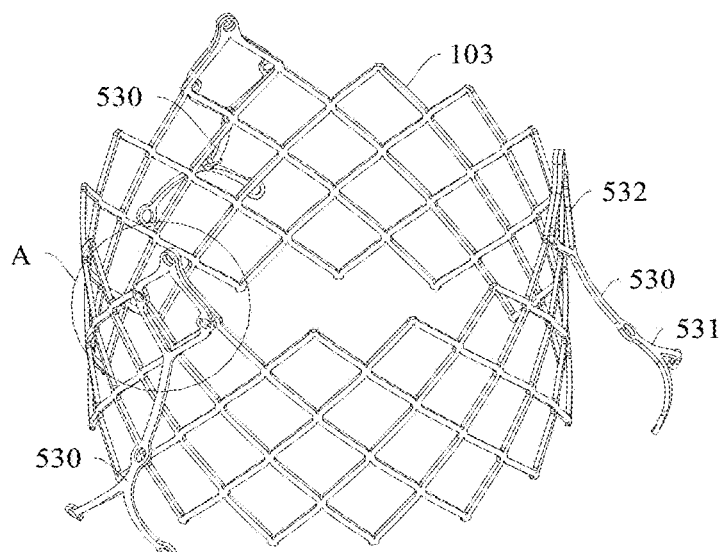

As shown in FIGS. 33*a* to 33*c*, in the released configuration, the inner frame 103 is already transformed into the expanded configuration after being subjected to an external force, and the roots 532 of the guiding members 530 move away from each other to adapt the expanded configuration of the inner frame 103. A second receiving space is formed between the wings 531 and the outer wall of the inner frame 103, and the at least one native leaflet is clipped in the second receiving space when the positioning is accurate.

In the present application, unless otherwise specified, the shape and position of the guiding member 530 are described referring to its released configuration, and the shape and position of the inner frame 103 are described referring to its expanded configuration.

The inner frame 103 has a meshed cylindrical structure, which can be radially deformed to facilitate the intervention after compression and the subsequent expansion and release. The axial length of the inner frame 103 may change when the inner frame 103 is radially deformed. The meshed cylindrical structure is configured to be expanded by external force, i.e., the meshed cylindrical structure is not made of self-expandable material. In general, the inner frame can be expanded by balloon. However, the guiding member 530 is made of a memory material (e.g., pre-heat-set nickel-titanium alloy), the wing 531 of which can be released in the human body first, the root 532 of which can be considered as a portion where the guiding member 530 and the inner frame 103 are adjacent and connected to each other. The specific shape is not strictly limited. The root 532 and the wing 531 can be formed in one piece to facilitate processing. The wing 531 extends outward relative to the inner frame 103 after release, and by adjusting the posture of the inner frame 103, the wing 531 can enter into the valvular sinus 204 to pre-position the inner frame 103 in the circumferential direction, and then the inner frame 103 can be released and expanded by balloon. Because the guiding members 530 are aligned with the area where the valve leaflets 200 are located, the junction of adjacent valve leaflets 200 avoids the coronary artery orifice and prevents the blood flow from being obstructed. In addition, the wings 531 abut against the sinus floors of the valvular sinuses 204, which positions the inner frame 103 in the axial direction to avoid slipping to the left ventricle side under the action of the reverse flow of blood.

Referring to FIGS. 33*a*-33*c* and 39*a*-39*d*, based on the circumferential positional relationship between the guiding members 530 and the region where the leaflets 200 are located, it can be considered that an embodiment of the present application provides a prosthetic heart valve device having opposite inflow and outflow ends. The prosthetic heart valve device includes an inner frame 103 and leaflets 200, wherein the inner frame and the leaflets can use conventional techniques or embodiments described herein. The prosthetic heart valve device further includes a positioning mechanism. The positioning mechanism includes a root connected to the inner frame and a wing extending from the root towards the inflow end. The wing is extendable in the peripheral region of the inner frame, with a receiving space defined between the wing and the outer wall of the inner frame for allowing the entry of the native leaflet. The positioning mechanism is used to be placed at the corresponding valvular sinus in the human body to perform positioning. In other embodiment, various guiding members can be employed, without strictly limiting the various configurations and the transformations.

In this embodiment, the focus is that the positioning mechanism is arranged along the circumferential direction of the inner frame, and connected with the inner frame at a plurality of connections, each of which is located between two adjacent commissure regions in the circumferential direction of the inner frame. For example, in the case where the positioning mechanism includes a plurality of guiding members, the guiding member includes a root connected to the inner frame and a wing extending from the root towards the inflow end, and the root of each guiding member is located between two adjacent commissure regions in the circumferential direction of the inner frame.

Figure 47:
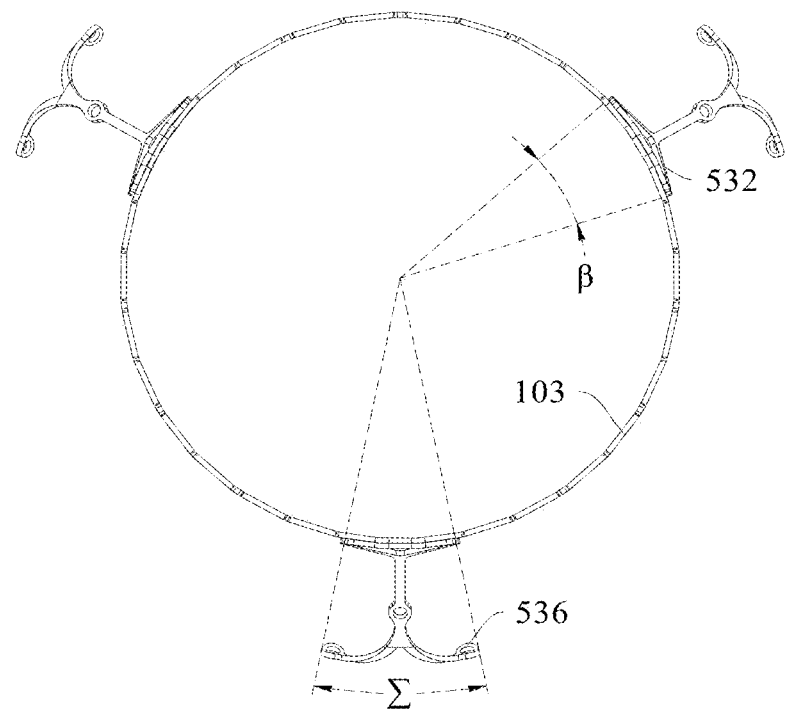

In order to position the inner frame 103 in space correctly and reduce the displacement after the inner frame 103 is positioned in place, the guiding member 530 needs to have a suitable circumferential span (referring to the description of FIG. 47 herein).

As one of the functions of the positioning mechanism is to clip the native leaflet, the position of the root affects the clipping strength to a certain extent. In this embodiment, the root is located between two adjacent commissure regions in the circumferential direction of the inner frame, and generally corresponding to the middle of the sinus or native leaflet. Compared to the embodiments with clipping arms extending from the commissure regions and provided with the same clipping force, the present embodiment has a low structural strength requirement.

Further, the guiding member can extend from the root to the free end over the shortest path to reduce the overall extension length, which is beneficial to control the radial dimension after compression to ensure the necessary compliance during intervention.

Figure 34:
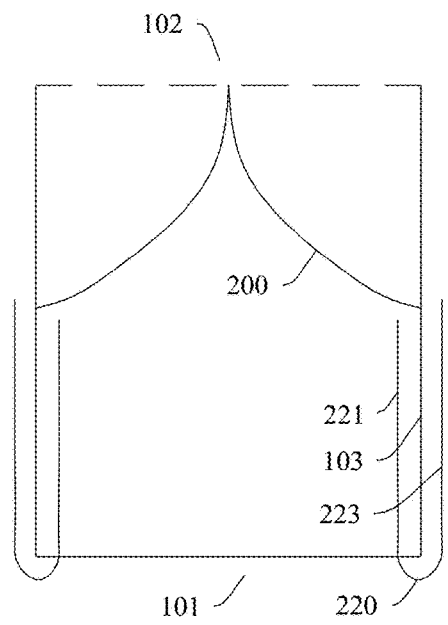
FIG. 34 is a view showing the positional relationship between the covering film and the inner frame in the prosthetic aortic valve device.
Figure 35A:
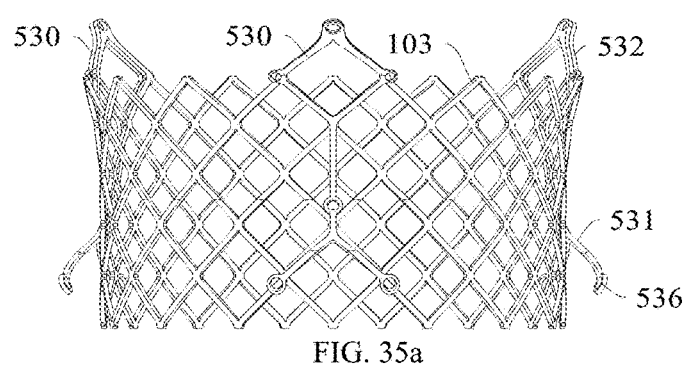
FIG. 35a is a front view of the flared frame of the prosthetic aortic valve device in one embodiment.
Figure 35B:
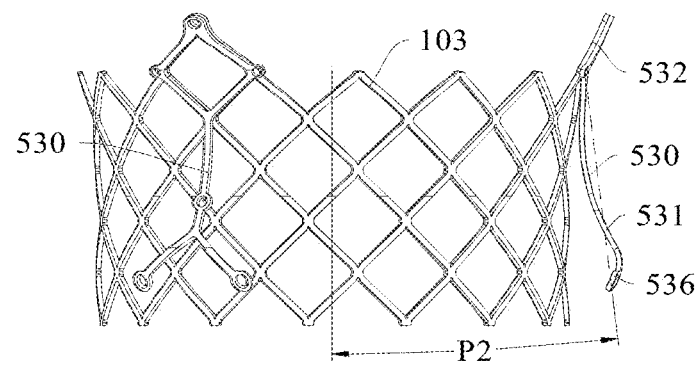
Figure 35C:
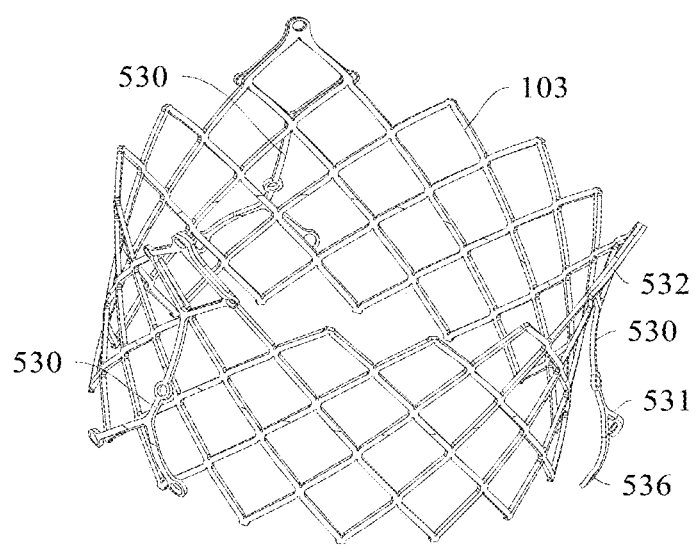
FIG. 35c is a perspective view of the prosthetic aortic valve device of FIG. 35b.

Referring to FIG. 34, in order to construct the blood flow passage and better fit with the surrounding tissue, the prosthetic aortic valve device 1000 further includes a covering film 220, which can include one or both of an inner covering film 221 and an outer covering film 223. The inner covering film 221 is fixed to the inner wall of the inner frame 103 and connected with the edge of the leaflets 200 at the inflow end 101, and the outer covering film 223 is fixed to the outer wall of the inner frame 103. Furthermore, the covering film 220 avoids the projection areas 129 of the leaflets 200 on the side wall of the inner frame.

FIGS. 29 to 35*c* show the postures of the guiding members 530 in different configurations in the radial direction of the inner frame 103. In the loaded configuration, the guiding member 530 has the same diameter in the axial direction from the root 532 to the wing 531. In the transition configuration, the radial position of the root 532 of the guiding member 530 is unchanged, while the wing 531 is turned radially outward. In the released configuration, the guiding member 530 extends outwardly from the root 532 as the inner frame 103 expands, wherein the guiding member 530 extends radially outwardly and then is bent inwardly.

The guiding members 530 are made of a memory alloy, such as a pre-heat-set nickel-titanium alloy the shape of which corresponds to the released. The guiding member 530, at room or in-vivo temperature, has an internal stress in both the loaded configuration and the transition configuration relative to the released configuration. This internal stress urges the inner frame 103 and the guiding member 530 to switch to the final configuration in the body, and can be gradually eliminated as the inner frame 103 expands, so that the inner frame 103 and the guiding member 530 are better maintained in the final configuration. In the released configuration, the axial length of the guiding member 530 is 40% to 80%, for example, 50%, of the entire length of the inner frame 103.

The frame 110 generally includes the inner frame 103 and the guiding members 530. One end of the guiding member 530 away from the inner frame 103 is configured as the free end 536, and the root 532 can be regarded as a fixed end opposite to the free end 536.

In the loaded configuration, the wing 531 contacts the outer side of the inner frame 103. In the transition configuration, an angle P1 is defined between the wing 531 (referring to the line connecting the two ends of the wing) and the axis of the inner frame.

In the released configuration, the free end of the wing is closer to the out wall of the inner frame, with an angle P2 defined between the wing 531 and the axis of the inner frame, where P1 is great than p2. For example, P1 satisfies 30 to 60 degrees, and P2 satisfies 5 to 30 degrees. The free end of the wing closer to the outer wall of the inner frame can be caused by the outflow end of the inner frame turning outward, and by the shaping of the guiding member itself, separately or in combination. That is, the second receiving space would become smaller relative to the first receiving space.

As shown in FIG. 28*a* and FIG. 28*b*, after the inner frame 103 is released, the inner frame 103 is still in a straight cylindrical shape, and an angle P3 is defined between the wing 531 and the axis of the inner frame, where P3<P1. The posture of the wing 531 shown in the figure is only for illustration, which does not strictly limit the angle.

As shown in FIGS. 36*a* to 36*d*, the inner frame 103 is formed by cutting a pipe material, and the material (for example, stainless steel) is suitable for balloon expansion release. The inner frame 103 has a straight cylindrical shape in the loaded configuration.

Figure 38A:
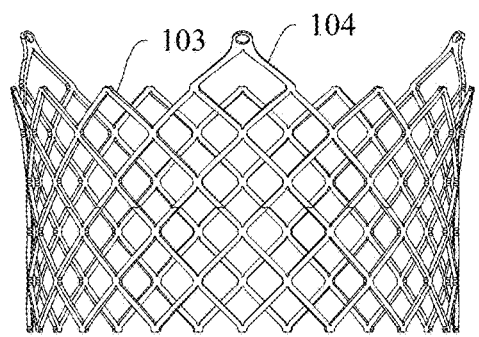
FIGS. 38a to 38d are respectively a front view, a left side view, a perspective view and a top view of the flared inner frame of the prosthetic aortic valve device in an expanded configuration.
Figure 38B:
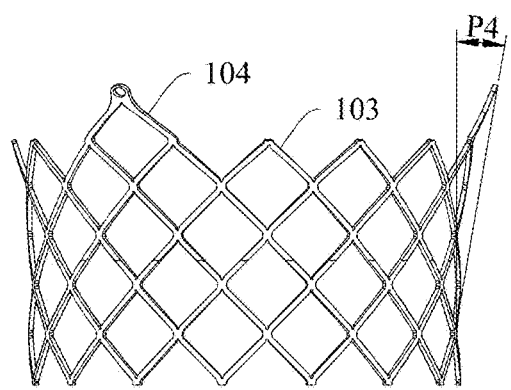
Figure 38C:
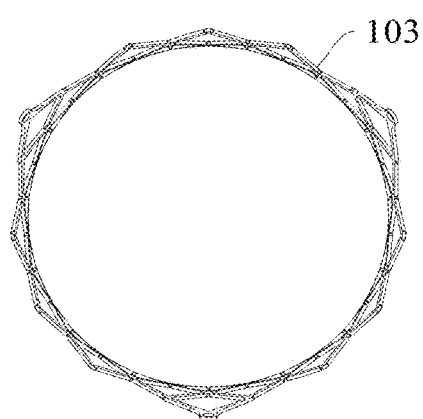
Figure 38D:
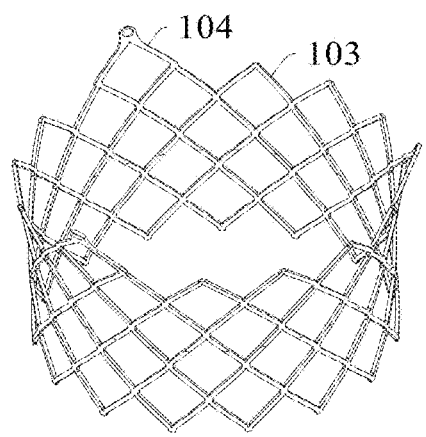

As shown in FIGS. 38*a* to 38*d*, in another embodiment, the outflow end 102 of the inner frame 103 is flared outward with respect to the axis, wherein the turning angle is P4 as shown in FIG. 38*b*, and P4 satisfies 0 degree<P4<45 degrees, such as 5 to 25 degrees.

The outflow end 102 slightly turning outward causes the free ends of the wings 531 to be closer to the inner frame 103 to clip the native leaflets and thus improve the positioning. The outflow end 102 can be flared by the balloon. For example, when the balloon extends beyond the outflow end of the inner frame 103, the balloon is released and thus tends to expand outward, thereby driving the outflow end 102 to turn outward. In the case where the axial length or the turning angle for the turning portion is further increased, the frame 110 can be shaped to turn outward directly using the expanded end portion of the balloon.

Figure 39A:
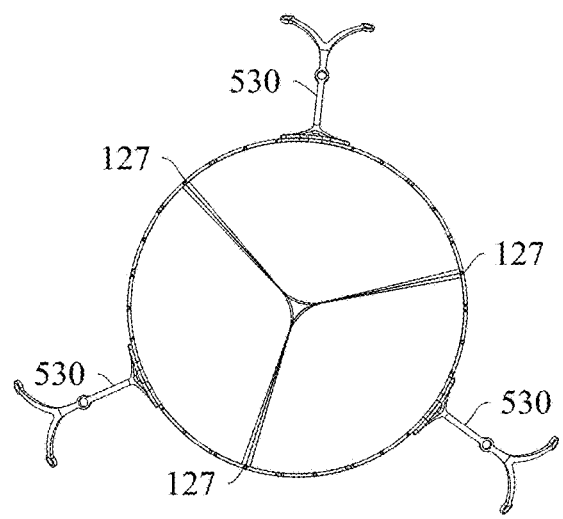
FIG. 39a is a top view of the prosthetic aortic valve device in a released configuration in one embodiment.

In order to fix the guiding member 530, as shown in FIG. 39*a*, two adjacent leaflets 200 are connected on the inner frame 103 at the commissure region 127 of the inner frame 103, and the root 532 of the guiding member 530 is located between two adjacent commissure regions 127, but is not limited to being strictly centered therebetween.

Figure 39B:
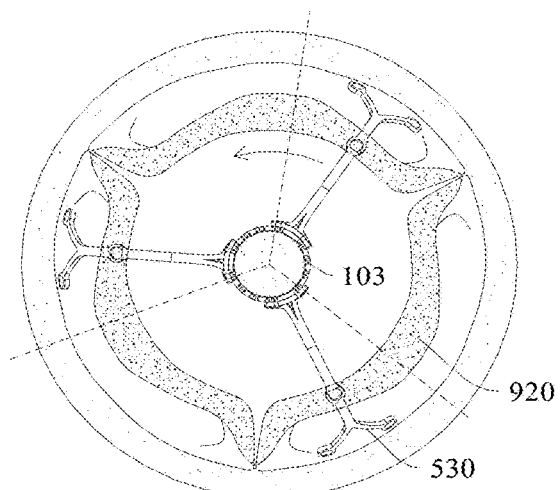
FIG. 39b is a view of the prosthetic aortic valve device and the aortic valve prior to circumferential positioning therebetween.
Figure 39C:
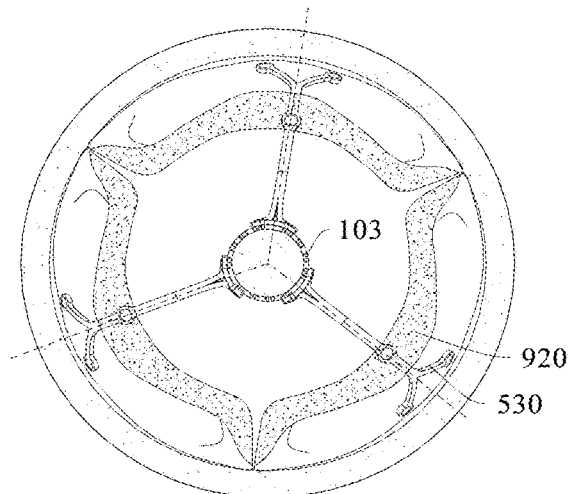
FIG. 39c is a view of the prosthetic aortic valve device and the aortic valve after circumferential positioning therebetween.

The guiding member 530 is generally configured as a bar. Each guiding member 530 is formed in one piece and switches the configurations thereof based on its own elastic deformation. Compared with a hinge structure, the internal stress of the guiding member of the present application can be used as the driving force for deformation. Referring to FIGS. 39*b* and 39*c*, after release of the guiding members 530, there may be deviations in the circumferential positions of the guiding members 530 from the positions of the valvular sinuses 204. For example, the areas represented by the three radially extending solid lines can be regarded as the approximate distribution regions of the three guiding members, while the areas represented by the three radially extending dotted lines can be regarded as the approximate distribution regions of the three valvular sinuses, which are not aligned with each other as shown in FIG. 39*b*, in which case, the inner frame 103 can be rotated in the direction of the solid arrow shown in the figure to drive the guiding members 530 until the three radially extending solid lines coincide with the dashed lines, so as to achieve circumferential alignment as shown in FIG. 39*c*.

Figure 40C:
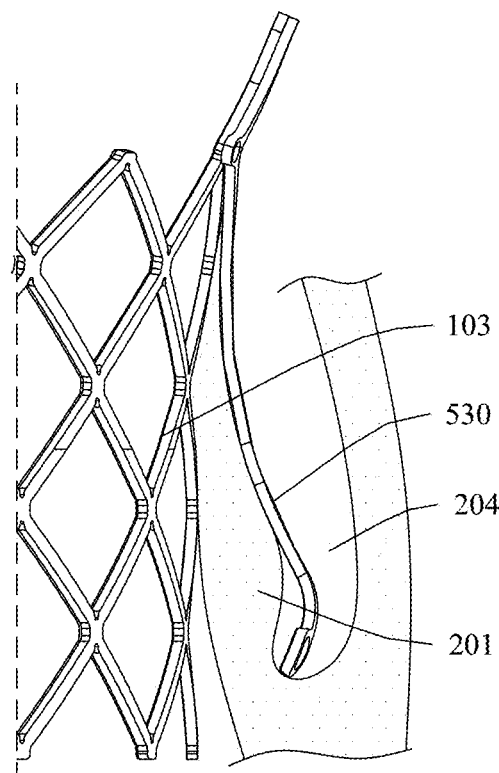
FIG. 40c illustrates the guiding member being positioned in the valvular sinus after released.
Figure 41A:
FIGS. 41a to 41c are respectively a front view, a perspective view and a right side view of a guiding member in a loaded configuration.
Figure 41B:
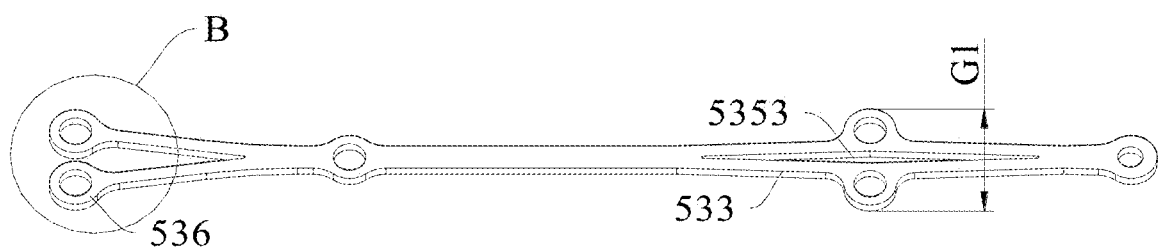
Figure 41C:
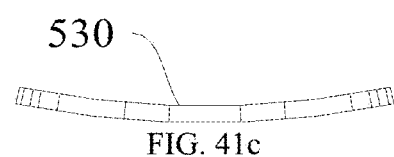
Figure 42A:
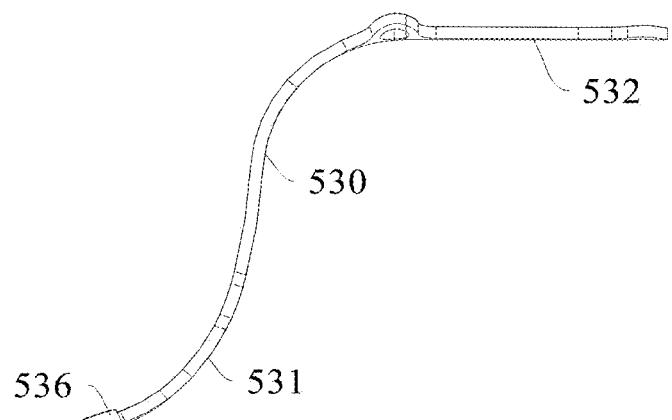
FIGS. 42a to 42c are respectively a front view, a perspective view and a right side view of the guiding member in a transition configuration.
Figure 42B:
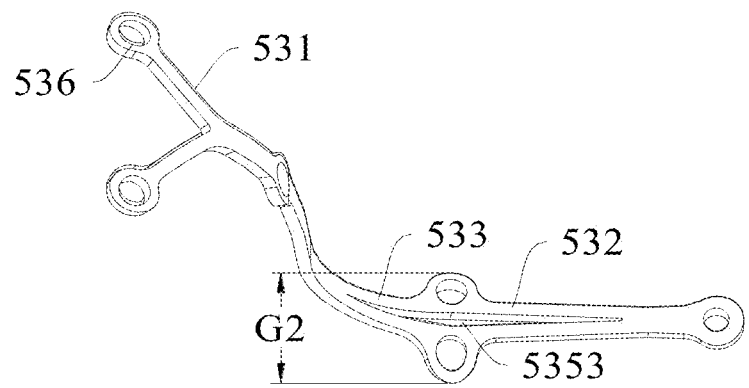
Figure 42C:
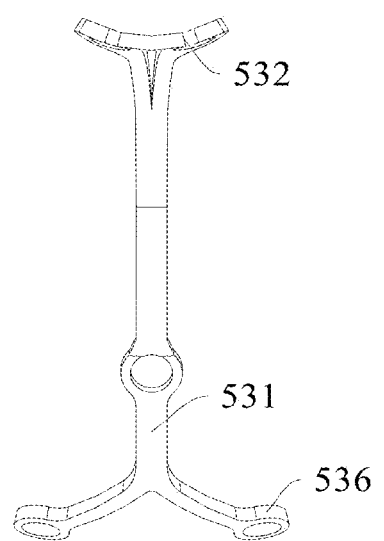

After circumferential alignment, the inner frame 103 is moved towards the inflow end until the guiding members 530 abut against the sinus floors of the valvular sinuses 204 or the native leaflets have filled the receiving space between the inner frame 103 and the guiding members 530 to achieve positioning. FIG. 39*d* show the axial position, and FIGS. 40*a* to 40*c* show the radial position, wherein the native leaflet 201 is located between the guiding member 530 and the inner frame 103. The inner frame 103 can be then released and expanded by balloon, thereby avoiding the coronary artery.

Referring to FIG. 40*b*, when the balloon 630 is expanded, the ends of the inner frame 103 first tend to turn over, during which process, the free ends of the guiding members 530 will tend to move inward and begin to clip the native leaflets 201. The inner frame 103 is completely released radially at the later stage of the balloon expansion. As shown in FIG. 40*c*, since the root of the guiding member 530 deforms circumferentially with the deformation of the inner frame, the free end of the guiding member 530 is further moved towards the inner frame 103 to clip the native leaflet. The mechanism of deformation of the guiding member 530 is further described below.

Referring to FIGS. 41*a*-44, the wing 531 is a branched structure 535 adjacent to the root 532, the end of the wing 531 away from the root 532 is configured as a free end 536, and the slot 5353 of the branched structure 535 is towards the outflow end 102. The wing 531 further extends from the convergence point of the branched structure 535 towards the free end 536.

Figure 43:
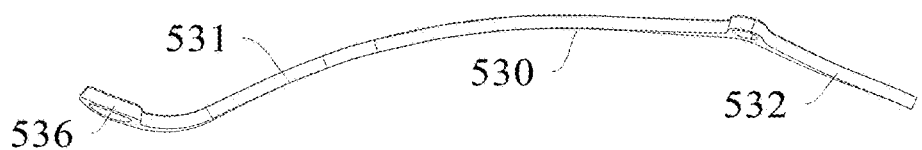
FIG. 43 is a front view of the guiding member in a released configuration (with the root moved outwardly)
Figure 44:
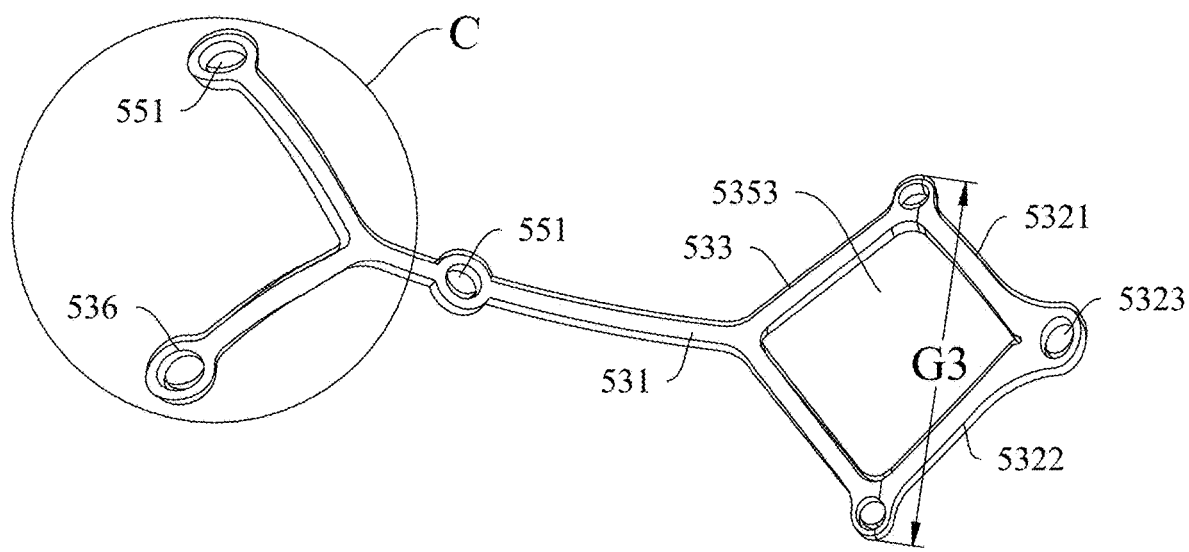
FIG. 44 is a perspective view of the guiding member of FIG. 43.

As shown in FIGS. 41*a*-42*c*, the two opposite parts of the branched structure 535 are constrained by the root 532 to move towards each other in the loaded configuration and in the transition configuration. As shown in FIGS. 43-44, the two opposite parts of the branched structure 535 move away from each other with the deformation of the root 532 and the inner frame 103 in the released configuration. For example, in the loaded, transition, and released configurations, the circumferential spans of the two opposite parts of the branched structure 535 are G1, G2, and G3, respectively, satisfying G1=G2<G3.

The root 532 and the branched structure 535 enclose a triangle, a trapezoid, or a rectangle, or the like. The two opposite parts of the branched structure 535 converge and extend towards the free end 536, and then split circumferentially adjacent the free end 536.

With regard to the shape of the wing 531, an embodiment of the present application further provides a prosthetic heart valve device having an inflow end and an outflow end opposite to each other, including an inner frame 103, leaflets 200 and positioning mechanism. The inner frame 103 and the leaflets 200 can refer to the other embodiments. The difference between the present embodiment and the other embodiments is that the present embodiment does not strictly limit the transition configuration of the positioning mechanism. For example and specifically, the prosthetic heart valve device includes:

the inner frame 103, which has a radially deformable meshed cylindrical structure and has relative compressed and expanded configurations, and the interior of the inner frame 103 is configured as a blood flow passage axially passing therethrough;

leaflets 200, connected to the inner frame 103, wherein the leaflets 200 cooperate with each other to control opening and closing of the blood flow passage; and a positioning mechanism arranged in the circumferential direction of the inner frame, the positioning mechanism including a root 532 connected to the inner frame 103 and a wing 531 extending from the root 532 towards the inflow end; the wing is extendable in the peripheral region of the inner frame, with a receiving space defined between the wing and the outer wall of the inner frame for allowing the entry of the native leaflet; the inner frame 103 has commissure regions each of which corresponds to the coaptation portion of adjacent leaflets, and the root 532 is located between two adjacent commissure regions in the circumferential direction; the end of the wing 531 away from the root is a free end, and the portions of the wings 531 adjacent to the free ends extend along the circumferential direction of the inner frame in a radiation pattern. Of course, the positioning mechanism of the prosthetic heart valve device of the present embodiment can also have the guiding members with various configurations as described above.

Figure 45:
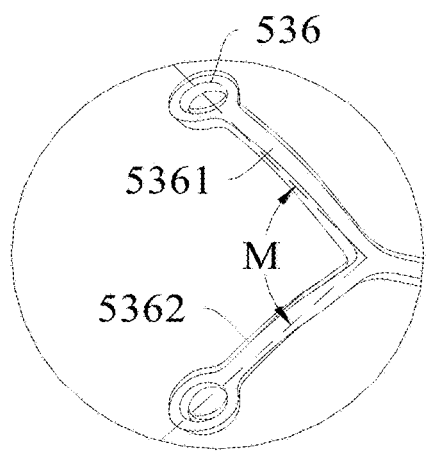
FIG. 45 is an enlarged view of part C of FIG. 43b.

The radiation distribution can reduce the safety risk and also ensure the positioning effect. The wing 531 is divided into at least two parts at the portion adjacent to the free end 536, i.e., the seventh bar 5361 and the eighth bar 5362, respectively, and the angle M between the connecting lines of the respective ends of the two bars is about 45 degrees or more, for example, 45 to 120 degrees as shown in FIG. 45. In the axial direction of the inner frame 103, the free end 536 is located adjacent to the inflow end 101 of the inner frame 103, and the root 532 is located adjacent to the outflow end 102 of the inner frame 103, so that the wing 531 has a sufficient extension to ensure positioning. In order to improve safety, the free end 536 has a rounded structure. For example, the seventh bar 5361 and the eighth bar 5362 can have rounded structure at the ends thereof. The free end 536 can be further surrounded with a protective layer. Alternatively, the free end 536 can be ring-shaped, and can be further covered with protective layer or can be suffered from a surface smoothness treatment.

Figure 46:
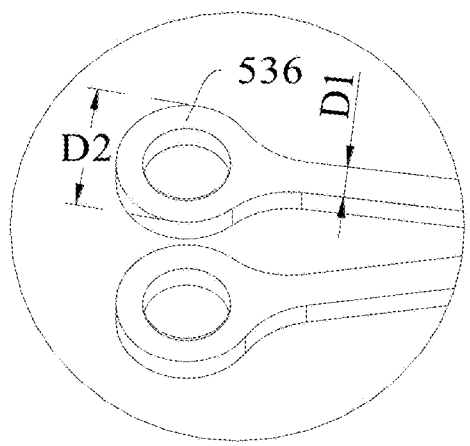
FIG. 46 is an enlarged view of part B of FIG. 41b.

As shown in FIG. 46, the wing 531 has opposite length and width directions, and the width of the ring-shaped free end is larger than the width of the wing bar. The width DH2 of the ring-shaped free end is 2 to 6 times the width D1 of the wing bar.

As shown in FIG. 47, in order to better position the inner frame 103 and reduce the offset after positioning, the guiding members 530 need to have a sufficient circumferential span. The circumferential span of the single guiding member 530 has a center angle Σ of 30 to 60 degrees, and the circumferential span β of the root 532 of the single guiding member with respect to the inner frame 103 is 15 to 45 degrees.

The wing 531 expands radially outward and then bends inward during the extension to the inflow end, providing greater clipping force and allowing greater radial deformation.

The root 532 is fixed to the radially inner, or outer side of the inner frame 103 or radially aligned with the inner frame 103 by means of welding, riveting or binding, so that the root 532 is always attached to the inner frame 103 in any configuration, and deforms in the circumferential direction as the inner frame 103 deforms in the circumferential direction in the transition configuration and the released configuration, wherein the deformation amount of the root 532 is the same as the corresponding portion of the inner frame.

Figure 48:
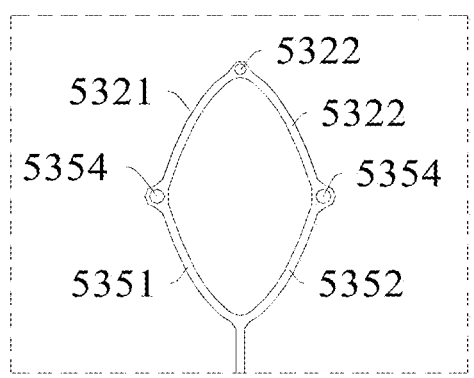
FIG. 48 is a view of connected bars of a root.
Figure 49:
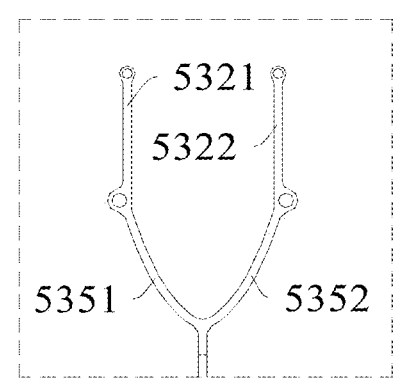
FIG. 49 is a view of parallel bars of a root.
Figure 50:
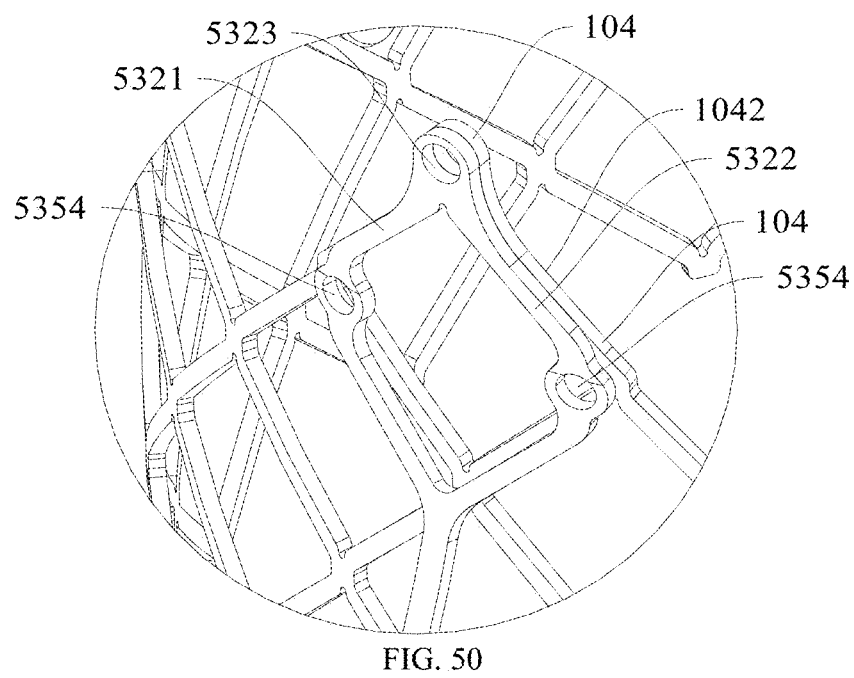
FIG. 50 is an enlarged view of part A of FIG. 33c.

The root 532 can be secured to the outside of the inner frame 103 by binding to facilitate assembly and allow the bars of the root 532 to twist about its own longitudinal axis. The root 532 includes a first bar 5321 and a second bar 5322 connected to the wing 531 (i.e., a branched structure). The root 532 further extends towards the outflow end 102 relative to inner frame 103 to provide sufficient space to allow the inner frame 103 to be lowered further in position, ensuring that the free end of the wing extends into the sinus floor of the valvular sinus. As shown in FIGS. 48 to 50, the ends of the first bar 5321 and the second bar 5322 away from the wing 531 are connected with, parallel to or away from each other.

For example, the ends of the first bar 5321 and the second bar 5322 away from the wing 531 are connected with each other, and are fixed to the inner frame 103 through a binding line (not shown) passing through the first binding eyelet 5323. Similarly, the corresponding portion of the inner frame can also be provided with a similar eyelet as required.

The other ends of the first bar 5321 and the second bar 5322 are spaced apart from each other and are connected to the wing 531 (i.e., the branched structure) to form a closed quadrangle. In order to facilitate the positioning and threading, one end of the first and second bars connecting with the wing 531 is respectively provided with a second binding eyelet 5354. Similarly, the corresponding portion of the inner frame can also be provided with a similar eyelet as required.

In some embodiment, the inner frame 103 has a connecting post 104 extending axially and outwardly towards the outflow end 102. The connecting post 104 can use the same shape as the root 532 and radially overlap on the inner frame. The same shape means that the connecting post 104 also includes fifth bar 1041 and sixth bar 1042 similar to the first bar 5321 and the second bar 5322 (in combination with FIG. 37a). The fifth and sixth bars 1041, 1042 conform to the shape of the root 532, for example, the ends thereof adjacent the outflow end 102 meet each other such that the tip of the connecting post 104 is V-shaped towards the outflow end 102, or parallel, or are parallel to or away from each other. The first bar 5321 and the fifth bar 1041 can be overlap with each other, and the second bar 5322 and the sixth bar 1042 can be overlap with each other.

Figure 37C:
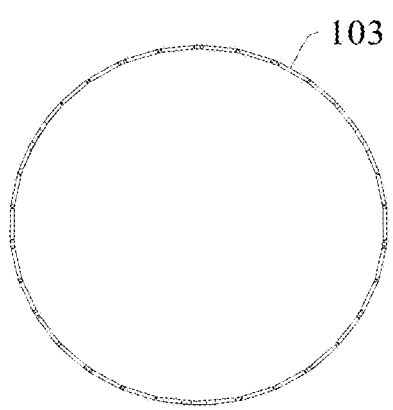
Figure 37D:
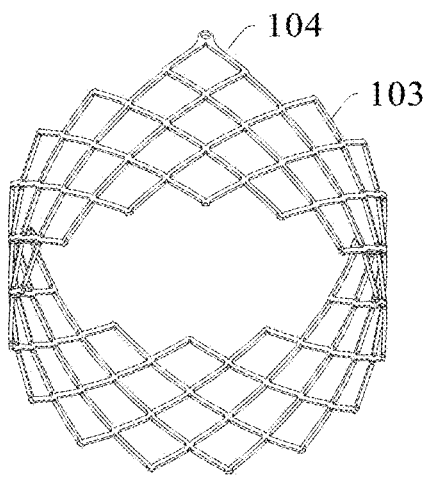

The inner frame 11 has a plurality of diamond shaped cells 116 distributed in the axial direction, the root 532 of the single guiding member 530 corresponds to one or more, for example, two or more cells with respect to the circumferential span of the inner frame 103. As shown in FIG. 37a, the fifth bar 1041 and the sixth bar 1042 extend from the end nodes of the inner frame 103. The cells of the inner frame at the outflow end 102 are cut in half and thus opened, and the ends of the fifth bar 1041 and the sixth bar 1042 are connected with two adjacent cells 116.

The wing 531 includes a third bar 5351 and a fourth bar 5352 adjacent the root and thus forms a branched structure, wherein one end of the third bar 5351 is connected with the first bar 5321, one end of the fourth bar 5352 is connected with the second bar 5322, and the other ends of the third bar 5351 and the fourth bar 5352 extend towards the inflow end 101 and intersects with the third bar 5351.

The first bar 5321, the second bar 5322, the third bar 5351, and the fourth bar 5352 form a closed region, and the radially projected shape of which is quadrangular. For example, the four bars form a parallelogram.

In the case where the ends of the first bar 5321 and the second bar 5322 away from the wing 531 are parallel to or away from each other, the first bar 5321 and the second bar 5322 as well as the wing form a semi-closed area opened towards the outflow end 102.

The above bars are not strictly limited to be straight bars, but can be slightly curved or bent. The fourth bar 5352 and the third bar 5351 can be directly connected with each other or indirectly connected by other bar(s). As shown in the figure, the fourth bar 5352 and the third bar 5351 are directly connected with each other. After the bars are connected with each other, the bar can extend a certain distance and then be branched to the free ends, or be directly branched to the free ends, or can be branched and then meet again to form a ring structure, which can reduce the interference on the coronary orifice and the risk of puncturing the tissue.

The junction between two adjacent bars, for example, between the fourth bar 5352 and the second bar 5322, does not need a sharp turning, but can be shaped smoothly. For example, the third bar 5351 and the fourth bar 5352 can be formed in one piece having an arc structure, wherein the third bar 5351 and the fourth bar 5352 represent different portions of the arc structure. Therefore, it can be conceived that the first to fourth bars above can not only form as a parallelogram, but also can be an enclosed circle, ellipse, or even hexagon or the like.

At least the third bar 5351 is not collinear with the first bar 5321, and the fourth bar 5352 is not collinear with the second bar 5322, otherwise, the expected deformation of the guiding member would be affected or weakened.

In the following, the deformation of the guiding member when it is switched between the transition configuration and the released configuration will be explained, wherein the first bar 5321 and the second bar 5322 define a first portion 538, and the third bar 5351 and the fourth bar 5352 define a second portion 539.

The third bar 5351 and the first bar 5321 meet at a first connection point 5324; the fourth bar 5352 and the second bar 5322 meet at a second connection point 5325; the first bar 5321 and the second bar 5322 meet at a third connection point 5326; and the third bar 5351 and the fourth bar 5352 meet at a fourth connection point 5355, wherein the first connection point 5324, the second connection point 5325, and the third connection point 5326 form a first plane 5327 in which the first portion is located, and the first connection point 5324, the second connection point 5325 and the fourth connection point 5355 form a second plane 5356 in which the second portion is located. It should be noted that the first plan and the second plane are for illustration, and they may be slighted curved or approximate planes.

The structure enclosed by the first to fourth bars above does not need to correspond to the cell of the inner frame. For example, the first connection point 5324 and the second connection point 5325 can be respectively aligned with the nodes of the inner frame, or can be offset from the nodes of the inner frame to reduce the interference with the inner frame during deformation.

Figure 51A:
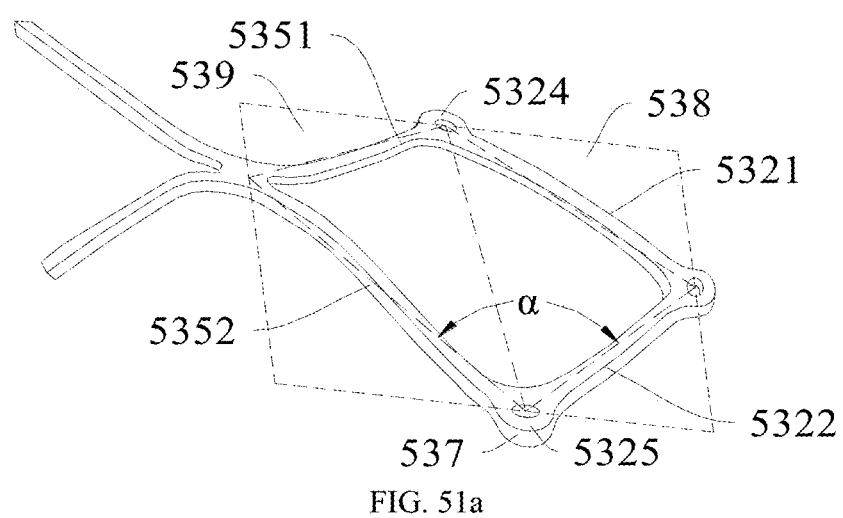
FIG. 51a is a perspective view of a guiding member of a prosthetic aortic valve device in one embodiment before preset.

In FIG. 51*a*, when the bars are fully extended, they lie in the same plane (Q=180 degrees), and the distance between the first connection point 5324 and the second connection point 5325 is at the largest.

Figure 51B:
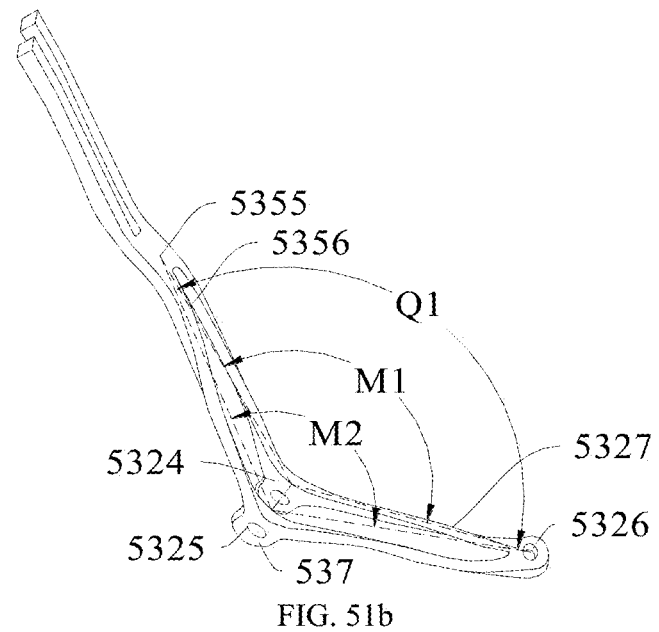
FIG. 51b is a perspective view of the bars of the root of the guiding members of FIG. 51a being close to each other (transition configuration)

In FIG. 51*b*, in the transition configuration, the inner frame 103 is in the compressed configuration, so that the first connection point 5324 and the second connection point 5325 are close to each other, the wing 531 is warped with respect to the root 532, and the first plane 5327 and the second plane 5356 form an angle Q1 therebetween. It should be noted that, when the first connection point 5324 and the second connection point 5325 moves towards each other, each bar may twist about its own axis in order to adapt the warpage of the wing 531, otherwise, the deformation only occurs in a plane, i.e., only the length of the guiding member is stretched, which is in cooperation with the binding of the root to the inner frame 103. It can be seen from the figures that, in different configurations, the first to fourth bars have already twisted, and the first connection point 5324 and the second connection point 5325 are no longer coplanar with the third connection point 5326 and the fourth connection point 5355.

Figure 51C:
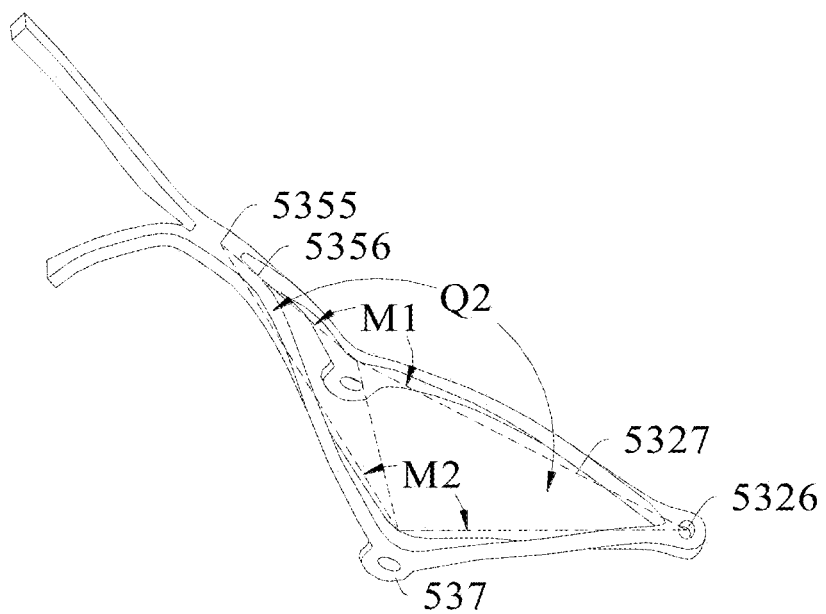
FIG. 51c is a perspective view of the bars of the root of the guiding members of FIG. 51b being away from each other (released configuration)

In FIG. 51*c*, when transforming from the transition configuration to the released configuration, the first connection point 5324 and the second connection point 5325 move away from each other, and the warpage degree of the wing 531 is reduced, in which case, the angle between the first portion 538 and the second portion 539 is Q2, and Q1 is less than Q2, which means that the free end of the wing is closer to the inner frame, facilitating clipping the native leaflets.

It can be seen from the figures that the angle M1 between the axis of the third bar 5351 and the axis of the first bar 5321 and the angle M2 between the second bar 5322 and the fourth bar 5352 are substantially unchanged when switching between the transition configuration and the released configuration. For example, M1=M2=120 degrees. In other words, the guiding member is not deformed in a plane, but in three dimensions.

As described above, it can be seen that the root 532 and the portion of the wing 531 connected with the root 532 constitute a frame structure, for example, including the first to fourth bars. Two ends of the frame structure in the circumferential direction, for example, the first connection point 5324 and the second connection point 5325, are relatively turned over as the inner frame is compressed and expanded, thereby driving the two ends of the frame structure in the axial direction of the inner frame, such as the third connection point 5326 and the fourth connection point 5355, to be relatively turned over.

In the frame structure, when the two ends in the axial direction of the inner frame are turned over relative to each other, one end such as the third connection point 5326 is fixed relative to the inner frame, and the other end such as the fourth connection point 5355 is turned over relative to the outer wall of the inner frame.

During the compression of the inner frame, within the frame structure, two end in the circumferential direction of the inner frame, for example, the first connection point 5324 and the second connection point 5325, have relative movement, and the first connection point 5324 and the second connection point 5325 are close to each other when the inner frame is radially contracted, while the first connection point 5324 and the second connection point 5325 are away from each other when the inner frame is radially expanded.

The first connection point 5324 and the second connection point 5325 are also turned over with respect to the outer peripheral wall of the inner frame when moving away from or close to each other, where the turning directions are opposite to each other with respect to the axis of the inner frame.

In order to facilitate the deformation, during processing the guiding member, the wing 531 can be slightly warped with respect to the root 532 in the shaping configuration after the heat treatment.

The guiding member 530 has restricting structures 537 opened at the first connection point 5324 and the second connection point 5325, and the first connection point 5324 and the second connection point 5325 are bound to the inner frame 103 through the restricting structures 537. The restricting structure 537 can be configured as an eyelet (i.e., the second binding eyelet 5354) or other protrusions extending circumferentially outwardly with an eyelet. The restricting structure 537, as a force point, rotates relative to the axis of the bar, thereby driving the portions of the bars adjacent to the restricting structure to twist.

In order to reduce the restraint on the twist of the bars and obtain a larger turning angle of the wing, when binding, only one side with the eyelet in the axial direction of the inner frame is bound, as the bars may be restrained to twist if two sides in the axial direction of the inner frame are bound.

In cooperation with an imaging equipment, the prosthetic aortic valve device 1000 can be provide with a radiopaque marker 550, which can be embedded or include a precious metal that can be displayed differentiating from other portions under X-ray or other means of detection.

The radiopaque marker 550 can be in the form of a dot or a strip or a ring (closed or non-closed, but at least in half ring), and the radiopaque marker 550 can be disposed on at least one of the inner frame 103 and the guiding members 530. Accordingly, the inner frame 103 or the guiding members 530 are provided with eyelets for receiving the radiopaque marker 550.

Optionally, each of the above binding eyelets can be provided with a radiopaque marker, or the radiopaque marker can be provided at the middle portion or the free end of the wing.

Figure 52:
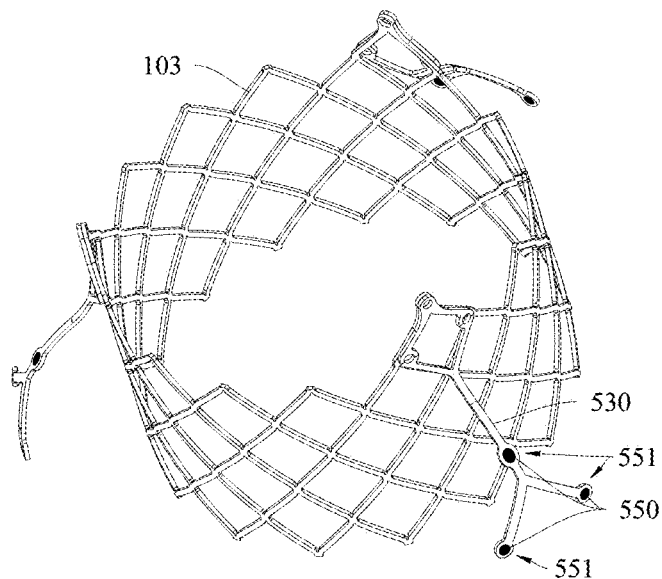
FIG. 52 is a perspective view showing the distribution of radiopaque markers in a prosthetic aortic valve device.

For example, as shown in FIG. 52, the free end 536 carries radiopaque markers 550. The free end 536 has eyelets 551 at which the radiopaque markers are located. As another example, the wing 531 is provided with an eyelet 551 at a position before being branched and can be provided with a radiopaque marker at the eyelet 551.

Figure 53:
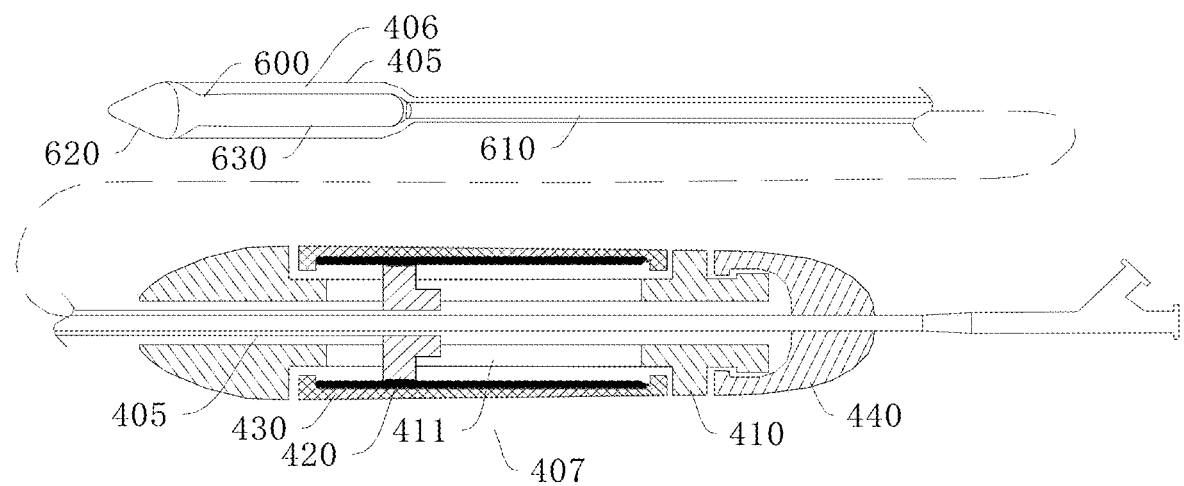
FIG. 53 is a view of a delivery system according to an embodiment of the present application.
Figure 54:
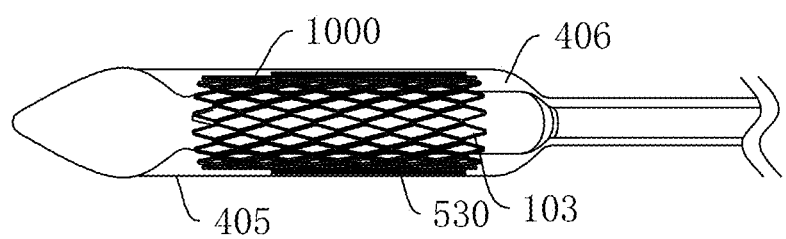
FIG. 54 is a view of the distal section of the delivery system of FIG. 53 loaded with a prosthetic aortic valve device.

Referring to FIGS. 53 and 54, in one embodiment, a delivery system for a prosthetic aortic valve device 1000 is provided that can be used to load and deliver the prosthetic aortic valve devices 1000 of the above embodiments. The delivery system has opposite distal and proximal ends, the delivery system including:

- a balloon device 600 switchable between an inflated configuration and a deflated state under the action of a fluid;
- an outer sheath 405 which is slidably fitted on the outer periphery of the balloon device 600, and a radial gap between the outer sheath 405 and the balloon device 600 is a loading zone 406 for placing the prosthetic aortic valve device 1000; and
- a control handle 407, wherein both the proximal ends of the balloon device 600 and the outer sheath 405 extend to the control handle 407 with the outer sheath 405 slidably fit with the control handle 407.

The outer sheath 405 can be moved to cover or expose the prosthetic aortic valve device 1000 to effect switching between the loading and delivery configuration and release configuration. In the delivery system, the outer sheath 405 and the balloon device 600 are rotatably fitted with each, that is, the circumferential position of the prosthetic aortic valve device 1000 can be adjusted by rotating the balloon device 600 so that the valve leaflets 200 can be aligned with the valvular sinuses. In addition, the prosthetic aortic valve device 1000 of the present embodiment is provide with guiding members 530, a radiopaque marker(s) 550 is provided on one of the inner frame 103 and the guiding members 530, so that the prosthetic aortic valve device 1000 can be monitored in real time by mean of an imaging equipment when the position thereof is adjusted, so as to guide the surgery. In this embodiment, the arrangement of the guiding member 530 and the radiopaque marker 550 in cooperation with the rotation of the outer sheath 405 and the balloon device 600 ensures accurate positioning of the prosthetic aortic valve device 1000.

In some case, for example, where the balloon device 600 cannot be rotated relative to the outer sheath 405, although the balloon device 600 and the outer sheath 405 can be rotated together for circumferential alignment, the outer sheath 405 will twist itself due to a relatively long intervention length, and it is difficult for the outer sheath 405 to recover to its untwist configuration around its own axis, so that a large force would inevitably occur between the outer sheath 405 and the surrounding tissues. However, in this embodiment, the outer sheath 405 is used for provide a stable passage, the rotatable balloon device 600 (the tube inside the outer sheath 405) can be twisted around its own axis in the passage so as to reduce the risk to the maximum extent.

When the balloon device 600 is rotated, the outer sheath 405 can be kept at least from being excessively twisted in the circumferential direction, and can be reinforced as needed, for example, by means of an inner rib, a reinforcing mesh, a hypotube, or the like.

The prosthetic aortic valve device 1000 as a whole is radially compressed and placed in the loading zone 406 and surrounded within the distal section of the outer sheath 405. In the release process, the guiding members 530 are progressively exposed by sliding the outer sheath 405 proximally. At this time, although the inner frame 103 is exposed, the inner frame 103 cannot automatically transform into the expanded configuration due to its material thereof, and the circumferential position of the inner frame 103 can be aligned by rotating the balloon device 600. After alignment, the inner frame 103 is driven to expand using the balloon device 600. During the alignment, the outer sheath 405 can be kept relatively stationary, reducing safety hazards and improving the alignment.

Referring to FIG. 53 and FIGS. 54 to 57, the balloon device 600 includes:

- a tube 610 having at least a guidewire channel and an injection channel provided therein, the proximal end of the tube 610 being rotatably mounted to the control handle 407;
- a guiding head 620 which is fixed to the distal end of the tube 610, the distal end of the guidewire channel is opened into the guiding head 620, and wherein during the delivery of the delivery system in vivo, the guide wire can be first intervened into the human body, and then the entire delivery system can be surrounded around the guide wire through the guidewire channel and is advanced along the guide wire; and
- a balloon 630 fixed to the tube 610 at the proximal side of the guiding head 620, the interior of the balloon 630 communicating with the injection channel.

The guidewire channel and the injection channel can be provided with additional tubes, or by a multi-lumen tube, and the guidewire channel and the injection channel can be respectively provided with a tube connector (for example, a three-way structure on the right side shown in FIG. 53, such as a luer connector or the like) at the proximal ends thereof. In practice, the injection channel can be used to deliver fluid to inflate the balloon 630.

In order to allow rotation of that balloon device 600, the tube 610 should be capable of ensuring circumferential torque transmission and minimizing angular deviation between the distal and proximal end. For example, the tube 610 can include a multi-layer structure from the inside to the outside, and at least one layer in the middle is provided with embedded ribs, reinforcing mesh, hypotubes, steel cables and the like to ensure the synchronization of the proximal and distal ends. Of course, when there is a deviation, correction and real-time adjustment can be further carried out by means of the radiopaque marker.

Figure 55:
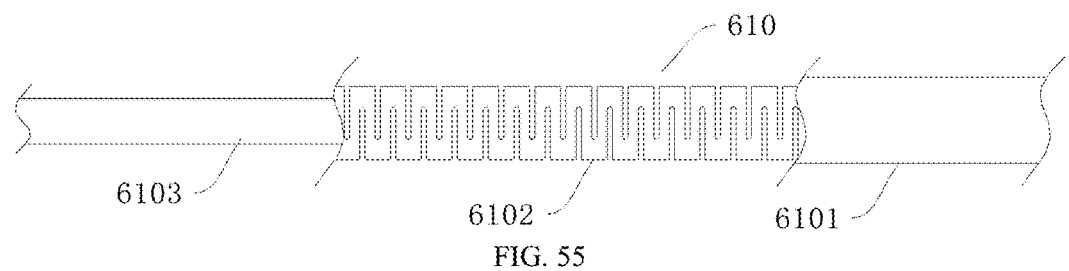
FIG. 55 is a view of the tube of the prosthetic aortic valve device.

For example, as shown in FIG. 55, in one embodiment, the tube 610 has a three-layer structure, the middle layer 6102 is a hypotube and is between the outermost layer 6101 and the innermost layer 6103, and the outermost layer 6101 and the innermost layer 6103 can be made of conventional materials such as Pebax and TUP, which are respectively fixed to the hypotube by means of thermal fusion or the like. The cutting method of the hypotube is not strictly limited, for example, alternate slits at different circumferential positions can be provided to provide the compliance for passing through a curved intervention path.

Figure 56:
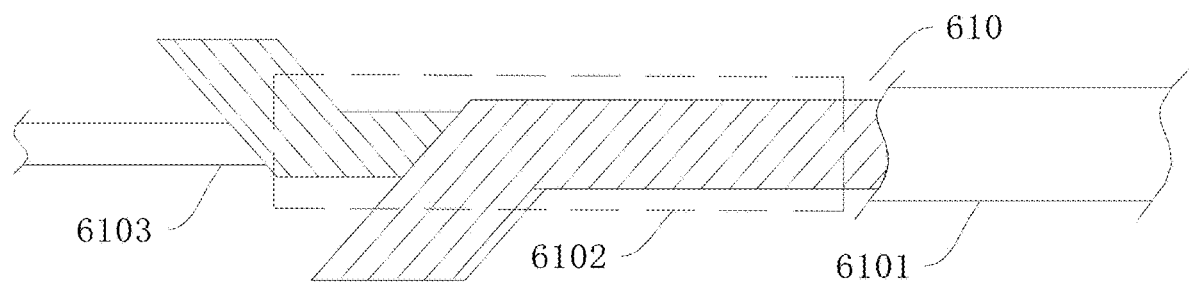
FIG. 56 is a view of another tube of the prosthetic aortic valve device.

For example, as shown in FIG. 56, in another embodiment, the middle layer 6102 is made of two layers of steel cable tubes coiled in opposite directions, which have compliance and can ensure the transmission of torque in the circumferential direction.

The control handle 407 includes:
a support 410;
a movable base 420 movably mounted on the support 410, to which the proximal end of the outer sheath 405 is fixed;
a driving sleeve 430 rotatably mounted on the outer periphery of the support 410 and engaged with the movable base 420 to drive the outer sheath 405 to slide relative to the balloon device 600; and
a rotatable seat 440 rotatably mounted on the outer periphery of the support 410 and engaged with the tube 610 of the balloon device 600 to drive the balloon device 600 to rotate relative to the outer sheath 405.

The driving sleeve 430 and the movable base 420 are threadably engaged with each other. The rotation of the driving sleeve 430 can drive the movable base 420 to slide. In order to prevent free rotation of the movable base 420, the support 410 is provided with a guiding structure, such as a sliding groove 411 or a guiding rod, for restricting the movement of the movable 420. The outer periphery of the support 410 can be fixedly covered with a shell, so as to play a protective and aesthetic role.

The rotatable seat 440 can be directly fixed to the tube 610 of the balloon device 600 as shown in FIG. 53. In operation, the rotatable seat 440 is directly operated, and a marker can be arranged on the rotatable seat 440 and the support 410 to show the direction and magnitude of rotation of the rotatable seat 440.

The rotatable seat 440 and the balloon device 600 can be indirectly connected by a transmission mechanism. A speed reduction mechanism can be used to improve the accuracy of adjustment and improve the feel.

Figure 57:
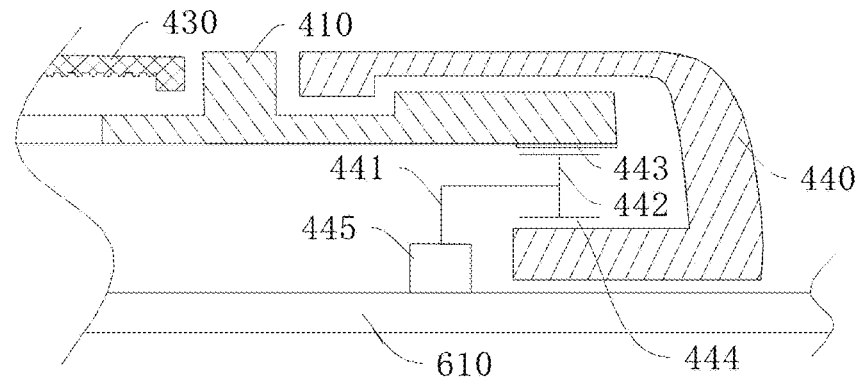
FIG. 57 is a partial view of another form of control handle in the delivery system.

Referring to FIG. 57, this embodiment employs a planetary reduction mechanism, specifically including a planetary carrier 441, planetary gears 442, a ring gear 443, a planetary input shaft 444, and a planetary output shaft 445. The planetary input shaft 444 has external teeth and is fixed to the rotatable seat 440 and configured to be driven by the rotatable seat 440. The planetary input shaft 444 and the rotatable seat 440 can be formed in one or separate pieces.

The ring gear 443 has internal teeth and is fixed to the support 410. The ring gear 443 and the support 410 can be formed in one or separate pieces. The planetary gears 442 generally include three planetary gears 442, meshing between the planetary input shaft 444 and the ring gear 443 and configured for driving the planetary carrier 441. The planetary carrier 441 is fixed to the planetary output shaft 445. When the planetary gears 442 revolve, the planetary carrier 441 rotates, and then the planetary output shaft 445 drives the fixed tube 610 to rotate, thereby driving the balloon device 600 to rotate the inner frame.

Figure 58:
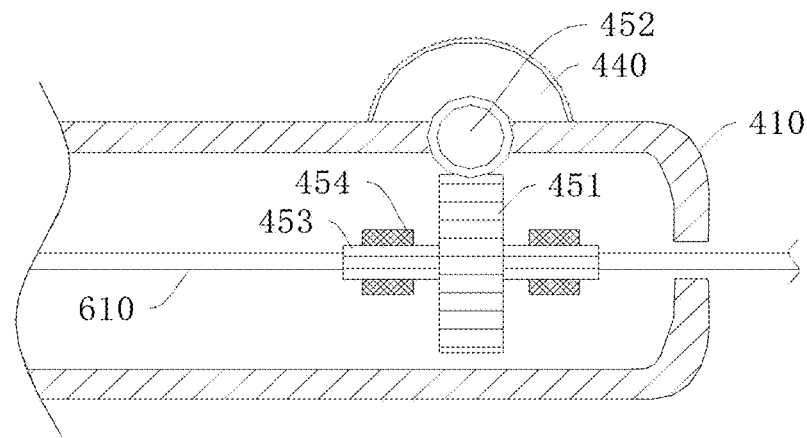
FIG. 58 is a partial view of another form of control handle in the delivery system.

Referring to FIG. 58, in another embodiment, the rotatable seat 440 and the tube 610 are driven by a worm wheel 451 and a worm 452 engaging with each other. The rotatable seat 440 is configured as a wheel and rotatably mounted on the support 410, and the rotating axis of the rotatable seat 440 is perpendicular to the longitudinal direction of the support 410 (i.e., the extension direction of the tube 610). The rotatable seat 440 is coaxially fixed to the worm 452, and the worm wheel 451 is fixed to the tube 610 and engaged with the worm 452. A transmission sleeve 453 for reinforcing the tube 610 can be fixed to the outside of the tube 610, which is rotatably engaged with a support base 454 fixed on the support 410. The transmission sleeve 453 and the worm wheel 451 can be formed in one or separate pieces for transmission. When the rotatable seat 440 rotates, the torque is transmitted to the tube 610 through the worm gear mechanism for rotation.

Figure 59:
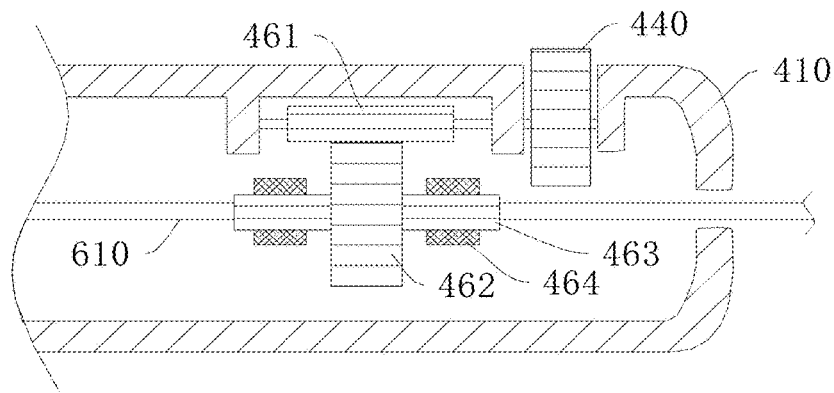
FIG. 59 is a partial view of another form of control handle in the delivery system.

Referring to FIG. 59, in another embodiment, the rotatable seat 440 and the tube 610 can be driven through a gear set. The gear set includes a first gear 461 and a second gear 462 that mesh with each other. For example, the rotatable seat 440 can be a wheel rotatably mounted on the support 410, and the rotating axis of the rotatable seat 440 is parallel to the extension direction of the tube 610. The rotatable seat 440 is coaxially fixed with the first gear 461 for transmission, and a transmission sleeve 463 is fixed to the outside of the tube 610 to reinforce its structure, and the transmission sleeve 463 is rotatably engaged with the support base 464 fixed on the support 410. The transmission sleeve 463 is coaxially fixed with the second gear 462 for transmission.

In the above embodiments that the tube 610 is driven by the rotatable base 440, a locking mechanism for limit the rotation of the rotatable seat 440 can be provided as required, for example, a pin slidably mounted on the support 410. The rotatable seat 440 is provided with an engagement slot or an insertion hole engaged with the pin to realize the position locking of the rotatable seat 440. In addition, a scale mark indicating a rotation angle can be provided on the rotatable base 440 to adjust the rotation angle of the tube 610.

For alignment with the valvular sinuses in vivo and circumferential adjustment of the interventional device, an embodiment of the present application further provides an interventional system including a prosthetic heart valve device and a delivery system. For example, the prosthetic heart valve device can be the prosthetic aortic valve device 1000, and specifically includes an inner frame and a positioning mechanism and leaflets respectively connected to the inner frame.

The delivery system includes a balloon device, an outer sheath slidably fitted around the periphery of the balloon device, a control handle connected to the balloon device and the outer sheath. The prosthetic heart valve can be loaded in the radial gap between the balloon device and the outer sheath. The control handle is provided with a rotatable seat for controlling the rotation of the balloon device such that the positioning mechanism is aligned with the valvular sinuses.

Both the prosthetic heart valve and the delivery system can employ the above embodiments, wherein the prosthetic aortic valve device 1000 is disposed within the loading zone 406 of the delivery system.

Referring to FIGS. 60a-62, an embodiment of the present application provides a method for using the above interventional system, which is also a method for securing the prosthetic heart valve device at an aortic annulus including a plurality of native valve leaflets, which can be implemented using the interventional system described above.

The delivery system enters the human body via the femoral artery. The balloon device 600 and outer sheath 405 should be configured with sufficient length, for example, at least 80 or more, to adapt to the long interventional path. The prosthetic aortic valve device 1000 is typically positioned against the blood flow after passing through the aortic arch, so that the inflow end for the inner frame is the opposite distal end (away from the operator along the interventional path), and the outflow end is the opposite proximal end. According to the normal release method over the path, the inflow end of the inner frame is the end to be released first, and the outflow end is the end to be released later.

The method includes the following steps.

Figure 60A:
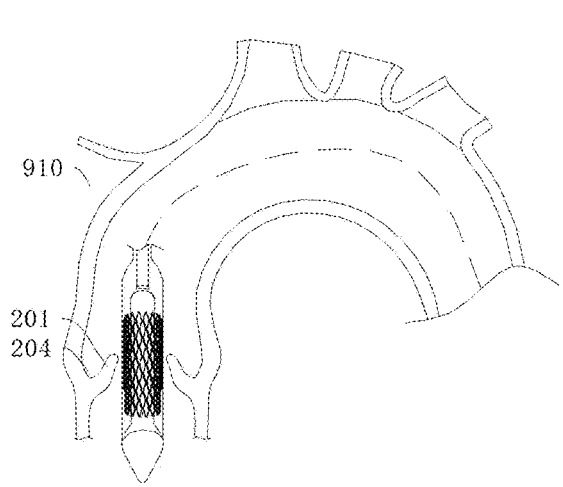

In step S10, as shown in FIG. 60a, the prosthetic aortic valve device 1000 is delivered to a predetermined site, wherein the inner frame 103 is in a compressed configuration, the guiding members 530 are in a loaded configuration, and the balloon device 600 is in a deflated configuration. In the delivery process, an imaging equipment can be used to detect and display the radiopaque markers, and the spatial position of the prosthetic aortic valve device 1000 relative to the aortic valve can be determined by means of the contrast medium.

In step S20, as shown in FIG. 60b, after the prosthetic aortic valve device 1000 enters the native annulus (aortic annulus), the outer sheath 405 is retracted proximally to expose the wings 531 of the guiding members 530, which is also related to the manner in which the delivery system of this embodiment enters the human body via the femoral artery, so that the guiding members 530 made of the memory material tends to the preset configuration in the in vivo environment, with the wings expanding outward into the transition configuration, while the inner frame made of non-memory material is still in the compressed configuration, so that the roots of the guiding members do not obviously extend outward.

In step S30, the positions of the guiding members 530 in vivo, especially relative to the native annulus and valvular sinuses 204 can be obtained by using the imaging equipment in combination with the radiopaque marker. Now, whether the circumferential positions of the guiding members 530 are aligned with the respective valvular sinuses can be initially determined. In some cases, for example, if the guiding members 530 are exactly aligned with the respective valvular sinuses, the prosthetic aortic valve device 1000 can be pushed further distally so that the free ends of the wings of the guiding members 530 generally abut the sinus floors of the valvular sinuses. If misaligned, the balloon device is rotated and the inner frame 103 is moved synchronously so that the wings 531 of the guiding members 530 are approximately aligned in the circumferential direction and then enter the valvular sinuses 204, and then the prosthetic aortic valve device 1000 is pushed distally, so that the free ends of the wings of the guiding members 530 further abut against the sinus floors of the valvular sinuses.

Since the guiding members are in the transition configuration, the wings thereof extend outward relative to the inner frame, so that at least one native valve leaflet enters the radial gap between the inner frame and the guiding member. At this time, it can be considered that the axial position of the prosthetic aortic valve device is desired. Preferably, all three native leaflets enter the respective radial gaps.

Otherwise, the whole device needs to be withdrawn proximally to readjust the position for ensuring clipping the native valve leaflets and the stability of the axial position after release.

In step S40, as shown in FIG. 61a, the balloon device 600 is driven to the inflated configuration by injecting fluid, that is, the inner frame 103 and the roots 532 of the guiding members 530 are released, so that the inner frame 103 transforms into the expanded configuration, and the guiding members 530 transform into the released configuration. Now, the prosthetic aortic valve device 1000 is released into position.

In the process of inflation and deformation of the balloon device, the two ends of the balloon in the axial direction suffer from relatively small radial restraint force, and thus will be first deformed, especially at the outflow end of the inner frame, which can drive the end of the inner frame together with the roots to move outwardly, so that the free ends of the wings tend to move closer to the inner frame to clip the native leaflets.

After the inner frame 103 transforms into the expanded configuration, the outflow section of the inner frame 103 can be substantially in a straight cylindrical configuration or flared, depending on the pressure of the balloon or the shape of the balloon, and the roots radially move away from each other. Referring to the above deformation mechanism of the guiding members 530, the roots and the junctions with the wings deform so that the free ends of the wings of the guiding member 530 will further move closer to the outer wall of the inner frame 103 relative to the transition configuration to clip the native leaflets to ensure the positioning effect.

Figure 61B:
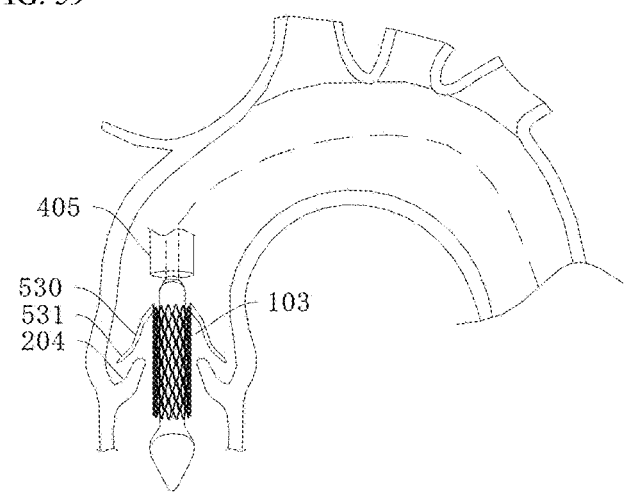

In step S50, as shown in FIG. 61b, after release, the balloon device 600 is switched to the deflated configuration, and the entire delivery system is retracted, while the prosthetic heart valve device is positioned and remained at the aortic annulus to replace the diseased native tissue.

In the present application, the prosthetic aortic valve device 1000 is improved in structure to facilitate circumferential position adjustment, aligning the valve leaflets 200 with the coronary orifice to reduce blood flow interference, and further avoiding positional deviation during long-term use.

Another embodiment of a prosthetic heart valve device according to the present application has opposite inflow and outflow ends, including an inner frame 103, leaflets 200 and a positioning mechanism, wherein the inner frame 103 and leaflets 200 can refer to the other embodiments. The difference between this embodiment and the other embodiments is that the present embodiment does not strictly limit the transition configuration of the positioning mechanism. For example, the prosthetic heart valve device specifically includes:

the inner frame 103, which has a radially deformable meshed cylindrical structure and has relative compressed and expanded configurations, and the interior of the inner frame 103 is configured as a blood flow passage axially passing therethrough;

leaflets 200, connected to the inner frame 103, wherein the leaflets 200 cooperate with each other to control opening and closing of the blood flow passage; and a positioning mechanism arranged in the circumferential direction of the inner frame, the positioning mechanism including a root 532 connected to the inner frame 103 and a wing 531 extending from the root 532 towards the inflow end; the wing 531 is extendable in the peripheral region of the inner frame, with a receiving space defined between the wing and the outer wall of the inner frame for allowing the entry of the native leaflet; and the positioning mechanism corresponding to the same leaflet in the circumferential direction of the inner frame is formed by separate positioning members.

Figure 1C:
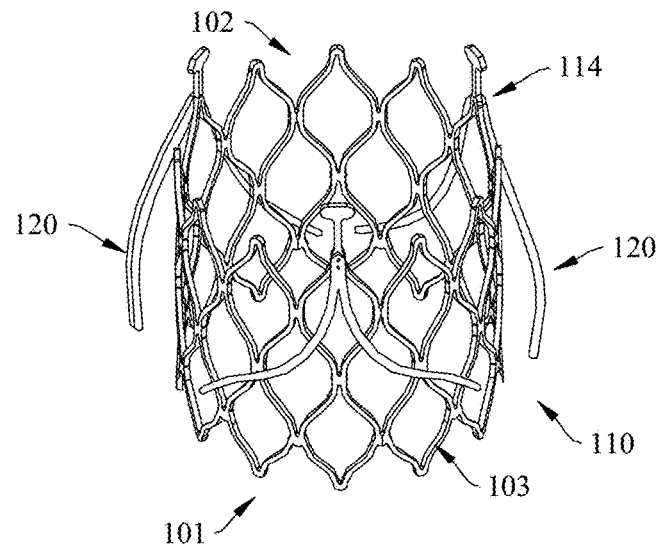
FIG. 1c is a perspective view of a frame for a prosthetic heart valve device according to an embodiment.

The positioning mechanism formed by separate positioning members can refer to FIG. 1c. That is, the positioning mechanism corresponding to the same leaflet in the circumferential direction of the inner frame are two clipping arms, and one end of each clipping arm connected to the inner frame is a fixed end, the other end is the opposite free end, and the free ends of the two clipping arms are spaced apart from each other and tend to close to each other.

Figure 63:
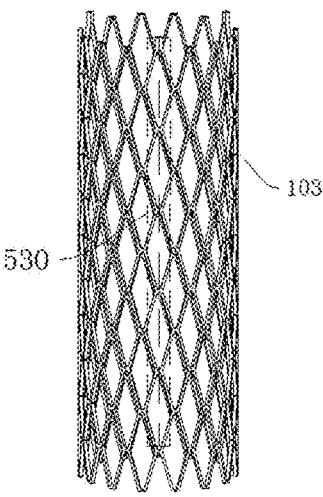
FIG. 63 is a view of the prosthetic aortic valve device in a loaded configuration (leaflets are not shown).
Figure 64:
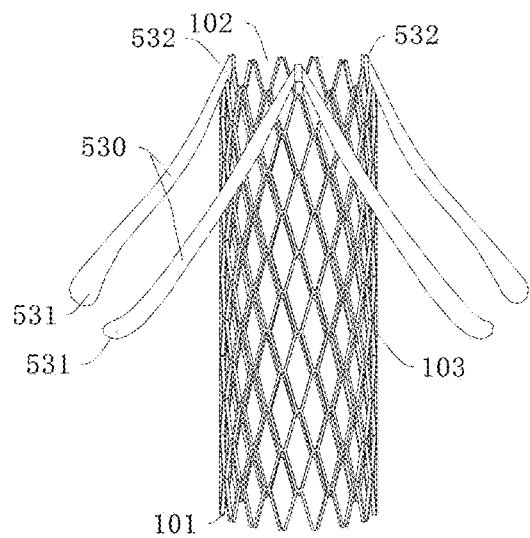
FIG. 64 is a view of the prosthetic aortic valve device of FIG. 63 in a transition configuration.
Figure 65:
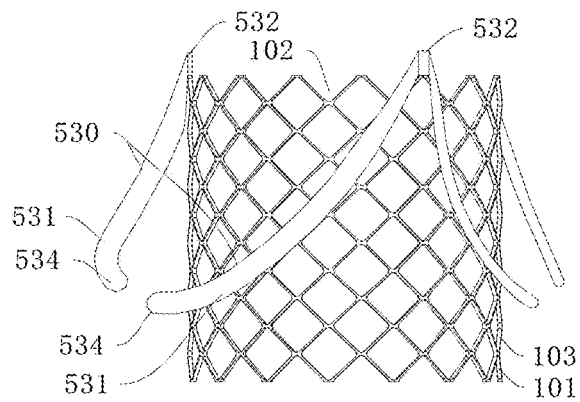
FIG. 65 is a view of the prosthetic aortic valve device of FIG. 64 in a released configuration.

The positioning mechanism formed by separate positioning members can also refer to FIGS. 63 to 65. That is, the positioning mechanism corresponding to the same leaflet in the circumferential direction of the inner frame includes guiding members, and the guiding member has two wings. The wing has a free end away from the root, and the free ends of the two wings of the guiding member are spaced apart from each other. Of course, the positioning mechanism, that is, the guiding members in this embodiment can further have:

In the loaded configuration, the guiding members 530 (shown in dashed lines) are radially pressed against the inner frame 103 in the compressed configuration, so that the inner frame 103 and the guiding members can be easily surrounded by the sheath and delivered in vivo.

In the transition configuration, the roots 532 of the guiding members 530 remain gathered to adapt the compressed configuration of the inner frame 103. The wings 531 are self-deformed and thus extend outside of the inner frame 103, with a receiving space formed between the outer wall of the inner frame 103 and the wings 531 for receiving the native leaflets 201. In order to circumferentially position the inner frame 103, the extended wings 531 can be adjusted in position to enter the corresponding valvular sinuses, with the inner frame 103 inside the native leaflets and the wings 531 outside the native leaflets.

In the released configuration, the roots 532 of the guiding members 530 move away to adapt the expanded configuration of the inner frame 103, at which time both the inner frame 103 and the guiding members 530 are fully released from the delivery system into the work state.

FIGS. 63-65 are only for illustration of the spatial posture and relative relationship or characteristics in different configurations. Unless otherwise specified, the shape and position of the guiding member 530 are described referring to the released configuration, and the shape and position of the inner frame 103 are described referring to its expanded configuration.

The meshed cylindrical structure can be radially deformed to facilitate the intervention after compression and the subsequent expansion and release. The axial length of the meshed cylindrical structure may change when the meshed cylindrical structure is radially deformed. The meshed cylindrical structure is configured to be expanded by external force, i.e., the meshed cylindrical structure is not made of self-expandable material. In general, the meshed cylindrical structure can be expanded by balloon. However, the guiding member 530 is made of a memory material (e.g., pre-heat-set nickel-titanium alloy), which can be released in the human body first, the root 532 of which can be considered as a portion where the guiding member 530 and the inner frame 103 are adjacent and connected to each other. The specific shape is not strictly limited. The root 532 and the wing 531 can be formed in one piece to facilitate processing.

The wing 531 extends outward relative to the inner frame 103 after release, and by adjusting the posture of the inner frame 103, the wing 531 can enter into the valvular sinus 204 to pre-position the inner frame 103 in the circumferential direction, and then the inner frame 103 can be released and expanded by balloon. Because the guiding members 530 are aligned with the valve leaflets 200, the junction of adjacent valve leaflets 200 avoids the coronary artery orifice and prevents the blood flow from being obstructed. In addition, the wings 531 abut against the sinus floors of the valvular sinuses 204, which positions the inner frame 103 in the axial direction to avoid slipping to the left ventricle side under the action of the reverse flow of blood.

Figure 66A:
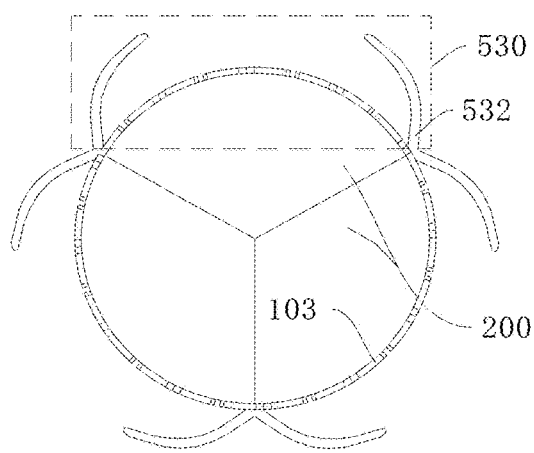
FIG. 66a is a view of a prosthetic aortic valve device according to an embodiment.
Figure 66B:
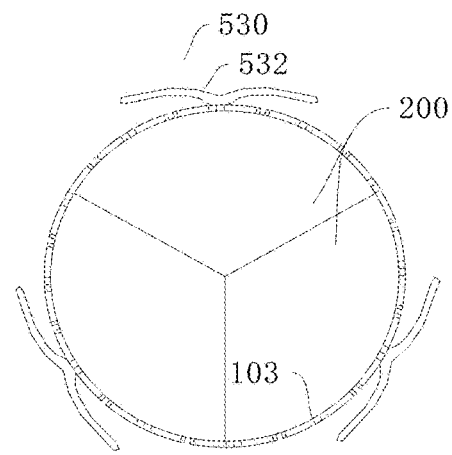
FIGS. 66b-66c are views of a prosthetic aortic valve device according to an embodiment.
Figure 66C:
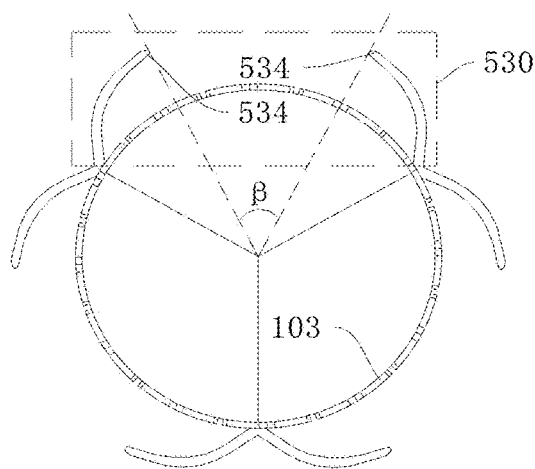
Figure 66D:
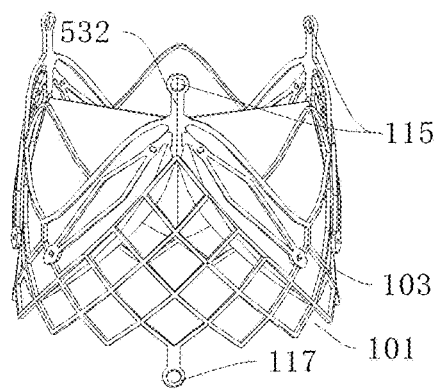
FIG. 66d is a perspective view of a prosthetic aortic valve device according to an embodiment.

In order to fix the guiding member 530, as shown in FIGS. 66a and 66d, the junction of two adjacent leaflets 200 on the inner frame 103 is the commissure region of the inner frame 103, and the root 532 of the guiding member 530 is fixed to a corresponding junction. Alternatively, the root 532 of the guiding member 530 can be located between two adjacent junctions in the circumferential direction of the inner frame 103.

Referring to FIG. 66d, in the released configuration, the free ends 534 of the two wings 531 of the individual guiding member 530 are spaced apart from each other, and the spacing region has a central angle β, in the circumferential direction of the inner frame 103, greater than 30 degrees.

The commissure region can be a strip-shaped, i.e., commissure post 132, and each commissure post 132 can be provided as follows.

The commissure post 132 can extend from the end node of the outflow end 102 of the inner frame 103 or be located within the inner frame 103. The commissure post 132 extends along the axis of the inner frame 103 or is inclined radially inward. For example, the outflow end 102 of the inner frame 103 can have a structure with peaks and valleys, and the commissure region is located at the peak, that is, at the most-distal end of the outflow end of the inner frame 103.

Referring to FIGS. 66a to 66d, the end of the commissure post 132 is provided with a first collar 115, and the inner frame 103 is provided at the inflow end 101 with a second collar 117 in alignment with the first collar 115. The first collar 115 and the second collar 117 can be used for providing radiopaque marker or can be used to connect with the delivery system as required.

Figure 67:
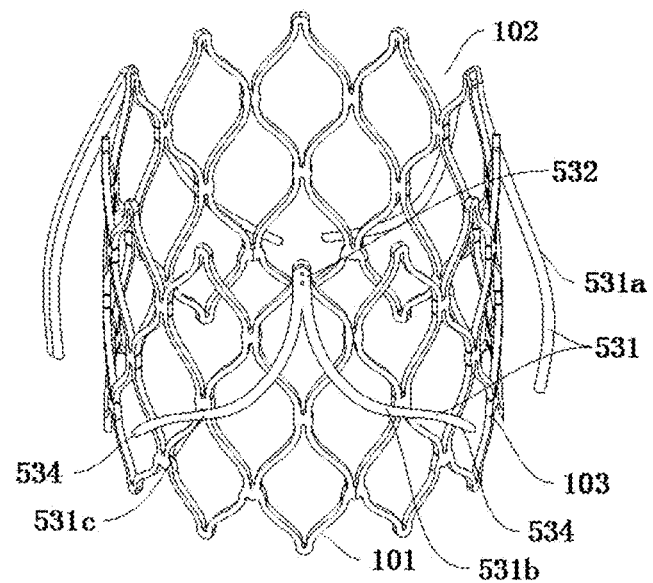
FIG. 67 is a perspective view of a prosthetic aortic valve device according to another embodiment.

Referring to FIG. 67, each guiding member 530 can include two wings 531a and 531b, the ends of which facing away from the inner frame 103 are separate free ends 534. In one guiding member, failure of one of the free ends 534 to enter the valvular sinus does not necessarily affect the other free end, thus avoiding to some extent the risk of failure of the guiding member as a whole.

In the axial direction of the inner frame 103, the free end 534 is located adjacent to the inflow end 101 of the inner frame 103, and the root 532 is located adjacent to the outflow end 102 of the inner frame 103, so that the wing 531 has a sufficient extension to ensure positioning. In order to improve safety, the free end 536 has a rounded structure, and can be further covered with a protective layer.

Taking FIG. 67 as an example, in two adjacent guiding members, the wing 531b and the wing 531c, which are close to each other, are formed in one piece by a common root 532, and the common root 532, the wing 531b and the wing 531c form a branched structure, the opening of which faces towards the inflow end 101. This branched structure facilitates crossing the junction of the two native leaflets by virtue of its opening such that the guiding members can be respectively positioned in the respective sinuses.

Figure 68A:
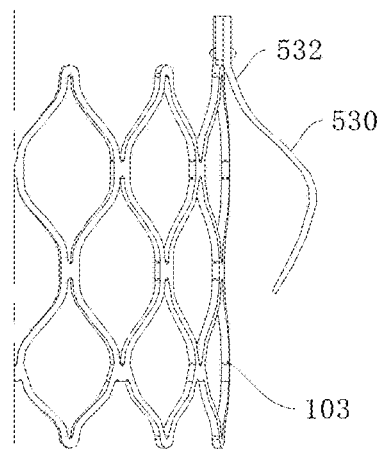
FIGS. 68a to 68c show different configurations of the guiding member of the prosthetic aortic valve device.
Figure 68B:
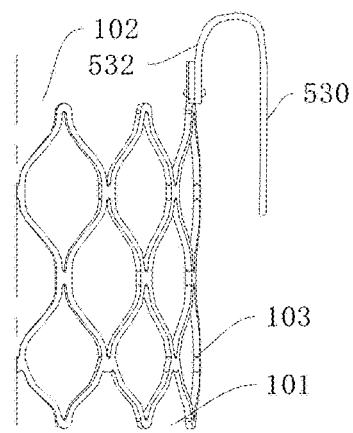
Figure 68C:
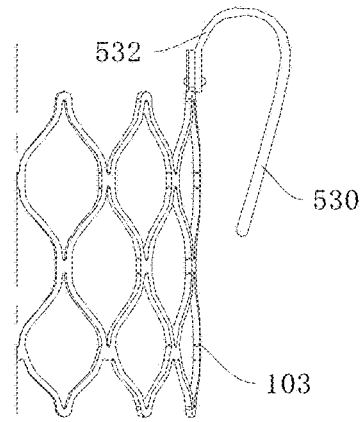
Figure 72A:
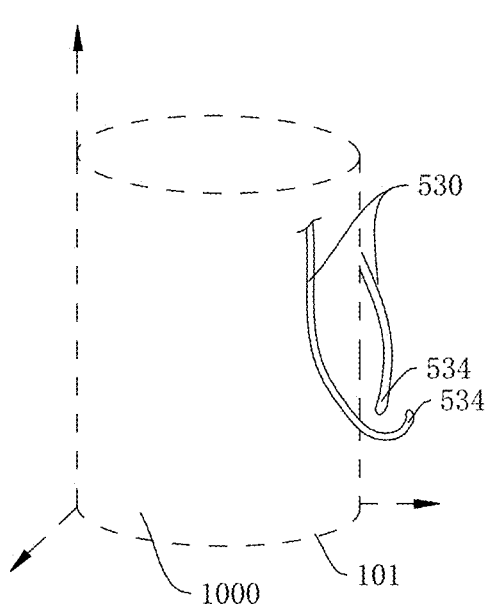
FIG. 72a is a view of wings of the guiding members according to one spatial configuration.
Figure 72B:
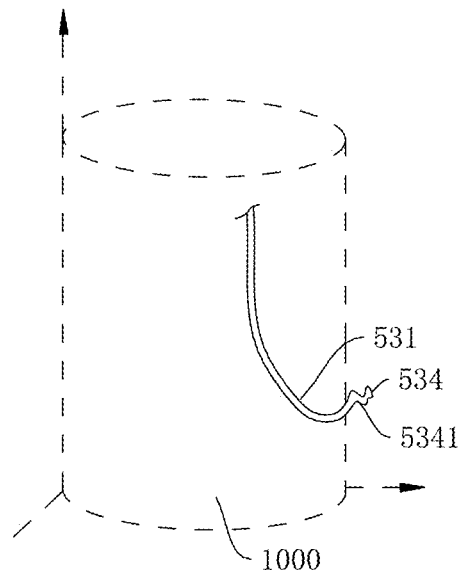
FIG. 72b is a view of wings of the guiding members according to another spatial configuration

FIGS. 68a-68c show three alternative configurations of the guiding member 530 in the released configuration, including: a first example, in which the guiding member 530 extends outward from the root 532 in the radial direction of the inner frame 103, and then is bent inward, as shown in FIG. 72a; a second example, in which the guiding member 530 extends from the root 532 in the axial direction of the inner frame 103 towards the outflow end 102 and is bent towards the inflow end 101, as shown in FIG. 72b; and a third example incorporating the first and the second examples, as shown in FIG. 72c.

Figure 69A:
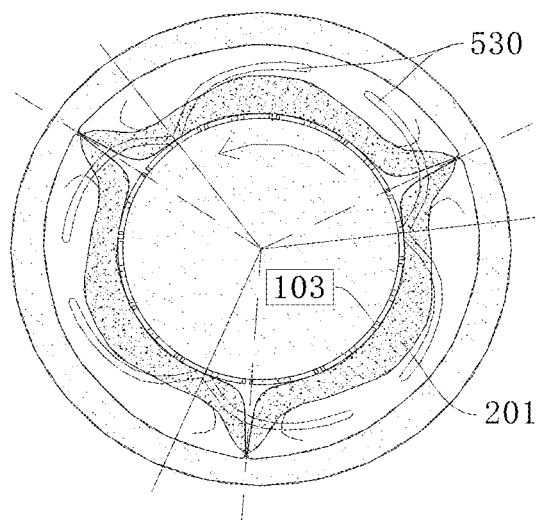
FIG. 69a is a view of the prosthetic aortic valve device and the aortic valve prior to circumferential positioning therebetween.
Figure 69B:
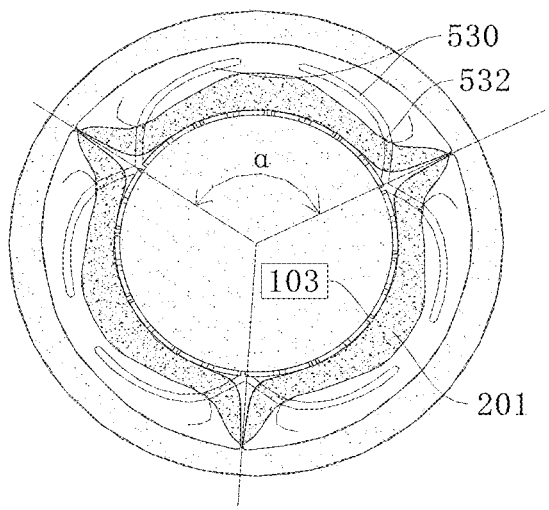
FIG. 69b is a view of the prosthetic aortic valve device and the aortic valve after circumferential positioning therebetween.

Referring to FIGS. 69a and 69b, in order to exactly guide the inner frame 103 to position and reduce the offset once in place, the guiding member 530 needs to have a sufficient circumferential span, which can be a span of different portions, for example, a portion of the root 532 or the wing 531, wherein the root 532 having the largest circumferential span is more advantageous for stabilizing the position of the inner frame 103. For example, take the root 532 as an example: in the circumferential direction of the inner frame 103, each guiding member 530 spans at least ⅙ circumference, i.e., the center angle α in FIG. 73b is greater than or equal to 60 degrees. Further, for example, each guiding member 530 spans ⅓ circumference in the circumferential direction of the inner frame 103, that is, the central angle α is equal to 120 degrees.

In order to facilitate smooth entry of the guiding member into the valvular sinus in the case where the root 532 has a large span, the guiding member has opposite outer and inner sides in the circumferential direction of the inner frame, and the edge of the wing on the outer side of the guiding member has a smooth contour. In addition, the curve of the contour extends from the root to the inflow end and is offset towards the inner side. The smooth contour and the extension of the curve facilitate the positioning of the guiding member itself in the valvular sinus, reducing the difficulty of adjusting and positioning the inner frame, and additionally reducing the potential safety hazard and avoiding puncturing the surrounding tissue.

After release of the guiding members 530, there may be deviations in the circumferential positions of the guiding members 530 from the positions of the valvular sinuses 204. For example, the areas represented by the three radially extending solid lines can be regarded as the approximate distribution regions of the three guiding members, while the areas represented by the three radially extending dotted lines can be regarded as the approximate distribution regions of the three valvular sinuses, which are not aligned with each other as shown in the figure, in which case, the inner frame 103 can be rotated in the direction of the solid arrow shown in the figure to drive the guiding members 530 until the three radially extending solid lines coincide with the dashed lines, so as to achieve circumferential alignment as shown in FIG. 73b.

After circumferential alignment, the inner frame 103 is moved towards the inflow end until the guiding members 530 abut against the sinus floors of the valvular sinuses 204 to achieve positioning. In the radial position, the native leaflet 201 is located between the guiding member 530 and the inner frame 103. The inner frame 103 can be then released and expanded by balloon, thereby avoiding the coronary artery.

In the released configuration, the ratio of the axial length of the guiding members 530 to the entire length of the inner frame 103 is 40% to 80%, for example, 50%.

Figure 70A:
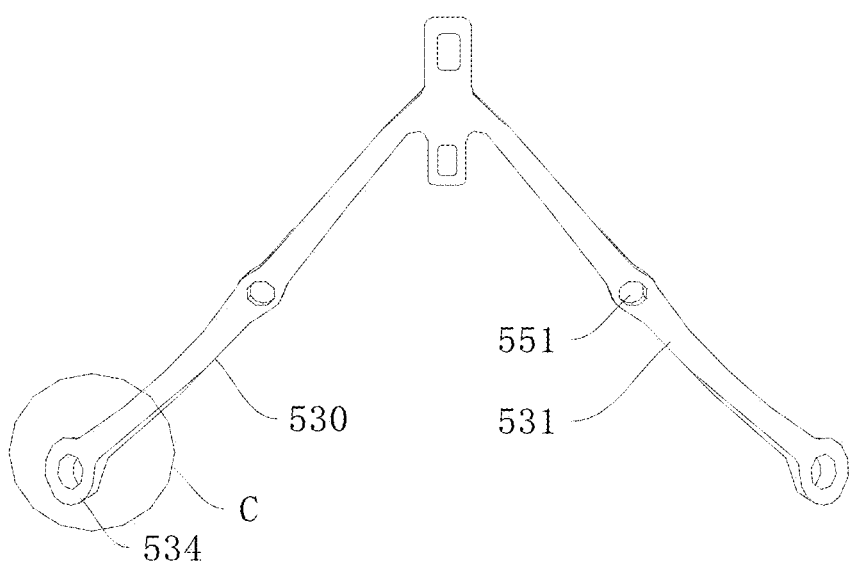
FIG. 70a is a view of a guiding member in an embodiment.
Figure 70B:
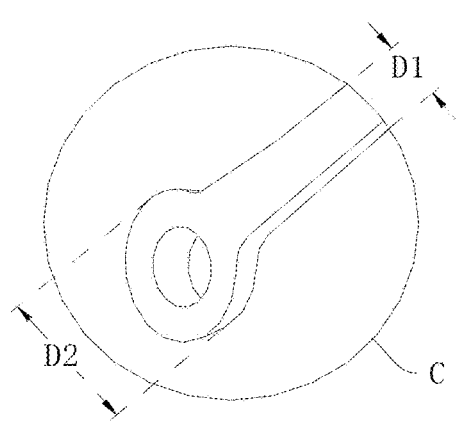

Referring to FIGS. 70a and 70b, in one embodiment, the free end 534 of the guiding member is configured as a ring structure with a smoothed outer periphery, the wing 531 is generally strip-shaped and has opposite length and width directions, and the width of the ring structure is larger than that of the wing 531. The width D2 of the ring structure is 2 to 6 times the width D1 of the wing 531.

Figure 70C:
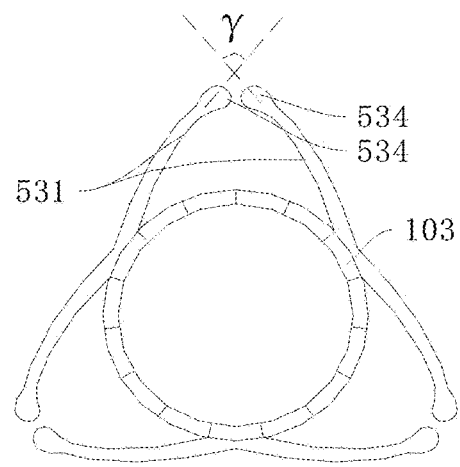
FIG. 70c is a view of the prosthetic aortic valve device in a transition configuration.

Referring to FIG. 70c, the free end 534 has a planar structure without considering the thickness of the material thereof, i.e., defines a reference plane, and in the transition configuration, the free ends 534 of the two wings 531 of the individual guiding member define a first reference plane and a second reference plane, respectively, and the angle γ between the first reference plane and the second reference plane is less than or equal to 90 degrees, preferably less than 45 degrees, for example 45 degrees.

Figure 70D:
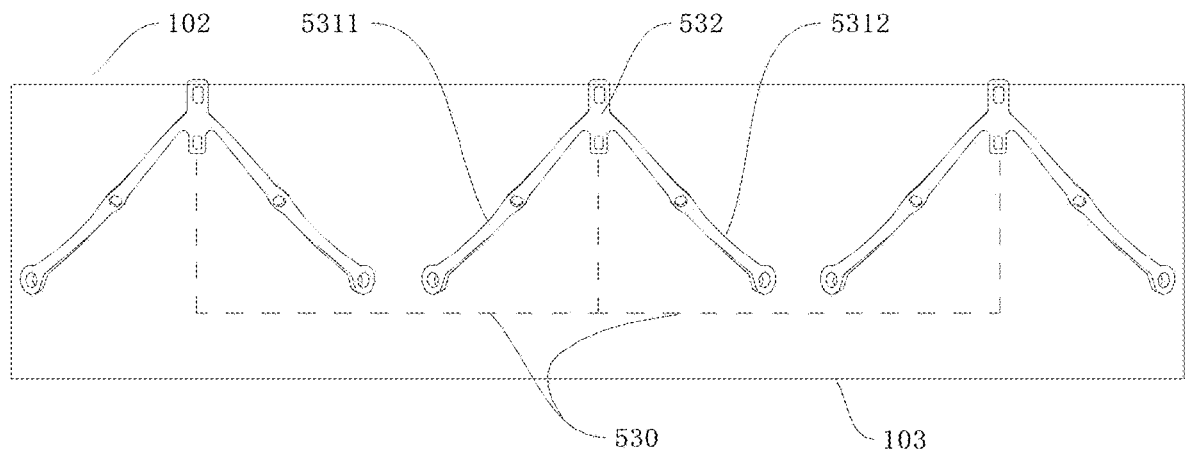
FIG. 70d is a flattened view of the prosthetic aortic valve device.

Referring to FIG. 70d, each guiding member 530 includes two wings 531. In two adjacent guiding members 530, a first wing 5311 of one of the guiding members 530 and a second wing 5312 of the other guiding member 530 are adjacent to each other in the circumferential direction of the inner frame 103. The outflow end 102 of the inner frame is provided with commissure posts 132, and the roots of the first wing 5311 and the second wing 5312 are connected to each other to form one piece which is overlapped and fixed to the outer side of the respective commissure post 132.

In connection with the above embodiments, the first wing 5311 and the second we 5312 are connected to a common root 532, which three can be considered to constitute one group of clipping arms. The prosthetic aortic valve device as a whole has three groups of clipping arms, and each group of clipping arms is separately connected to the inner frame.

In the released configuration, the first wing 5311 and the second wing 5312 are almost coplanar.

The roots 532 corresponding to the two wings 531 of the individual guiding member 530 are formed in one or separate pieces. In the case where the free ends 534 are separate from each other, if one of the wings were worked out, it would not pull the other, and since the roots 532 are close to the inner frame 103, the two wings 531 would not be pulled by each other. Taking the separate roots 532 as an example, the span of the guiding member 530 in the circumferential direction of the inner frame 103 can be understood as the central angle between the lines connecting the two roots 532 and the center of the inner frame 103, i.e., the central angle α shown in FIG. 73b.

Each wing 531 has a flat strip structure as a whole. The flat strip structure can be solid or totally hollowed out (leaving only the edge bars) or partially hollowed out (e.g. a meshed structure), for example by weaving or cutting. The flat strip structure can have a certain width, but does not necessarily extend with an equal width. The "flat" shape is more favorable for reducing the overall radial dimension during loading and ensuring compliance during intervention, while the "strip" shape is more favorable for space shaping.

Figure 71:
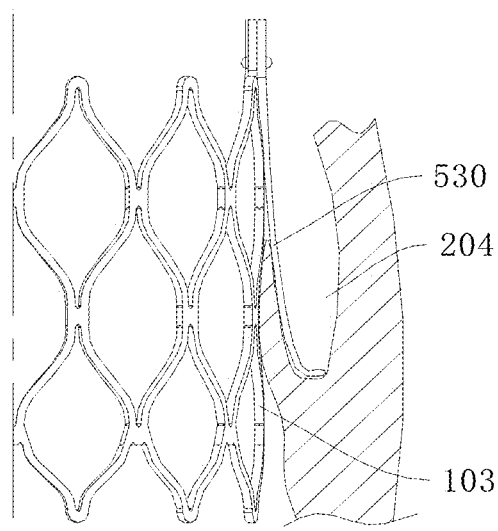
FIG. 71 shows the engagement between the guiding member and the valvular sinus after the former is inserted into the later.

Referring to FIG. 71 to FIG. 72b, the two wings 531 extend towards the inflow end 101 respectively from two outer sides of the respective guiding member 530, and approach each other.

The wing 531 generally has an arc configuration, and a wave structure 5341 can be provided adjacent to the free end 534 thereof, which can undulate in the radial and/or axial direction of the inner frame 103, or extend in the circumferential direction of the inner frame 103 at a section adjacent the free end 534. In the figure, the wave structure 5341 mainly undulates in the axial direction of the prosthetic aortic valve device. It will be conceived that the guiding member 530 can have undulations in multiple dimensions in three dimensions. Referring to the drawings, the guiding member 530 has a radially undulating structure in an axial view of the inner frame 103. The undulations in multiple directions can be provided separately or overlapped with each other to form a complex three-dimensional configuration.

In the transition configuration, the two wings 531 of the individual guiding member 530 have expanded outward, but the roots 532 of the two wings are restrained by the configuration of the inner frame 103 and are still adjacent to each other, in which case, the free ends 534 of the two wings 531 should not interfere with each other. Therefore, in the circumferential direction of the inner frame 103, the free ends 534 of the two wings 531 of the individual guiding member 530 are staggered with each other in the transition configuration of the guiding member 530, and in the released configuration, the free ends 534 of the two wings 531 in the individual guiding member 530 are spaced from each other.

The free ends 534 of the two wings 531 in the individual guiding member 530 are staggered with each other in the transition configuration of the guiding member 530 in such a way that the free ends 534 of the two wings 531 in the individual guiding member 530 are spaced in the radial or axial direction of the inner frame 103.

Figure 73A:
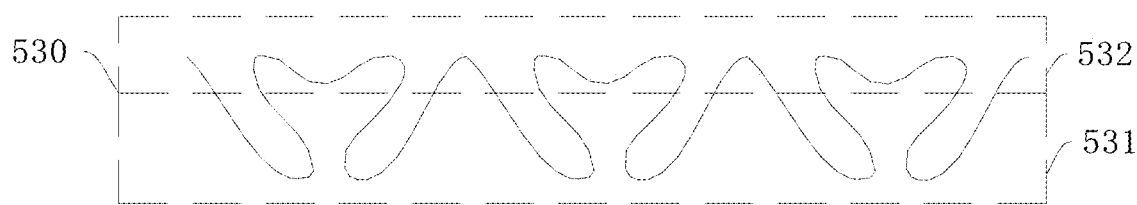
FIG. 73a is a flattened view of the one-piece guiding member.
Figure 73B:
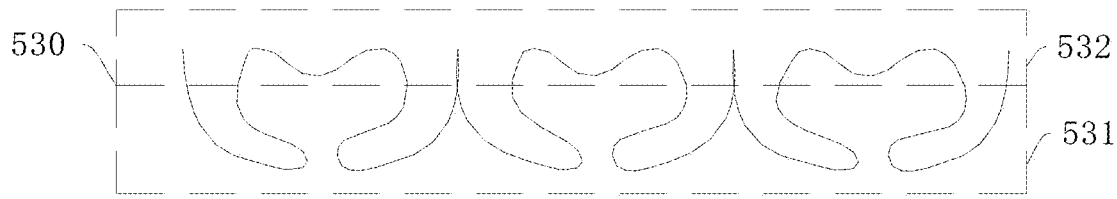
FIG. 73b is a flattened view of the one-piece guiding member in another form.
Figure 73C:
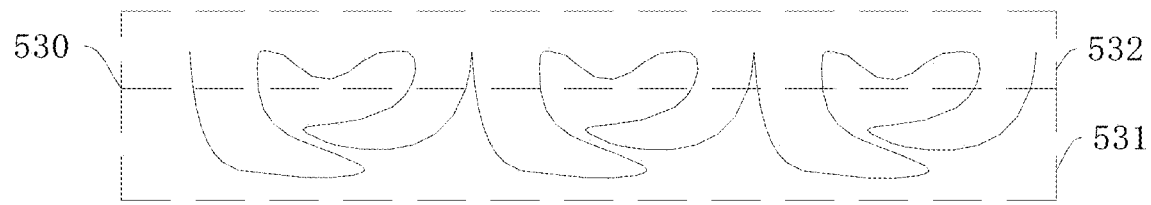
FIG. 73c is a flattened view of the one-piece guiding member in another form.

For ease of processing, referring to FIGS. 73a-73c, all of the guiding members 530 are formed in one piece, for example, by bending a strip of metal. Each of the wings 531 extends from opposite outer sides of the guiding member 530, which ensures the overall circumferential span of the guiding member 530. In the figure, the guiding members 530 have different shapes. In FIG. 73b, the guiding members 530 extend approximately in the axial direction of the inner frame 103, and then turn to extend approximately in the circumferential direction of the inner frame 103. As shown in FIG. 73c, the guiding members 530 in each group can be provided asymmetrically.

Figure 74A:
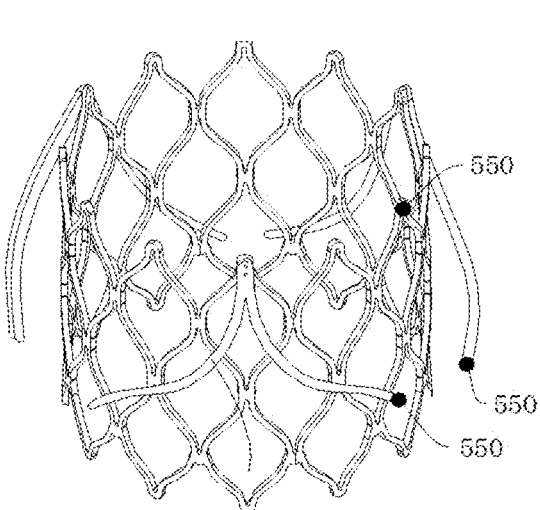
FIG. 74a is a perspective view showing the distribution of radiopaque markers in a prosthetic aortic valve device.
Figure 74B:
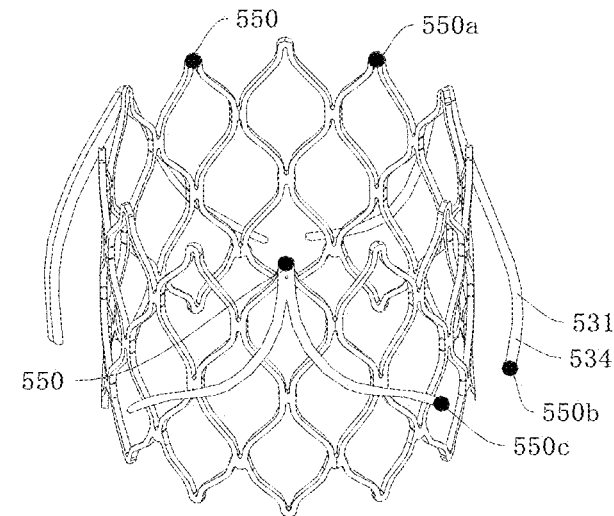
FIG. 74b is a perspective view showing the distribution of radiopaque markers in a prosthetic aortic valve device in another form.

Referring to FIGS. 74a-74b, in cooperation with an imaging equipment, the prosthetic aortic valve device 1000 can be provide with a radiopaque marker 550, which can be embedded or include a precious metal that can be displayed differentiating from other portions under X-ray or other means of detection.

The radiopaque marker 550 can be in the form of a dot or a strip or a ring (closed or non-closed, but at least in half ring), and the radiopaque marker 550 can be disposed in at least one of the inner frame 103 and the guiding members 530. For example, the inner frame 103 or the guiding members 530 are provided with eyelets for receiving the radiopaque marker 550.

The radiopaque marker 550 is installed, but not limited to one or more of the following methods: the wings 531 of the at least two guiding members 530 are provided with the radiopaque markers 550, and preferably, the wings 531 of all the guiding members 530 are provided with the radiopaque markers; the roots 532 of at least two of the guiding members 530 are provided with the radiopaque markers 550, and preferably the roots 532 of all the guiding members 530 are provided with the radiopaque markers.

In the axial view of the inner frame 103, at least three radiopaque markers 550 are visible and are distributed in different regions in the circumference of the inner frame 103. The position of the axis of the inner frame 103 can be determined according to the shape formed by the radiopaque markers 550 (displayed in the imaging equipment), so as to determine whether there is excessive tilt or the like.

In that axial view of the inner frame 103, at least three radiopaque markers 550 are visible and at least two are distributed in different regions in the radial direction of the inner frame 103. The radiopaque markers 550 in different regions in the radial direction can assist in determining the posture of the inner frame 103 in the circumferential direction.

In a radial view of that inner frame 103, at least three radiopaque markers 550 are visible and are distributed in different regions in the axial direction of the inner frame 103, in order to determine the position of the axis of the inner frame 103 from the radial view.

At least one radiopaque marker is disposed in the inner frame 103 or the root 532 of the guiding member 530, and at least one radiopaque marker is disposed in the wing 531 of the guiding member 530 and adjacent to the free end 534 of the wing 531, in order to determine the extension of the respective wing 531.

In combination of the above methods, as shown in FIG. 74b, for example, a first radiopaque marker 550a is arranged in the inner frame 103, a second radiopaque marker 550b and a third radiopaque marker 550c are arranged in the free ends 534 of the two wings 531. All these radiopaque markers 550 are distributed in different regions in the circumferential direction of the inner frame 103 from the axial view of the inner frame 103, and the first radiopaque markers 550a and the other two radiopaque markers are distributed in different regions in the radial direction of the inner frame 103, and the first radiopaque marker 550a and the other two radiopaque markers are also distributed in different regions in the axial direction of the inner frame 103. By means of the contrast medium, the posture of the prosthetic aortic valve device 1000 in the aorta and the alignment of the guiding members 530 with the valvular sinuses 204 can be easily determined.

Figure 75:
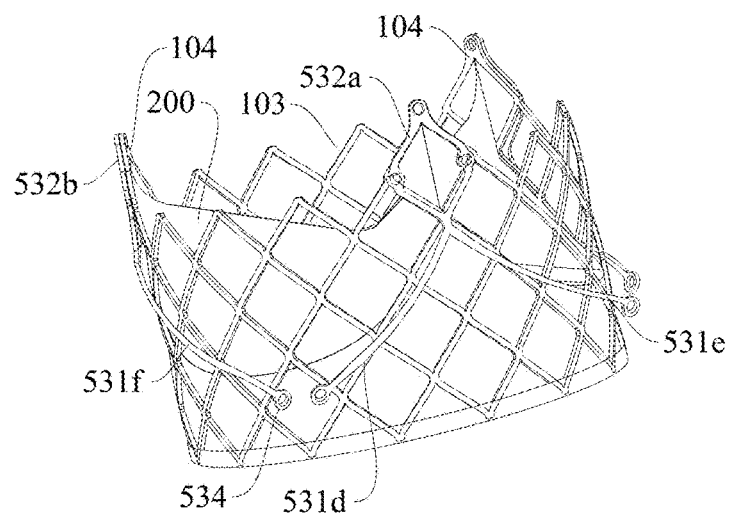

For example, FIG. 75 can be considered as showing another embodiment which combines FIGS. 51a to 51c which shows the shape characteristics and the spatial deformations of the joint between the root and the wing with FIG. 67, 70a, 1, or 19a or the like which shows the specific configurations of the wing.

Connecting posts 104 extend from the outflow end of the inner frame 103. The connecting post 104 is V-shaped and the sharp corner of the V-shape is axially convex, and the junction of the two adjacent leaflets 200 on the inner frame 103 is the commissure region of the inner frame 103. The connecting posts 104 are located at the respective commissure region in the circumferential direction, which is different from what shown in FIG. 27a, where the connecting post is located between adjacent two commissure regions.

In the following, the positioning structure for the prosthetic heart valve (which can also be regarded as the prosthetic aortic valve when applied to the aorta) in this embodiment will be described from different perspectives.

For the guiding member, there are three circumferentially arranged guiding members respectively corresponding to three valvular sinuses in the human body, and the guiding member includes two separate roots, for example a root 532a and a root 532b. The roots 532a and 532b are respectively connected to different connecting posts 104, the roots 532a further extends to form a wing 531d, the roots 532b further extends to form a wing 531f, and the free ends 534 of the wings 531d and 531f are separate of each other.

For the clipping arm, there are three groups of clipping arms arranged in circumferential direction, each group including two clipping arms. For example, one of the clipping arms has a root 532a which further extends to form two branched wings, wing 531d and wing 531e, respectively, wherein the free ends 534 of the wing 531d and the wing 531f in the other group of clipping arms are adjacent to each other and correspond to the same valvular sinus in vivo, which is more advantageous for avoiding coronary arteries.

The above different perspectives refer to the same structure. In this embodiment, the connection of the root and the wing refers to FIGS. 51a to 51c (the reference numerals in which are applied in the following). From the clipping arm, the root is fixed to the outer side of the inner frame by binding, including a first bar and a second bar, the wing includes, adjacent to the root, a third bar and a fourth bar, wherein one end of the third bar is connected to the first bar, and the other end of the third bar extends towards the inflow end; one end of the fourth bar is connected to the second bar, and the other end of the fourth bar extends towards the inflow end and intersects with the third bar. The third and fourth bars meet and then diverge away from each other until they extend to the free ends, with the different branches (such as the wing 531d and the wing 53le respectively in FIG. 75) corresponding to different valvular sinuses. The first bar 5321, the second bar 5322, the third bar 5351, and the fourth bar 5352 form a quadrangle, and the principle and deformation of the quadrangle, i.e., the frame, refer to the above, and would not be repeated herein.

Regarding the frame structure of the above embodiments, an embodiment of the present application further provides a prosthetic heart valve device having opposite inflow and outflow ends, including an inner frame 103, leaflets 200 and a positioning mechanism, wherein the inner frame 103 and the leaflets 200 can refer to the other embodiments. The difference between this embodiment and the other embodiments is that the present embodiment does not strictly limit the transition configuration of the positioning mechanism. For example, the prosthetic heart valve device specifically includes:

the inner frame 103, which has a radially deformable meshed cylindrical structure and has relative compressed and expanded configurations, and the interior of the inner frame 103 is configured as a blood flow passage axially passing therethrough;

leaflets 200, connected to the inner frame 103, wherein the leaflets 200 cooperate with each other to control opening and closing of the blood flow passage; and a positioning mechanism arranged in the circumferential direction of the inner frame, the positioning mechanism including a root 532 connected to the inner frame 103 and a wing 531 extending from the root 532 towards the inflow end; the wing is extendable in the peripheral region of the inner frame, with a receiving space defined between the wing and the outer wall of the inner frame for allowing the entry of the native leaflet; the roots 532 and the connection portions of the wings 531 with the roots 532 form as a frame structure; the two ends of the frame structure in the circumferential direction move relative to each other as the inner frame is compressed, and the two ends of the frame structure in the axial direction of the inner frame turn over relative to each other.

In this embodiment, the focus is that a frame structure (for example, enclosed by the first to fourth frame bars) is formed at the connection portion between the positioning mechanism and the inner frame, and the angle between the wing and the inner frame changes when the shape of the frame structure changes. Based on this, the native leaflets are clipped and positioned. The released structural configurations can also refer to FIG. 76 and FIG. 77.

Regarding the embodiments described above, the clipping arms or guiding members at the periphery of the inner frame can be regarded as the positioning mechanism, which allow the circumferential alignment with the valvular sinuses, and axial limitation of frame displacement. The positioning mechanism not directly connected to the two commissure regions in the circumferential direction also ensures the positioning effect.

In order to reduce the pulling effect among different portions and to ensure the accuracy and reliability of positioning into the respective valvular sinuses, a spacing region 111 is formed at the outer peripheral region of the inner frame between two adjacent commissure regions 114, and the positioning mechanism, as a whole, avoid the spacing region 111.

Due to the spacing region 111, any positioning member would not directly connect the two commissure regions 114. For example, in FIG. 76, the positioning mechanism can be considered as including a plurality of guiding members 530 located between adjacent two commissure regions 114, without being connected to the commissure regions 114 in the circumferential direction. Therefore, there are two spacing regions 111 between two adjacent commissure regions 114 in addition to the guiding member 530. The circumferential span of the guiding member 530 is limited, in order to realize circumferential alignment with valvular sinus.

Figure 77:
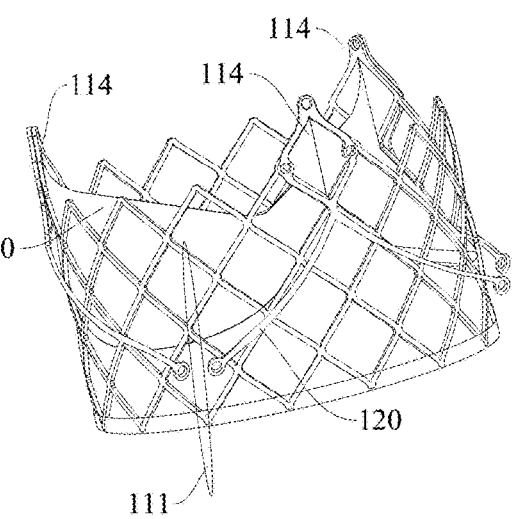

As another example, in FIG. 77, the free ends of the wings (from different clipping arms 120) on either side of the spacing region 111 are separate of each other and are not directly connected, providing more anchor points with the valvular sinus, reducing the risk of anchor failure.

Similarly, when the positioning mechanism includes a plurality of separate positioning members, the individual positioning member connected to the individual commissure region 114 is not directly connected to the other commissure regions. In other words, in the case where the positioning mechanism includes a plurality of separate positioning members, the individual positioning member is at most directly connected to one commissure region 114 (in the case where the guiding member 530 is connected between the two commissure regions 114, it can be considered not to be directly connected to any commissure region).

Based on the spaced distribution of the separate positioning members of the positioning mechanism, one embodiment of the present application further provides a prosthetic heart valve device having opposite inflow and outflow end. The prosthesis heart valve device includes an inner frame 103 and leaflets 200, wherein the inner frame and the leaflets can use conventional technique or the above embodiments. The prosthesis heart valve device further includes a positioning mechanism. The positioning mechanism includes a root connected to the inner frame and a wing extending from the root to the inflow end. The wing is extendable in the peripheral region of the inner frame, with a receiving space defined between the wing and the outer wall of the inner frame for allowing the entry of the native leaflet. The positioning mechanism is used to be placed at the corresponding valvular sinus in the human body to perform positioning. The clipping arms or guiding members can refer to the above embodiments, without strictly limiting the various configurations and the transformations.

Figure 76:
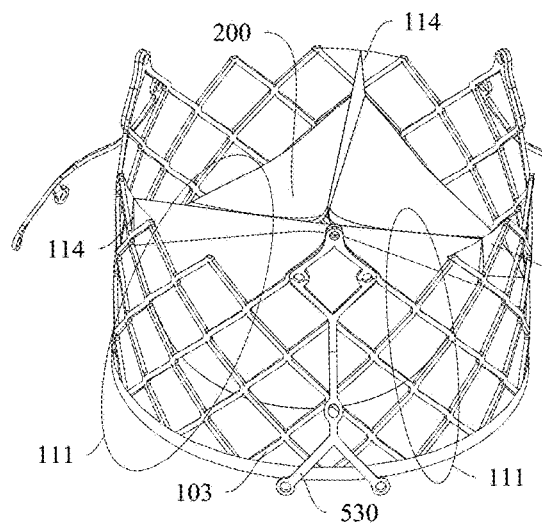

The focus of this embodiment is that the positioning mechanism includes a plurality of separate positioning members arranged sequentially in the circumferential direction of the inner frame, and the separate positioning members are indirectly connected to each other only by the inner frame 103. The positioning member can be a group of clipping arms (the configuration as shown in FIG. 74a), or guiding members with the roots between the two commissure regions (the configuration as shown in FIG. 76). Considering the structure of the native aortic valve, three separate positioning members are taken as example, which are not directly connected, but are respectively fixed to the inner frame, i.e., indirectly connected with each other through the inner frame. The free ends of the separate positioning members are not connected with each other, so that even if one of the leaflets is not positioned in place, such as being located outside of the positioning mechanism, the leaflets can also be positioned into the valvular sinuses, with a better fault tolerance.

In addition, the roots of the three separate positioning members are far away from each other in the circumferential direction, with a span therebetween corresponding to a central angle of approximately 120 degrees, so that after the inner frame 103 is released into the expanded configuration, the configurations of the separate positioning members are relatively independent from each other, in order to adapt to the more complex and even abnormal valvular sinuses.

Preferably, the inner frame is released and expanded by means of a balloon device and the positioning mechanism is released by self-expanding so that the positioning mechanism can have the above mentioned loaded, transition and released configurations. Taking the clipping arms shown in FIG. 74a and FIG. 75 as an example, each positioning member is a group of clipping arms, and one end of each clipping arm connected to the inner frame is a fixed end, while the other end is an opposite free end. Each group of clipping arms includes two clipping arms, wherein the fixed ends are adjacent to each other, and the free ends of the two clipping arms in each group are far away from each other. For example, the wings 531d and 531e extend away from each other. The connection portion between the respective group of clipping arms and the inner frame is aligned with the corresponding commissure region in the circumferential direction. Two clipping arms corresponding to the same leaflet belong to different groups in the circumferential direction, and the free ends thereof are spaced from each other and tend to close to each other. For example, the free end 534 of the wing 531d and the free end 534 of the wing 531f in the other group of clipping arms are adjacent to each other and correspond to the same valvular sinus in the human body.

The technical features of the above embodiments can be arbitrarily combined, and not all possible combinations of the technical features of the above embodiments have been described for the sake of brevity of description. However, as long as there is no contradiction in the combination of these technical features, it should be regarded as falling in the scope of this specification. When the technical features in different embodiments are shown in the same figure, it can be considered that the drawing also discloses a combination example of various embodiments involved.

The above-described embodiments only represent several embodiments of the present application, and the description therefor is specific and detailed, but should not be construed as limiting the scope of the patent application. It should be noted that a number of modifications and developments can be made to those of ordinary skill in the art without departing from the spirit of the present application, all of which are within the scope of protection of the present application.

What is claimed is:

1. A prosthetic heart valve device, comprising:
an inner frame having a meshed cylindrical structure which is radially deformable and opposite inflow and outflow ends, an interior of the inner frame being an axially-through blood flow passage, the inner frame having relative compressed and expanded configurations;
leaflets connected to the inner frame and cooperating with each other to control opening and closing of the blood flow passage; and
a positioner arranged in a circumferential direction of the inner frame, the positioner comprising a fixed end connected to the inner frame and a free end extending towards the inflow end, the positioner being configured to be switchable among the following configurations:
a loaded configuration, wherein the inner frame is in the compressed configuration, and the fixed end and the free end of the positioner contact or are adjacent to the inner frame in a radial direction of the inner frame;
a transition configuration, wherein inner frame is in the compressed configuration, while the free end of the positioner extends from a peripheral region of the inner frame, with a first receiving space defined between the free end of the positioner and an outer wall of the inner frame for allowing entry of a native leaflet; and
a released configuration, wherein the inner frame is in the expanded configuration, with a second receiving space defined between the free end of the positioner and the outer wall of the inner frame for clipping the native leaflet, wherein the prosthetic heart valve device is a prosthetic aortic valve device, wherein the outflow end of the inner frame is flared in the expanded configuration, and wherein a flared angle of the outflow end of the inner frame relative to an axial direction of the inner frame is defined as P4, wherein 0 degrees <P4≤45 degrees.

2. The prosthetic heart valve device according to claim 1, wherein P4 is in the range of 5 degrees to 25 degrees.

3. A prosthetic heart valve device, comprising:
an inner frame having a meshed cylindrical structure which is radially deformable and opposite inflow and outflow ends, an interior of the inner frame being an axially-through blood flow passage, the inner frame having relative compressed and expanded configurations;
leaflets connected to the inner frame and cooperating with each other to control opening and closing of the blood flow passage; and
a positioner arranged in a circumferential direction of the inner frame, the positioner comprising a fixed end connected to the inner frame and a free end extending towards the inflow end, the positioner being configured to be switchable among the following configurations:
a loaded configuration, wherein the inner frame is in the compressed configuration, and the fixed end and the free end of the positioner contact or are adjacent to the inner frame in a radial direction of the inner frame;
a transition configuration, wherein inner frame is in the compressed configuration, while the free end of the positioner extends from a peripheral region of the inner frame, with a first receiving space defined between the free end of the positioner and an outer wall of the inner frame for allowing entry of a native leaflet; and a released configuration, wherein the inner frame is in the expanded configuration, with a second receiving space defined between the free end of the positioner and the outer wall of the inner frame for clipping the native leaflet, wherein the positioner comprises guiding members arranged sequentially in the circumferential direction of the inner frame, and wherein a connection portion of each guiding member with the inner frame is a root, and a portion of each guiding member extending from the root towards the inflow end is a wing; and the guiding members are aligned with the respective leaflets in the circumferential direction of the inner frame, wherein the inner frame has at least two commissure regions corresponding to respective coaptation portions of adjacent leaflets, and the root of each guiding member is located between two commissure regions in the circumferential direction of the inner frame.

4. A prosthetic heart valve device, comprising:

an inner frame having a meshed cylindrical structure which is radially deformable and opposite inflow and outflow ends, an interior of the inner frame being an axially-through blood flow passage, the inner frame having relative compressed and expanded configurations;

leaflets connected to the inner frame and cooperating with each other to control opening and closing of the blood flow passage; and a positioner arranged in a circumferential direction of the inner frame, the positioner comprising a fixed end connected to the inner frame and a free end extending towards the inflow end, the positioner being configured to be switchable among the following configurations:

a loaded configuration, wherein the inner frame is in the compressed configuration, and the fixed end and the free end of the positioner contact or are adjacent to the inner frame in a radial direction of the inner frame;

a transition configuration, wherein inner frame is in the compressed configuration, while the free end of the positioner extends from a peripheral region of the inner frame, with a first receiving space defined between the free end of the positioner and an outer wall of the inner frame for allowing entry of a native leaflet; and a released configuration, wherein the inner frame is in the expanded configuration, with a second receiving space defined between the free end of the positioner and the outer wall of the inner frame for clipping the native leaflet, wherein the positioner comprises guiding members arranged sequentially in the circumferential direction of the inner frame, and wherein a connection portion of each guiding member with the inner frame is a root, and a portion of each guiding member extending from the root towards the inflow end is a wing; and the guiding members are aligned with the respective leaflets in the circumferential direction of the inner frame, wherein an angle between the wing and an axis of the inner frame in the transition configuration is P1, an angle between the wing and the axis of the inner frame in the released configuration is P2, and P1 is greater than P2.

5. The prosthetic heart valve device according to claim 4, wherein in the released configuration, the guiding member extends outward from the root and is bent inward in the radial direction of the inner frame.

6. The prosthetic heart valve device according to claim 4, wherein each of the guiding members is formed in one piece and switches among the configurations based on its own elastic deformation; and each of the guiding members is made of a memory alloy preset by heat treatment having a shape corresponding to the released configuration, and wherein the guiding member has internal stress in both the loaded configuration and the transition configuration relative to the released configuration.

7. The prosthetic heart valve device according to claim 4, wherein the wing has a branched structure adjacent to the root, and the branched structure is opened towards the outflow end.

8. The prosthetic heart valve device according to claim 7, wherein a portion of the wing adjacent the free end is split in the circumferential direction of the inner frame.

9. The prosthetic heart valve device according to claim 8, wherein the portion of the wing adjacent the free end is split into at least two branches.

10. The prosthetic heart valve device according to claim 8, wherein the free end is annular and covered with a protective layer; and the free end is provided with a first eyelet, the wing is provided with a second eyelet at a position preceding the split portion, and both the first eyelet and the second eyelet are provided with radiopaque markers.

11. The prosthetic heart valve device according to claim 8, wherein, in the released configuration, the free end of the wing is adjacent to or against the outer wall of the inner frame.

12. The prosthetic heart valve device according to claim 8, wherein the free end of each wing has a span corresponding to a central angle of 30 to 60 degrees in the circumferential direction of the inner frame.

13. The prosthetic heart valve device according to claim 4, wherein the root of the guiding member has a span with respect to the circumferential direction of the inner frame being ranged from 15 to 45 degrees; and the inner frame has a plurality of axially distributed cells, and the root of the guiding member has a span with respect to the circumferential direction of the inner frame corresponding to one or more cells.

14. The prosthetic heart valve device according to claim 4, wherein the root remains in abutment with the inner frame in each of the loaded configuration, the transition configuration, and the released configuration of the positioner; and the root is in abutment with a radially inner side or a radially outer side of the inner frame or is radially aligned with the inner frame.

15. The prosthetic heart valve device according to claim 4, wherein the root has a circumferential deformation between the transition configuration and the released configuration.

16. The prosthetic heart valve device according to claim 4, wherein the guiding member has opposite outer side and inner side in the circumferential direction of the inner frame, and the wing has a smooth contour at the outer side of the guiding member, which extends from the root to the inflow end.

17. The prosthetic heart valve device according to claim 16, wherein in the released configuration, the free ends of the two wings of the guiding member are spaced apart from each other, and the spacing region has a span corresponding to a central angle, in the circumferential direction of the inner frame, which is greater than 30 degrees.

18. The prosthetic heart valve device according to claim 16, wherein the free end has a planar structure, and in the transition configuration, the free ends of the two wings of the individual guiding member define a first reference plane and a second reference plane, respectively, and an angle between the first reference plane and the second reference plane is less than or equal to 90 degrees.

19. The prosthetic heart valve device according to claim 18, wherein the free end has an annular structure.

20. A prosthetic heart valve device, comprising:
an inner frame having a meshed cylindrical structure which is radially deformable and opposite inflow and outflow ends, an interior of the inner frame being an axially-through blood flow passage, the inner frame having relative compressed and expanded configurations;
leaflets connected to the inner frame and cooperating with each other to control opening and closing of the blood flow passage; and
a positioner arranged in a circumferential direction of the inner frame, the positioner comprising a fixed end connected to the inner frame and a free end extending towards the inflow end, the positioner being configured to be switchable among the following configurations:
a loaded configuration, wherein the inner frame is in the compressed configuration, and the fixed end and the free end of the positioner contact or are adjacent to the inner frame in a radial direction of the inner frame;
a transition configuration, wherein inner frame is in the compressed configuration, while the free end of the positioner extends from a peripheral region of the inner frame, with a first receiving space defined between the free end of the positioner and an outer wall of the inner frame for allowing entry of a native leaflet; and
a released configuration, wherein the inner frame is in the expanded configuration, with a second receiving space defined between the free end of the positioner and the outer wall of the inner frame for clipping the native leaflet, wherein the positioner comprises guiding members arranged sequentially in the circumferential direction of the inner frame, and wherein a connection portion of each guiding member with the inner frame is a root, and a portion of each guiding member extending from the root towards the inflow end is a wing; and
the guiding members are aligned with the respective leaflets in the circumferential direction of the inner frame, wherein the root comprises a first frame bar and a second frame bar, both of which can be twisted about their own longitudinal axes relative to the inner frame; and
the first frame bar and the second frame bar are bound to the inner frame, one end of the first frame bar and one end of the second frame bar are spaced apart from each other and connected to the wing, while the other end of the first frame bar and the other end of the second frame bar are fixed to the inner frame at the outflow end of the inner frame.

21. The prosthetic heart valve device according to claim 20, wherein the other end of the first frame bar and the other end of the second frame bar are intersected with, parallel to or spaced from each other; and an intersection of the first frame bar and the second frame bar comprises a wire binding eyelet.

22. A prosthetic heart valve device, comprising:
an inner frame having a meshed cylindrical structure which is radially deformable and opposite inflow and outflow ends, an interior of the inner frame being an axially-through blood flow passage, the inner frame having relative compressed and expanded configurations;
leaflets connected to the inner frame and cooperating with each other to control opening and closing of the blood flow passage; and
a positioner arranged in a circumferential direction of the inner frame, the positioner comprising a fixed end connected to the inner frame and a free end extending towards the inflow end, the positioner being configured to be switchable among the following configurations:
a loaded configuration, wherein the inner frame is in the compressed configuration, and the fixed end and the free end of the positioner contact or are adjacent to the inner frame in a radial direction of the inner frame;
a transition configuration, wherein inner frame is in the compressed configuration, while the free end of the positioner extends from a peripheral region of the inner frame, with a first receiving space defined between the free end of the positioner and an outer wall of the inner frame for allowing entry of a native leaflet; and
a released configuration, wherein the inner frame is in the expanded configuration, with a second receiving space defined between the free end of the positioner and the outer wall of the inner frame for clipping the native leaflet, wherein the positioner comprises guiding members arranged sequentially in the circumferential direction of the inner frame, and wherein a connection portion of each guiding member with the inner frame is a root, and a portion of each guiding member extending from the root towards the inflow end is a wing; and
the guiding members are aligned with the respective leaflets in the circumferential direction of the inner frame, wherein the root comprises a first frame bar and a second frame bar, and wherein one end of the first frame bar and one end of the second frame bar are spaced apart from each other and connected to the wing, while the other end of the first frame bar and the other end of the second frame bar are fixed to the inner frame, and the wing comprises, adjacent the root:
a third frame bar, one end of which is connected with the first frame bar, and the other end of which extends towards the inflow end; and
a fourth frame bar, one end of which is connected with the second frame bar, and the other end of which extends towards the inflow end and intersects with the third frame bar;
and wherein the first frame bar, the second frame bar, the third frame bar, and the fourth frame bar form as a frame structure; and
at least one of the four frame bars is configured to be twisted about its own longitudinal axis when the positioner is switched from the transition configuration to the released configuration.

23. The prosthetic heart valve device according to claim 22, wherein the first frame bar and the second frame bar define a first portion, and the third bar and the fourth bar define a second portion, and wherein in the transition configuration, an angle between the first portion and the second portion is Q1;
in the released configuration, an angle between the first portion and the second portion is Q2; and
Q1 is smaller than Q2, and the angle is an angle formed at an outer side of the inner frame.

24. The prosthetic heart valve device according to claim 22, wherein the third frame bar and the first frame bar have a first connection point therebetween, and the fourth frame bar and the second frame bar have a second connection point therebetween, and the first connection point and the second connection point are spaced from each other when the positioner is switched from the transition configuration to the released configuration, and an angle between the third frame bar and the first frame bar and an angle between the second frame bar and the fourth frame bar are substantially unchanged.

25. The prosthetic heart valve device according to claim 24, wherein the guiding member is provided with restricting structures at the first connection point and the second connection point, wherein the first connection point and the second connection point are bound to the inner frame by the restricting structures.

26. The prosthetic heart valve device according to claim 22, wherein the positioner is formed by separate positioning members which are independent from each other, and each positioning member is directly connected to at most one commissure region.

27. A prosthetic heart valve device, comprising:
an inner frame having a meshed cylindrical structure which is radially deformable and opposite inflow and outflow ends, an interior of the inner frame being an axially-through blood flow passage, the inner frame having relative compressed and expanded configurations;
leaflets connected to the inner frame and cooperating with each other to control opening and closing of the blood flow passage; and
a positioner arranged in a circumferential direction of the inner frame, the positioner comprising a fixed end connected to the inner frame and a free end extending towards the inflow end, the positioner being configured to be switchable among the following configurations:
a loaded configuration, wherein the inner frame is in the compressed configuration, and the fixed end and the free end of the positioner contact or are adjacent to the inner frame in a radial direction of the inner frame;
a transition configuration, wherein inner frame is in the compressed configuration, while the free end of the positioner extends from a peripheral region of the inner frame, with a first receiving space defined between the free end of the positioner and an outer wall of the inner frame for allowing entry of a native leaflet; and
a released configuration, wherein the inner frame is in the expanded configuration, with a second receiving space defined between the free end of the positioner and the outer wall of the inner frame for clipping the native leaflet, wherein the inner frame has at least two commissure regions corresponding to the respective coaptation portions of adjacent leaflets and provided sequentially in the circumferential direction of the inner frame, a spacing region is defined between two adjacent commissure regions in an outer peripheral region of the inner frame, and the positioner avoids the spacing region.

28. The prosthetic heart valve device according to claim 27, further comprising commissure posts extending from the outflow end of the inner frame, wherein an end of the commissure post is provided with a first collar, and an edge of the inner frame at the inflow end is provided with a second collar aligned with the first collar.

* * * * *

UNITED STATES PATENT AND TRADEMARK OFFICE
CERTIFICATE OF CORRECTION

Page 1 of 1

PATENT NO. : 12,226,313 B2
APPLICATION NO. : 18/557766
DATED : February 18, 2025
INVENTOR(S) : Charlie Clapp et al.

It is certified that error appears in the above-identified patent and that said Letters Patent is hereby corrected as shown below:

In the Claims

Column 56, Claim 1, Line 21: insert -- the -- before "inner frame"

Column 56, Claim 3, Line 21: insert -- the -- before "inner frame"

Column 57, Claim 4, Line 21: insert -- the -- before "inner frame"

Column 59, Claim 20, Line 21: insert -- the -- before "inner frame"

Column 60, Claim 22, Line 21: insert -- the -- before "inner frame"

Column 60, Claim 22, Line 58: delete "as"

Column 62, Claim 27, Line 21: insert -- the -- before "inner frame"

Signed and Sealed this
Eighteenth Day of November, 2025

John A. Squires
*Director of the United States Patent and Trademark Office*